(12) United States Patent
Schaefer et al.

(10) Patent No.: US 10,862,051 B2
(45) Date of Patent: *Dec. 8, 2020

(54) BENZIMIDAZO[1,2-A]BENZIMIDAZOLE DERIVATIVES FOR ELECTRONIC APPLICATIONS

(71) Applicant: UDC IRELAND LIMITED, Dublin (IE)

(72) Inventors: Thomas Schaefer, Liestal (CH); Flavio Luiz Benedito, Ludwigshafen (DE); Ute Heinemeyer, Neustadt (DE); Nicolle Langer, Lampertheim (DE); Heinz Wolleb, Fehren (CH); Teresa Marina Figueira Duarte, Hong Kong (CN); Soichi Watanabe, Mannheim (DE); Christian Lennartz, Schifferstadt (DE); Gerhard Wagenblast, Wachenheim (DE); Annemarie Wolleb, Fahren (CH); Kristina Bardon, Waldshut (DE)

(73) Assignee: UDC IRELAND LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/275,678

(22) Filed: Feb. 14, 2019

(65) Prior Publication Data
US 2019/0181355 A1    Jun. 13, 2019

Related U.S. Application Data

(63) Continuation of application No. 15/453,591, filed on Mar. 8, 2017, now Pat. No. 10,243,150, which is a
(Continued)

(30) Foreign Application Priority Data

Jul. 10, 2012  (EP) ..................... 12175635
Sep. 18, 2012  (EP) ..................... 12184786

(51) Int. Cl.
C07D 487/04 (2006.01)
H01L 51/00 (2006.01)
C09K 11/06 (2006.01)
H05B 33/00 (2006.01)
C07D 519/00 (2006.01)
(Continued)

(52) U.S. Cl.
CPC ........ *H01L 51/0072* (2013.01); *C07D 487/04* (2013.01); *C07D 519/00* (2013.01); *C09K 11/025* (2013.01); *C09K 11/06* (2013.01); *G03G 5/0661* (2013.01); *H01L 51/00* (2013.01); *H01L 51/0073* (2013.01); *H01L 51/0085* (2013.01); *H05B 33/00* (2013.01); *C09K 2211/1007* (2013.01); *C09K 2211/1074* (2013.01); *C09K 2211/185* (2013.01); *H01L 51/0054* (2013.01); *H01L 51/0077* (2013.01); *H01L 51/5012* (2013.01); *H01L 51/5016* (2013.01); *H01L 51/5056* (2013.01); *H01L 51/5096* (2013.01); *Y02E 10/549* (2013.01); *Y02P 70/521* (2015.11)

(58) Field of Classification Search
CPC .................................................. C07D 487/04
See application file for complete search history.

(56) References Cited

U.S. PATENT DOCUMENTS 6,551,723 B1   4/2003  Okada
7,244,746 B2   7/2007  Han
(Continued)

FOREIGN PATENT DOCUMENTS

EP   1191612 A2   3/2002
EP   1191613 A2   3/2002
(Continued)

OTHER PUBLICATIONS

Achour et al., Synthesis Des Benzimidazolo [1,2-a] Benzimidazoles a Partir Des Benzodiazepine-1, Sones-2, Bulletin des Societes Chimiques Beiges, vol. 96, No. 10, pp. 787-792 (1987).
(Continued)

*Primary Examiner* — Laura L Stockton
(74) *Attorney, Agent, or Firm* — Riverside Law LLP

(57) ABSTRACT

A compound of the general formula (I),

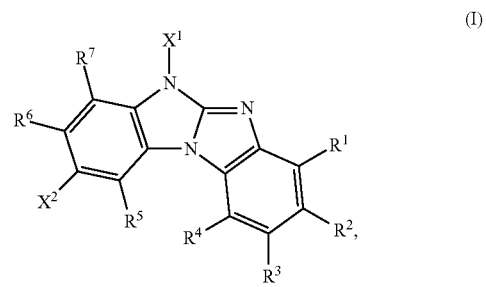

a process for the production of the compound and its use in electronic devices, especially electroluminescent devices. Improved efficiency, stability, manufacturability, or spectral characteristics of electroluminescent devices are provided when the compound of formula I is used as host material for phosphorescent emitters in electroluminescent devices.

15 Claims, No Drawings

Related U.S. Application Data continuation of application No. 14/413,736, filed as application No. PCT/EP2013/064395 on Jul. 8, 2013, now Pat. No. 9,620,724.

(60) Provisional application No. 61/669,677, filed on Jul. 10, 2012, provisional application No. 61/702,267, filed on Sep. 18, 2012.

(51) Int. Cl.
*G03G 5/06* (2006.01)
*C09K 11/02* (2006.01)
*H01L 51/50* (2006.01)

(56) References Cited

U.S. PATENT DOCUMENTS

| | | | |
|---|---|---|---|
| 8,674,091 | B2 | 3/2014 | Aihara |
| 10,243,150 | B2 * | 3/2019 | Schaefer ............... C09K 11/06 |
| 10,249,827 | B2 * | 4/2019 | Wolleb ................. C07D 405/14 |
| 2001/0015432 | A1 | 8/2001 | Igarashi |
| 2001/0019782 | A1 | 9/2001 | Igarashi |
| 2002/0024293 | A1 | 2/2002 | Igarashi |
| 2002/0048689 | A1 | 4/2002 | Igarashi |
| 2002/0055014 | A1 | 5/2002 | Okada |
| 2002/0094453 | A1 | 7/2002 | Takiguchi |
| 2005/0074632 | A1 | 4/2005 | Lee |
| 2005/0079387 | A1 | 4/2005 | Lee |
| 2009/0066226 | A1 | 3/2009 | Sugita |
| 2009/0153035 | A1 | 6/2009 | Shin |
| 2010/0244006 | A1 | 9/2010 | Ise |
| 2012/0095222 | A1 * | 4/2012 | Schaefer et al. ..... C07D 405/14 544/216 |
| 2012/0241681 | A1 | 9/2012 | Schaefer |
| 2013/0092922 | A1 | 4/2013 | Stoessel |
| 2015/0243907 | A1 | 8/2015 | Wolleb |
| 2017/0025627 | A1 | 1/2017 | Schaefer |
| 2018/0086763 | A1 * | 3/2018 | Raimann ............. H01L 51/0072 |

FOREIGN PATENT DOCUMENTS

| | | | |
|---|---|---|---|
| EP | 1211257 | A2 | 6/2002 |
| EP | 1885818 | A1 | 2/2008 |
| EP | 1970976 | A1 | 9/2008 |
| EP | 1998388 | A1 | 12/2008 |
| EP | 2034538 | A1 | 3/2009 |
| JP | 2000063818 | A | 2/2000 |
| JP | 2001160488 | A | 6/2001 |
| JP | 2004158327 | A | 6/2004 |
| JP | 2004531475 | A | 10/2004 |
| JP | 2007180147 | A | 7/2007 |
| JP | 201040829 | | 2/2010 |
| JP | 2010155826 | A | 7/2010 |
| KR | 20110008784 | A | 1/2011 |
| KR | 20120047038 | | 5/2012 |
| WO | 9947474 | A1 | 9/1999 |
| WO | 0070655 | A2 | 11/2000 |
| WO | 0141512 | A1 | 6/2001 |
| WO | 0202714 | A2 | 1/2002 |
| WO | 0215645 | A1 | 2/2002 |
| WO | 02060910 | A1 | 8/2002 |
| WO | 2005019373 | A2 | 3/2005 |
| WO | 2005033084 | A1 | 4/2005 |
| WO | 2005113704 | A2 | 12/2005 |
| WO | 2007095118 | A2 | 8/2007 |
| WO | 2007101820 | A1 | 9/2007 |
| WO | 2007115970 | A1 | 10/2007 |
| WO | 2007115981 | A1 | 10/2007 |
| WO | 2008000727 | A1 | 1/2008 |
| WO | 2008034758 | A2 | 3/2008 |
| WO | 2009050281 | A1 | 4/2009 |
| WO | 2009050290 | A1 | 4/2009 |
| WO | 2010056669 | A1 | 5/2010 |
| WO | 2010067894 | A1 | 6/2010 |
| WO | 2010079051 | A1 | 7/2010 |
| WO | 2010086089 | A1 | 8/2010 |
| WO | 2010129323 | A1 | 11/2010 |
| WO | 2011010842 | A2 | 1/2011 |
| WO | 2011019156 | A1 | 2/2011 |
| WO | 2011051404 | A1 | 5/2011 |
| WO | 2011073149 | A1 | 6/2011 |
| WO | 2011099718 | A1 | 8/2011 |
| WO | 2011160757 | A1 | 12/2011 |
| WO | 2012023947 | A1 | 2/2012 |
| WO | 2012080052 | A1 | 6/2012 |
| WO | 2012130709 | A1 | 10/2012 |
| WO | 2013050401 | A2 | 4/2013 |
| WO | 2013068374 | A2 | 5/2013 |
| WO | 2013068376 | A1 | 5/2013 |
| WO | 2013108997 | | 7/2013 |
| WO | 2012035853 | | 2/2014 |

OTHER PUBLICATIONS

Andre J. Hubert, et al., 'Thermolyse and Photolyse von Benzotriazolyl-(1)-Derivaten', Chemische Berichte, vol. 103 (1970), pp. 2828-2835.

B.A. Priimenko, et. al., Chemistry of Heterocyclic Compounds, vol. 17, No. 9 (1981) pp. 937-940.

Cheminform, vol. 35, p. 2004 (referencing RevuRoumaine de Chimie, vol. 49, pp. 157-161 (2004).

Cheminform, vol. 35, p. 2004 (RevuRoumaine de Chimie, vol. 49, R 157-161) (2004).

Dawood et al., Synthesis of 3,3'-bi-1,2,4-Triazolo[4,5-a]benzimidazole, 5,5'-bi-1,3,4-Thiadiazole, and Thiazolo[3,2-a] benzimidazole Derivatives, Synthetic Communications, vol. 33, No. 23, pp. 4079-4086 (2003), Abstract Only Provided.

Hassaneen et al., A One Step Synthesis of Benzimidazo [2,1-c][1,2,4]Triazole Derivatives Using Hydrazonoyl Halides, Heterocycles, vol. 36, No. 8, pp. 1775-1781 (1993).

I.V. Kolesnikova, et al., 'Reaction of N-Pentafluorophenylcarbonimidoyl Dichloride with Primary Amines' Zhurnal Organicheskoi Kimii, vol. 25, 1989, pp. 1523-1529.

I.V. Kolesnikova, et al., 'Reactions of N-Polyfluorophenylcarbonimidoyl Dichlorides With Primary and Secondary Amines. Kinetics and Mechanism. Synthesis of Polyfluorinated Carbodiimides, Chloroformamidines, Guanidines and Benzimidazoles' Journal of Fluorine Chemistry, vol. 40, 1988, pp. 217-246.

Kolesnikova, I.V., et al. "Zhurnal Organicheskoi Khimii" 25, (1989) pp. 1689-1695.

M.V. Povstyanoi, et al., 'Synthesis of 2-Methylmercapto-3-Acylmethyl(.beta.-Hydroxyalkyl)Naphth[1,2-d]Imidazoles and their conversion to Naphth[1,2-d]Imidazo[3,2-b]Imidazole and Naphth [1,2-d]Imidazo[3,2-b] Imidazoline Derivatives' Chemistry of Heterocyclic Compounds, vol. 8, 1972, pp. 738-741.

M.V. Povstyanoli, et al., "Synthesis of 2-Methylmercapto-3-Acylmethyl((3-Hydroxyalkyl)Naphth[1,2-d]Imidazoles and their conversion to Naphth[1,2-d]Imidazol[3,2-b] Imidazoline Derivatives" Chemistry of Heterocyclic Compounds, vol. 8, 1972, pp. 738-741.

Misbahul Ain Khan, et al., 'Tetracyclic Heteroaromatic Systems. Part-II. Benzimidazo [1,2-a] Benzimidazoles', Pakistan Journal of Scientific and Industrial Research, vol. 43, No. 3, (2000), pp. 168-170.

Olaj, Szappan, Kozmetika, vol. 59, pp. 49-55 Chemical Abstracts [online] [retrieved Nov. 2015 from STN] (2010)., CA 154:284203, Abstract Only Provided.

Pedro Molina, et al., 'Synthetic: Applications of C,C-Bis (Iminophosphoranes):Preparation of [5+5] Rigid Bicyclic Guanidines and 1,3,6-Benzothiadiazepino [3,2-a] benzimidazole Derivatives', Tetrahedron, vol. 50, No. 33, Elsevier Science Ltd.,(1994) 10029-10036.

V. S. Ponomar et al., "Investigations in the midazole Series LXX. Synthesis of Derivatives of 1(9)H-and 1h-Imidazo[1,2-A]Benzimidazoles," Khimiya Geterotsiklicheskikh Soedinenii, Issue 2, pp. 229-231, Sep. 29, 1972.

V.S. Ponomar, et al., "Investigations in the Imidazole Series LXX. Synthesis of Derivatives of 1(9)H-and 1H-Imidazol [1,2-a]Benzimidazoles" Chemistry of Heterocyclic Compounds, vol. 8, 1972, pp. 229-231.

(56) References Cited

OTHER PUBLICATIONS

Xiaoqiang Wang, et al., 'Copper-Catalyzed Aerobic Oxidative Intramolecular C-H Amination Leading to Imidazobenzimidazole Derivatives', Organic Letters, vol. 14, No. 2, (2012), pp. 452-455.

* cited by examiner

BENZIMIDAZO[1,2-A]BENZIMIDAZOLE DERIVATIVES FOR ELECTRONIC APPLICATIONS

CROSS-REFERENCE TO RELATED APPLICATIONS

The present application is a continuation of U.S. patent application Ser. No. 15/453,591, filed Mar. 8, 2017, now allowed, which is a continuation of U.S. patent application Ser. No. 14/413,736, filed Jan. 9, 2015, now U.S. Pat. No. 9,620,724, which is the U.S. National Stage Application filed under 35 U.S.C. § 371 of International Patent Application No. PCT/EP2013/064395, filed Jul. 8, 2013, which claims priority to U.S. Provisional Patent Application Nos. 61/669,677, filed Jul. 10, 2012, and 61/702,267, filed Sep. 18, 2012, and European Patent Application Nos. 12175635.7, filed Jul. 10, 2012, and 12184786.7, filed Sep. 18, 2012, all of which applications are hereby incorporated by reference in their entireties.

The present invention relates to compounds of formula I, a process for their production and their use in electronic devices, especially electroluminescent devices. When used as hole transport material in electroluminescent devices, the compounds of formula I may provide improved efficiency, stability, manufacturability, or spectral characteristics of electroluminescent devices.

Khan, Misbahul Ain; Ribeiro, Vera Lucia Teixeira, Pakistan Journal of Scientific and Industrial Research 43 (2000) 168-170 describes the synthesis of benzimidazo[1,2-a]benzimadozoles

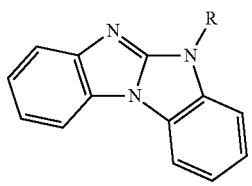

(R=H, Me, Et) by trialkyl phosphite-induced deoxygenation and thermolysis of 1-(o-nitrophenyl)- and 1-(o-azidophenyl)benzimidazoles.

Pedro Molina et al. Tetrahedron (1994) 10029-10036 reports that aza Wittig-type reaction of bis(iminophosphoranes), derived from bis(2-aminophenyl)amine with two equivalents of isocyanate directly provided benzimidazo[1,2,a]benzimidazole derivatives.

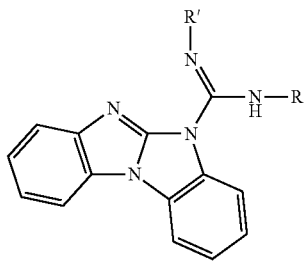

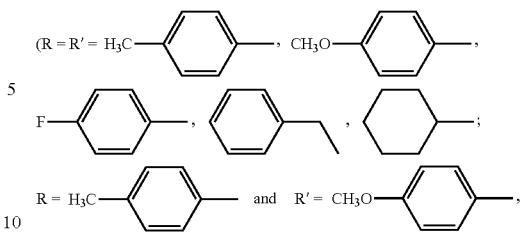

R=isopropyl and R'=ethyl)

Kolesnikova, I. V.; Zhurnal Organicheskoi Khimii 25 (1989) 1689-95 describes the synthesis of 5H-benzimidazo[1,2-a]benzimidazole 1,2,3,4,7,8,9,10-octafluoro-5-(2,3,4,5,6-pentafluorophenyl).

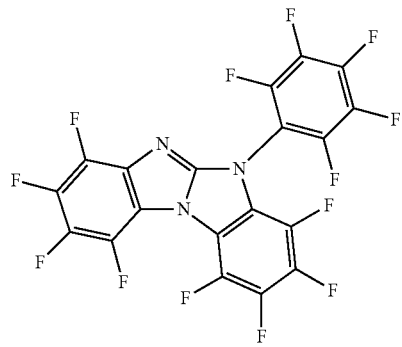 [SMILES: Fc1c(F)c(F)c(-n2c3c(F)c(F)c(F)c(F)c3n3c4c(F)c(F)c(F)c(F)c4nc23)c(F)c1F]

Achour, Reddouane; Zniber, Rachid, Bulletin des Societes Chimiques Belges 96 (1987) 787-92 describes the synthesis of benzimidazobenzimidazoles

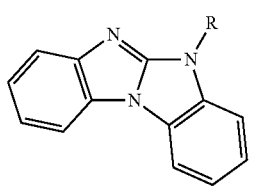

(R=H, —CH(CH$_3$)$_2$) which were prepared from benzimidazolinone derivatives.

Hubert, Andre J.; Reimlinger, Hans, Chemische Berichte 103 (1970) 2828-35 describes the synthesis of benzimidazobenzimidazoles

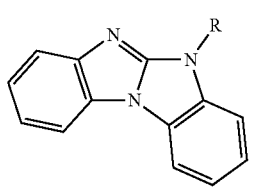

(R═H, CH₃,

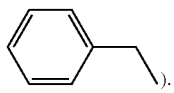

).

JP2001160488 describes an electroluminescent element which has a light-emitting layer having a single-layer or multiple-layer organic compound film between opposing anode and cathode, wherein at least one layer of the organic compound film contains at least one kind of compounds indicated by formula

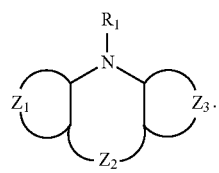

The following compounds are explicitly disclosed:

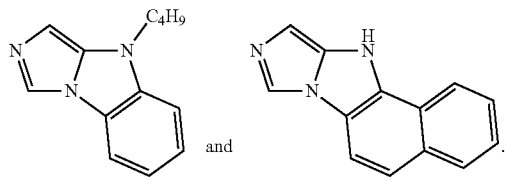

US20100244006 relates to an organic electroluminescent device which includes: a cathode; an anode; and at least one organic layer between the cathode and the anode. The at least one organic layer includes a light emitting layer containing at least one light emitting material. A compound represented by the following formula

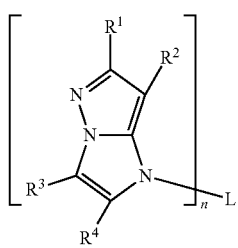

(I)

is contained in the at least one organic layer. where n stands for an integer of 2 or greater, L represents an n-valent linking group, and $R^1$, $R^2$, $R^3$, and $R^4$ each independently represents a hydrogen atom or a substituent.

The compounds described in US20100244006 are preferably used in as host in the light emitting layer.

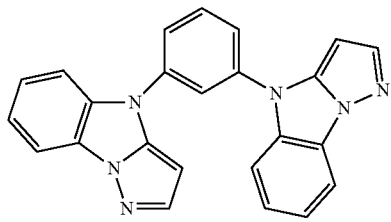 [SMILES: c1cc(-n2c3ccccc3n3nccc23)cc(-n2c3ccccc3n3nccc23)c1]

represents an example of a compound disclosed in US20100244006.

KR1020110008784 relates to novel organic luminescent compounds of formula

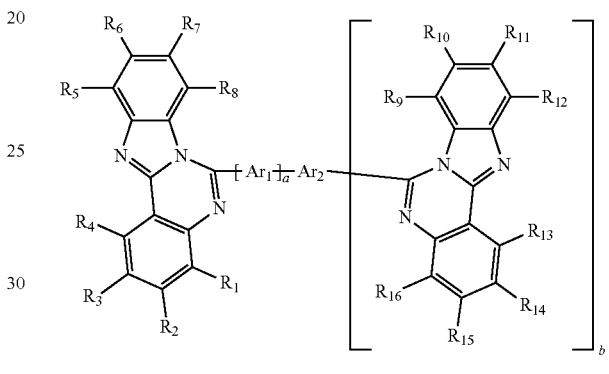

and organic electroluminescence devices including the same.

US2005079387 relates to an imidazole ring containing compound of formula $Ar_1$—$Ar_2$—$Ar_3$, (blue luminescent host compound) and an organic electroluminescence (EL) display device using the same.

$Ar_2$ is selected from the group consisting of

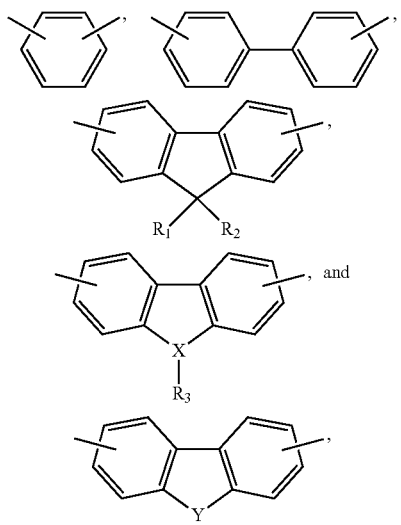

each of $Ar_1$ and $Ar_3$ is independently selected from

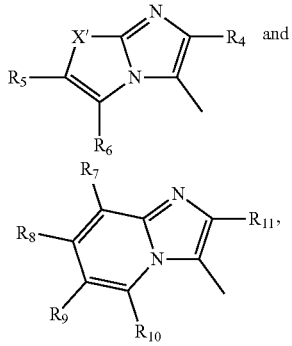

wherein X' is O, or S.

US2005074632 relates to an imidazole ring containing compound of formula

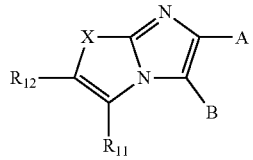

and an organic electroluminescence (EL) display device using the same. In particular, the imidazole ring-containing compound may be used alone or in combination with a dopant as a material for organic films such as an electroluminescent layer.

A is selected from the group consisting of

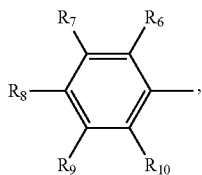

—$N(R_{13}R_{14})$, and

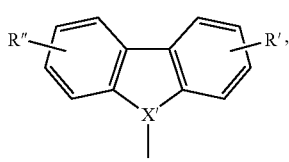

B is selected from the group consisting of

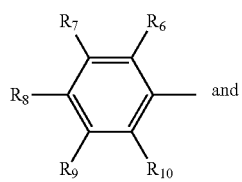

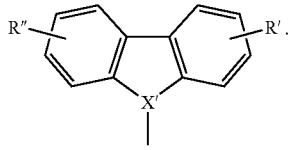

X is selected from the group consisting of —O—, —S—, —Se— and —NH—.

JP2007180147 relates to an organic electroluminescence element, sandwiched by an anode and a cathode and containing at least a light-emitting layer, which contains a compound represented by general formula 1, 2, 3 or 4:

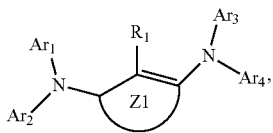

(1)

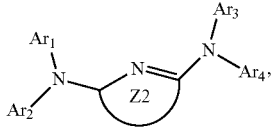

(2)

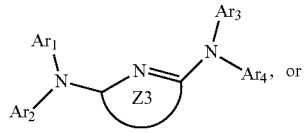

(3)

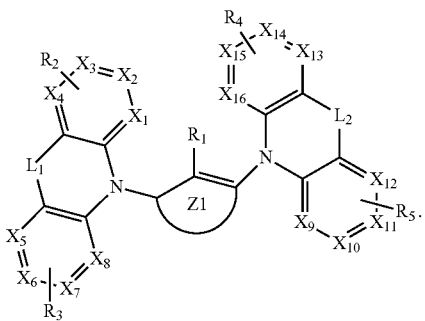

(4)

$Ar_1$-$Ar_4$=aromatic group or aromatic heterocyclic group; $R_1$-$R_5$=H or substituent; $Z_1$=residue required to form heterocyclic ring of 5 or 6 members; $L_1$, $L_2$=bond or coupling group; and $X_1$-$X_{16}$=carbon or nitrogen. A new ring can be formed in one portion of $Ar_1$ and $Ar_2$, and $Ar_3$ and $Ar_4$.

The following compounds are explicitly disclosed:

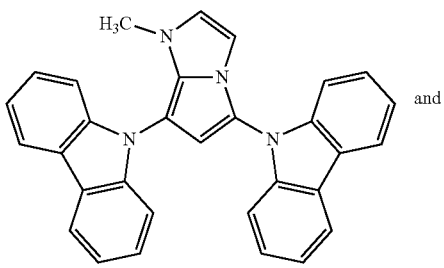

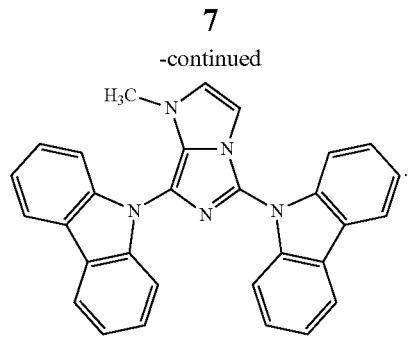

U.S. Pat. No. 6,551,723 relates to an organic electroluminescence element comprising a light-emitting layer or a plurality of organic compound thin layers containing a light-emitting layer between a pair of electrodes, wherein at least one layer in the organic electroluminescence element comprises at least one heterocyclic compound represented by formula (I) to (VII):

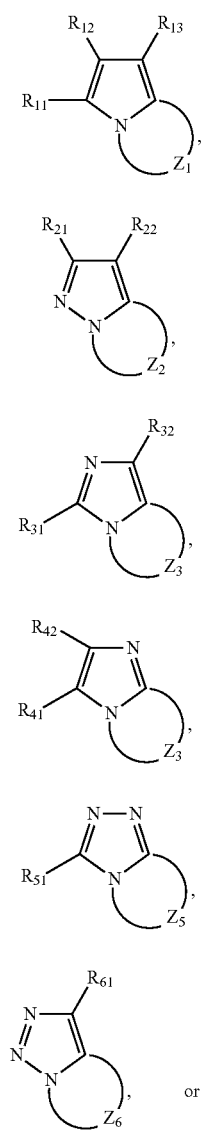

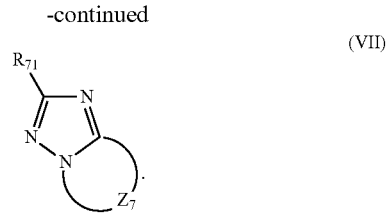

$R_{11}$, $R_{12}$, $R_{13}$, $R_{21}$, $R_{22}$, $R_{31}$, $R_{32}$, $R_{41}$, $R_{42}$, $R_{51}$, $R_{61}$, and $R_{71}$ are each independently a hydrogen atom or substituent; $Z_1$, $Z_2$, $Z_3$, $Z_4$, $Z_5$, $Z_6$, and $Z_7$ are a group of atoms that are necessary for forming a 5- or 6-member ring. The compounds represented by formula (I) to (VII) are particularly added to a light-emitting layer and/or electron injection/transporting layer. The following compounds are explicitly disclosed:

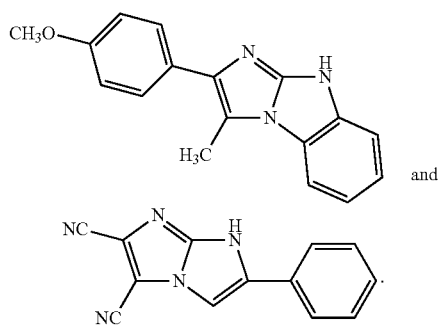

WO2011160757 relates to an electronic device comprising an anode, cathode and at least one organic layer which contains a compound of formulae

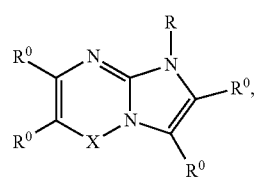

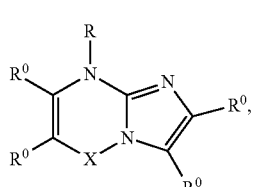

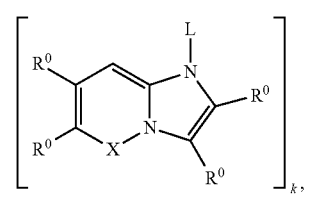

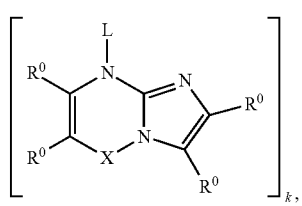
(IV)
wherein X may be a single bond and L may be a divalent group. The following 4H-Imidazo[1,2-a]imidazole compounds are explicitly disclosed:
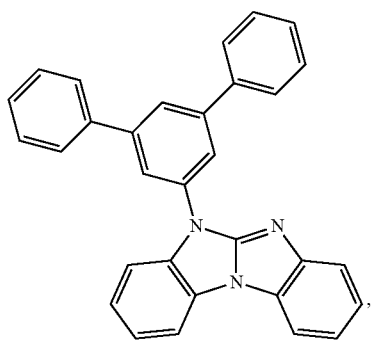
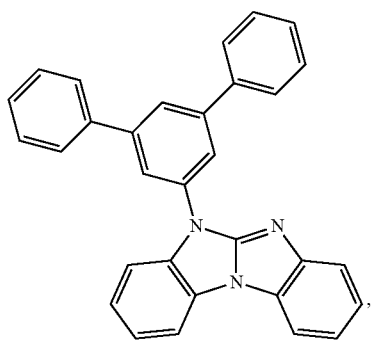
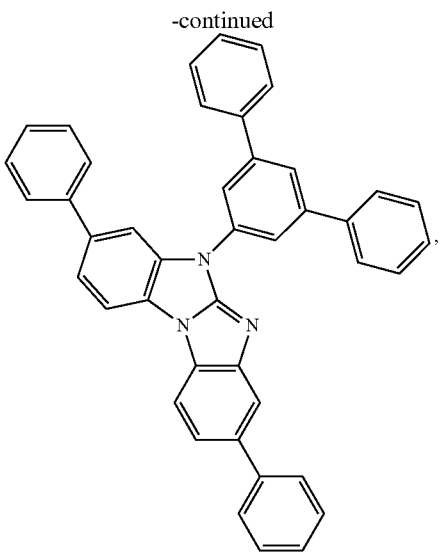
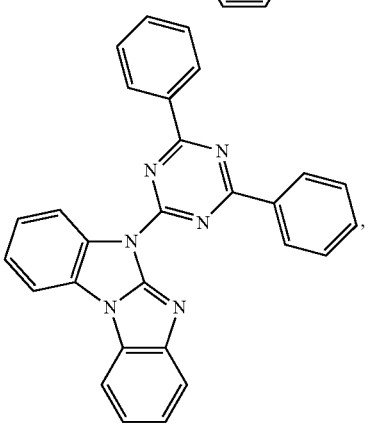
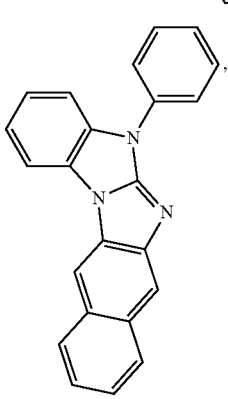
and
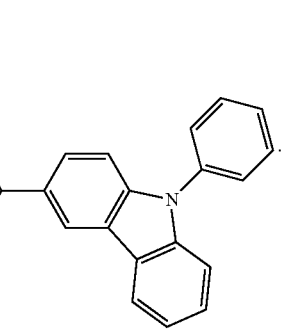

X. Wang et al. Org. Lett. 14 (2012) 452-455 discloses a highly efficient copper-catalyzed synthesis for compounds of formula

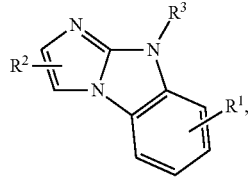

wherein compounds of formula

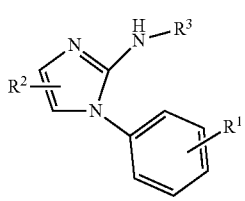

are reacted in the presence of copper acetate (Cu(OAc)$_2$)/PPh$_3$/1,10-phenathroline/sodium acetate and oxygen in m-xylene (1 atm) at elevated temperature [published on web: Dec. 29, 2011]. Among others the following compounds can be prepared by the described synthesis method:

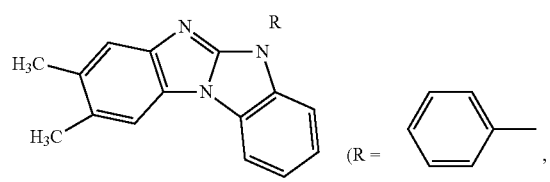

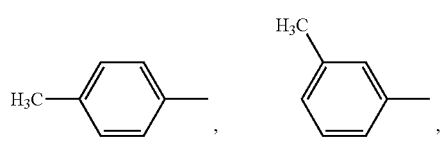

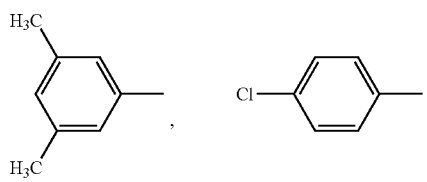

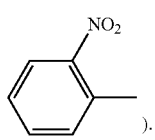

WO2012/130709 relates to 4H-Imidazo[1,2-a]imidazoles,

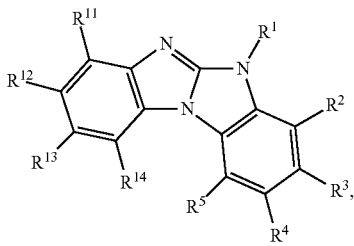

such as, for example,

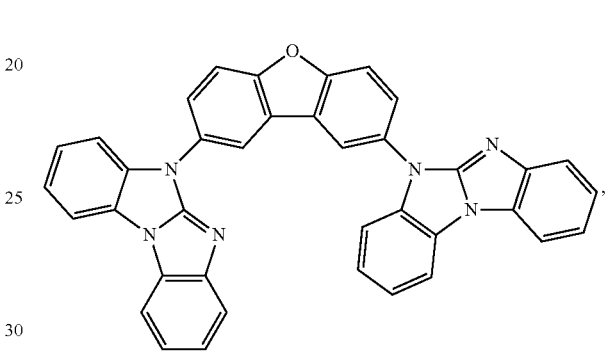

a process for their production and their use in electronic devices, especially electroluminescent devices.

WO2013/050401 describes 4H-imidazo[1,2-a]imidazoles of formula

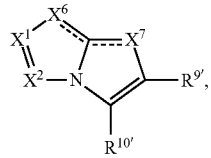

wherein $X^6$ is —N= and $X^7$ is —NR$^6$—, or $X^7$ is =N— and $X^6$ is —NR$^6$—, R$^6$ is a group of formula

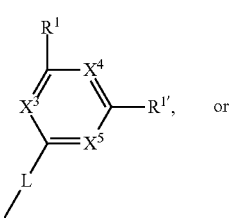

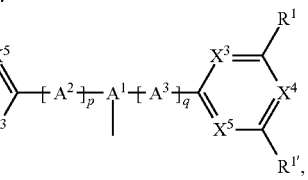

such as, for example,

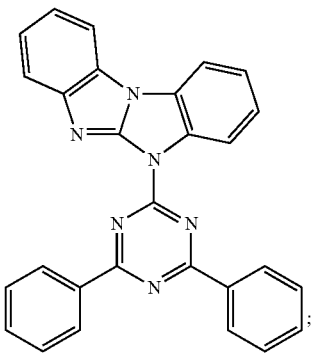 [SMILES: c1ccc(-c2nc(-c3ccccc3)nc(-n3c4ccccc4n4c5ccccc5nc34)n2)cc1]

a process for their production and their use in electronic devices, especially electroluminescent devices.

Notwithstanding these developments, there remains a need for organic light emitting devices comprising new hole transport materials to provide improved efficiency, stability, manufacturability, and/or spectral characteristics of electroluminescent devices.

Accordingly, it is an object of the present invention, with respect to the aforementioned prior art, to provide further materials suitable for use in OLEDs and further applications in organic electronics. More particularly, it should be possible to provide hole transport materials, electron/exciton blocker materials and matrix materials for use in OLEDs. The materials should be suitable especially for OLEDs which comprise at least one phosphorescence emitter, especially at least one green emitter or at least one blue emitter. Furthermore, the materials should be suitable for providing OLEDs which ensure good efficiencies, good operative lifetimes and a high stability to thermal stress, and a low use and operating voltage of the OLEDs.

Certain 2,5-disubstituted benzimidazo[1,2-a]benzimidazole derivatives are found to be suitable for use in organo-electroluminescent devices. In particular, certain 2,5-disubstituted benzimidazo[1,2-a]benzimidazole derivatives are suitable hole transporting materials, or host materials for phosphorescent emitters with good efficiency and durability.

Said object has been solved by compounds of the formula

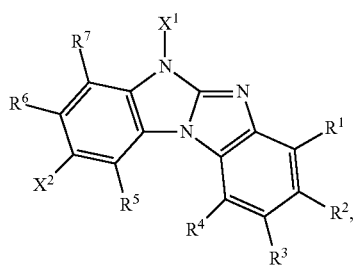

(I)

wherein $R^1$, $R^2$, $R^3$, $R^4$, $R^5$, $R^6$ and $R^7$ are independently of each other H, a $C_1$-$C_{25}$alkyl group, which can optionally be substituted by E and or interupted by D; a $C_6$-$C_{24}$aryl group, which can optionally be substituted by G, or a $C_2$-$C_{30}$heteroaryl group, which can optionally be substituted by G;

$X^1$ is a group of formula —$(A^1)_o$-$(A^2)_p$-$(A^3)_q$-$(A^4)_r$—$R^{16'}$, o is 0, or 1, p is 0, or 1, q is 0, or 1, r is 0, or 1, $A^1$, $A^2$, $A^3$ and $A^4$ are independently of each other a $C_6$-$C_{24}$arylen group, which can optionally be substituted by G, or a $C_2$-$C_{30}$heteroarylen group, which can optionally be substituted by G; wherein the groups $A^1$, $A^2$, $A^3$ and $A^4$ may be interrupted by one, or more groups —$(SiR^{17}R^{18})$—;

$X^2$ is a group of formula —$(A^5)_v$-$(A^6)_s$-$(A^7)_t$-$(A^8)_u$—$R^{15}$, —$NR^{10}R^{11}$, or $Si(R^{12})(R^{13})(R^{14})$, v is 0, or 1, s is 0, or 1, t is 0, or 1, u is 0, or 1, $A^5$, $A^6$, $A^7$ and $A^8$ are independently of each other a $C_6$-$C_{24}$arylen group, which can optionally be substituted by G, or a $C_2$-$C_{30}$heteroarylen group, which can optionally be substituted by G; wherein the groups $A^5$, $A^6$, $A^7$ and $A^8$ may be interrupted by one, or more groups —$(SiR^{17}R^{18})$—;

$R^{10}$ and $R^{11}$ are independently of each other a $C_6$-$C_{24}$aryl group, which can optionally be substituted by G; or a $C_2$-$C_{30}$heteroaryl group, which can optionally be substituted by G; or $R^{10}$ and $R^{11}$ together with the nitrogen atom to which they are bonded form a heteroaromatic ring, or ring system;

$R^{12}$, $R^{13}$ and $R^{14}$ are independently of each other a $C_1$-$C_{25}$alkyl group, which can optionally be substituted by E and or interrupted by D; $C_6$-$C_{24}$aryl group, which can optionally be substituted by G; or a $C_2$-$C_{30}$heteroaryl group, which can optionally be substituted by G;

$R^{15}$ is a $C_6$-$C_{24}$aryl group, which can optionally be substituted by G; or a $C_2$-$C_{30}$heteroaryl group, which can optionally be substituted by G;

$R^{16'}$ is a $C_6$-$C_{24}$aryl group, which can optionally be substituted by G; or a $C_2$-$C_{30}$heteroaryl group, which can optionally be substituted by G;

$R^{17}$ and $R^{18}$ are independently of each other a $C_1$-$C_{25}$alkyl group, or a $C_6$-$C_{24}$aryl group, which can optionally be substituted by one, or more $C_1$-$C_{25}$alkyl groups; D is —CO—, —COO—, —S—, —SO—, —$SO_2$—, —O—, —$NR^{65}$—, —$SiR^{70}R^{71}$—, —$POR^{72}$—, —$CR^{63}$=$CR^{64}$—, or —C≡C—, E is —$OR^{69}$, —$SR^{69}$, —$NR^{65}R^{66}$, —$COR^{68}$, —$COOR^{67}$, —$CONR^{65}R^{66}$, —CN, or halogen, G is E, or a $C_1$-$C_{18}$alkyl group, a $C_6$-$C_{24}$aryl group, a $C_6$-$C_{24}$aryl group, which is substituted by F, $C_1$-$C_{18}$alkyl, or $C_1$-$C_{18}$alkyl which is interrupted by O; a $C_2$-$C_{30}$heteroaryl group, or a $C_2$-$C_{30}$heteroaryl group, which is substituted by F, $C_1$-$C_{18}$alkyl, or $C_1$-$C_{18}$alkyl which is interrupted by O;

$R^{63}$ and $R^{64}$ are independently of each other H, $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{65}$ and $R^{66}$ are independently of each other a $C_6$-$C_{18}$aryl group; a $C_6$-$C_{18}$aryl which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—; or $R^{65}$ and $R^{66}$ together form a five or six membered ring, $R^{67}$ is a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{68}$ is H; a $C_6$-$C_{18}$aryl group; a $C_6$-$C_{18}$aryl group, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{69}$ is a $C_6$-$C_{18}$aryl; a $C_6$-$C_{18}$aryl, which is substituted by $C_1$-$C_{18}$alkyl, or $C_1$-$C_{18}$alkoxy; a $C_1$-$C_{18}$alkyl group; or a $C_1$-$C_{18}$alkyl group, which is interrupted by —O—, $R^{70}$ and $R^{71}$ are independently of each other a $C_1$-$C_{18}$alkyl group, a $C_6$-$C_{18}$aryl group, or a $C_6$-$C_{18}$aryl group, which is substituted by $C_1$-$C_{18}$alkyl, and $R^{72}$ is a $C_1$-$C_{18}$alkyl group, a $C_6$-$C_{18}$aryl group, or a $C_6$-$C_{18}$aryl group, which is substituted by $C_1$-$C_{18}$alkyl.

The compounds of the present invention may be used for electrophotographic photoreceptors, photoelectric converters, organic solar cells (organic photovoltaics), switching elements, such as organic transistors, for example, organic FETs and organic TFTs, organic light emitting field effect transistors (OLEFETs), image sensors, dye lasers and electroluminescent devices, such as, for example, organic light-emitting diodes (OLEDs).

Accordingly, a further subject of the present invention is directed to an electronic device, comprising a compound according to the present invention. The electronic device is preferably an electroluminescent device.

The compounds of formula I can in principal be used in any layer of an EL device, but are preferably used as host, hole transport and electron blocking material. Particularly, the compounds of formula I are used as host material for blue light emitting phosphorescent emitters.

Hence, a further subject of the present invention is directed to an hole transport layer, comprising a compound of formula I according to the present invention.

A further subject of the present invention is directed to an emitting layer, comprising a compound of formula I according to the present invention. In said embodiment a compound of formula I is preferably used as host material in combination with a phosphorescent emitter.

The compounds of formula I have preferably a molecular weight below 1500 g/mol.

A further subject of the present invention is directed to an electron blocking layer, comprising a compound of formula I according to the present invention.

$R^1$, $R^2$, $R^3$, $R^4$, $R^5$, $R^6$ and $R^7$ are preferably H. Accordingly, compounds of formula

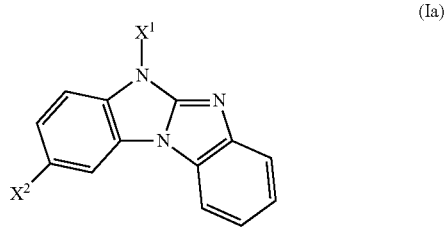

(Ia)

are preferred, wherein $X^1$ and $X^2$ are as defined above.

$R^{15}$ and $R^{16'}$($R^{16}$) may be a $C_6$-$C_{24}$aryl group, which can optionally be substituted by G, or a $C_2$-$C_{30}$heteroaryl group, which can optionally be substituted by G. If $R^{16'}$ represents a heteroaryl group, which is directly bonded to the benzimidazo[1,2-a]benzimidazole skeleton (o=p=q=r=0), $R^{16'}$ is preferably bonded via a carbon atom of the heteroaryl group to the benzimidazo[1,2-a]benzimidazole skeleton.

The $C_6$-$C_{24}$aryl groups $R^{15}$ and $R^{16'}$, which optionally can be substituted by G, are typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted.

The $C_2$-$C_{30}$heteroaryl group groups $R^{15}$ and $R^{16'}$, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated n-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, benzimidazo[1,2-a]benzimidazo-5-yl, benzimidazo[1,2-a]benzimidazo-2-yl, carbazolyl, or phenoxazinyl, which can be unsubstituted or substituted.

The $C_6$-$C_{24}$aryl and $C_2$-$C_{30}$heteroaryl groups may be substituted by G.

Prefered $C_2$-$C_{30}$heteroaryl groups are pyridyl, triazinyl, pyrimidinyl, benzimidazo[1,2-a]benzimidazo-5-yl

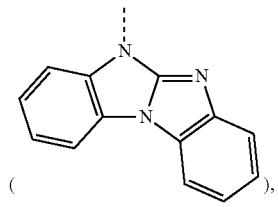

( ), benzimidazo[1,2-a]benzimidazo-2-yl

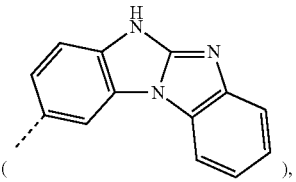

( ), carbazolyl, dibenzofuranyl, which can be unsubstituted or substituted especially by $C_6$-$C_{10}$aryl, or $C_6$-$C_{10}$aryl, which is substituted by $C_1$-$C_4$alkyl; or $C_2$-$C_{14}$heteroaryl.

$A^1$, $A^2$, $A^3$, $A^4$, $A^5$, $A^6$, $A^7$ and $A^8$ are independently of each other a $C_6$-$C_{24}$arylen group, which can optionally be substituted by G, or a $C_2$-$C_{30}$heteroarylen group, which can optionally be substituted by G. The $C_6$-$C_{24}$arylen groups $A^1$, $A^2$, $A^3$, $A^4$, $A^5$, $A^6$, $A^7$ and $A^8$, which optionally can be substituted by G, are typically phenylene, 4-methylphenylene, 4-methoxyphenylene, naphthylene, especially 1-naphthylene, or 2-naphthylene, biphenylylene, terphenylylene, pyrenylene, 2- or 9-fluorenylene, phenanthrylene, or anthrylene, which may be unsubstituted or substituted.

The $C_2$-$C_{30}$heteroarylen groups $A^1$, $A^2$, $A^3$, $A^4$ $A^5$, $A^6$, $A^7$ and $A^8$, which optionally can be substituted by G, represent a ring with five to seven ring atoms or a condensed ring system, wherein nitrogen, oxygen or sulfur are the possible hetero atoms, and is typically a heterocyclic group with five to 30 atoms having at least six conjugated-electrons such as thienylene, benzothiophenylene, dibenzothiophenylene, thianthrenylene, furylene, furfurylene, 2H-pyranylene, benzofuranylene, isobenzofuranylene, dibenzofuranylene, phenoxythienylene, pyrrolylene, imidazolylene, pyrazolylene, pyridylene, bipyridylene, triazinylene, pyrimidinylene, pyrazinylene, pyridazinylene, indolizinylene, isoindolylene, indolylene, indazolylene, purinylene, quinolizinylene, chinolylene, isochinolylene, phthalazinylene, naphthyridinylene, chinoxalinylene, chinazolinylene, cinnolinylene, pteridinylene, carbolinylene, benzotriazolylene, benzoxazolylene, phenanthridinylene, acridinylene, pyrimidinylene, phenanthrolinylene, phenazinylene, isothiazolylene, phenothiazinylene, isoxazolylene, furazanylene, carbazolylene, benzimidazo[1,2-a]benzimidazo-2,5-ylene, or phenoxazinylene, which can be unsubstituted or substituted.

Preferred $C_6$-$C_{24}$arylen groups are 1,3-phenylene, 3,3'-biphenylylene, 3,3'-m-terphenylene, 2- or 9-fluorenylene, phenanthrylene, which may be unsubstituted or substituted.

Preferred $C_2$-$C_{30}$heteroarylen groups are pyridylene, triazinylene, pyrimidinylene, carbazolylene, dibenzofuranylene and benzimidazo[1,2-a]benzimidazo-2,5-ylene

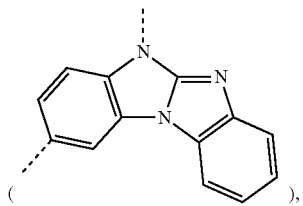

which can be unsubstituted or substituted, especially by $C_6$-$C_{10}$aryl, $C_6$-$C_{10}$aryl which is substituted by $C_1$-$C_4$alkyl; or $C_2$-$C_{14}$heteroaryl.

Benzimidazo[1,2-a]benzimidazo-5-yl, benzimidazo[1,2-a]benzimidazo-2-yl, carbazolyl and dibenzofuranyl are examples of a $C_2$-$C_{14}$heteroaryl group. Phenyl, 1-naphthyl and 2-naphthyl are examples of a $C_6$-$C_{10}$aryl group.

More preferred $C_2$-$C_{30}$heteroarylen groups are benzimidazo[1,2-a]benzimidazo-2,5-ylene, carbazolylene and dibenzofuranylene which optionally can be substituted by $C_6$-$C_{10}$aryl, which can optionally be substituted by one, or more $C_1$-$C_4$alkyl groups, or dibenzofuranyl.

The $C_6$-$C_{24}$arylen and $C_2$-$C_{30}$heteroarylen groups may be substituted by G.

$X^1$ is preferably a group of the formula -$A^1$-$(A^2)_p$-$(A^3)_q$-$(A^4)_r$—$R^{16}$, or -$(A^1)_o$-$(A^2)_p$-$(A^3)_q$$(A^4)_r$—$R^{16'}$, o is 0, or 1, p is 0, or 1, q is 0, or 1, r is 0, or 1, $A^1$, $A^2$, $A^3$ and $A^4$ are independently of each other a group of the formula

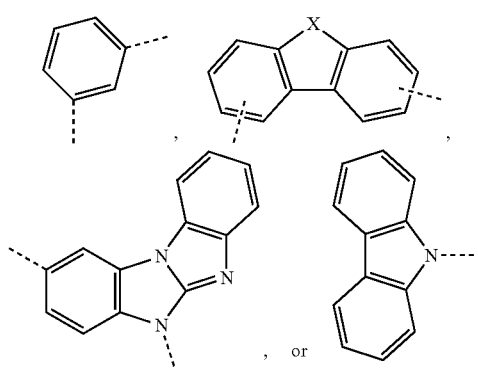

$R^{16}$ is a group of the formula

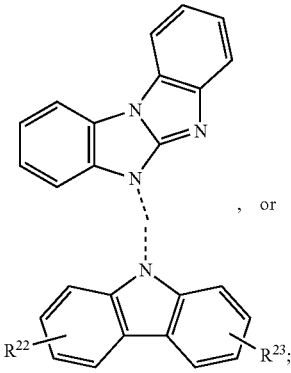

$R^{16'}$ is a group of the formula

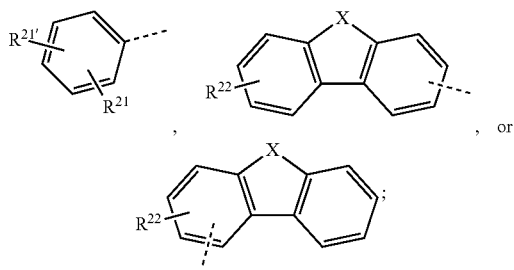

$R^{21}$ and $R^{21'}$ are independently of each other H, a phenyl group, or a $C_1$-$C_{18}$alkyl group;

$R^{22}$ and $R^{23}$ are independently of each other H, or a group of the formula

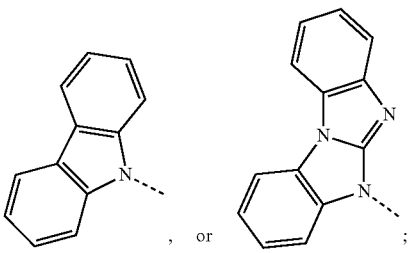

X is O, S, or $NR^{24}$, and $R^{24}$ is a $C_6$-$C_{24}$aryl group, or a $C_2$-$C_{30}$heteroaryl group, which can optionally be substituted by G, wherein G is as defined in claim 1.

More preferred, $X^1$ is a group of the formula -$A^1$-$(A^2)_p$-$(A^3)_q$-$(A^4)_r$—$R^{16}$, or -$(A^1)_o$-$(A^2)_p$-$(A^3)_q$$(A^4)_r$—$R^{16'}$, o is 0, or 1, p is 0, or 1, q is 0, or 1, r is 0, or 1, $A^1$, $A^2$, $A^3$ and $A^4$ are independently of each other a group of the formula

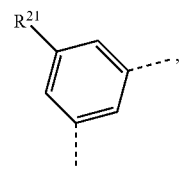

especially
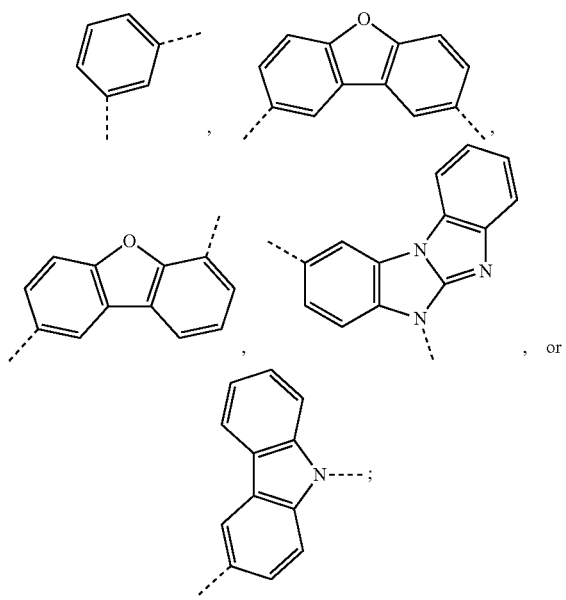
$R^{16}$ is a group of the formula
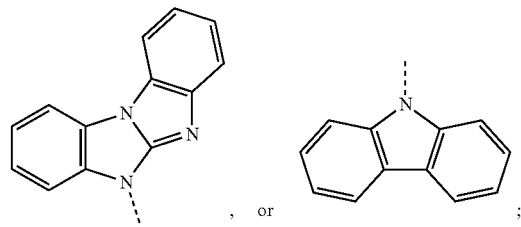
$R^{16'}$ is a group of the formula
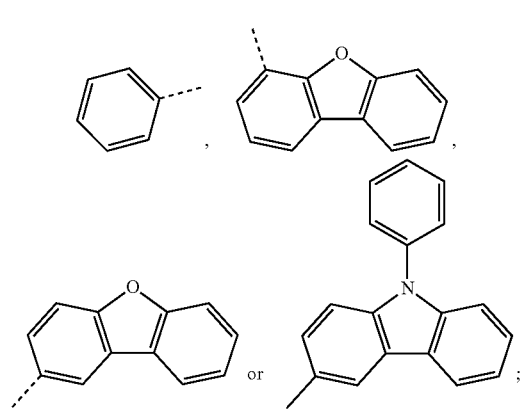
and $R^{21}$ is a group of the formula
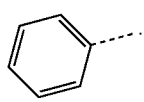
Most preferred $X^1$ is a group of the formula
especially
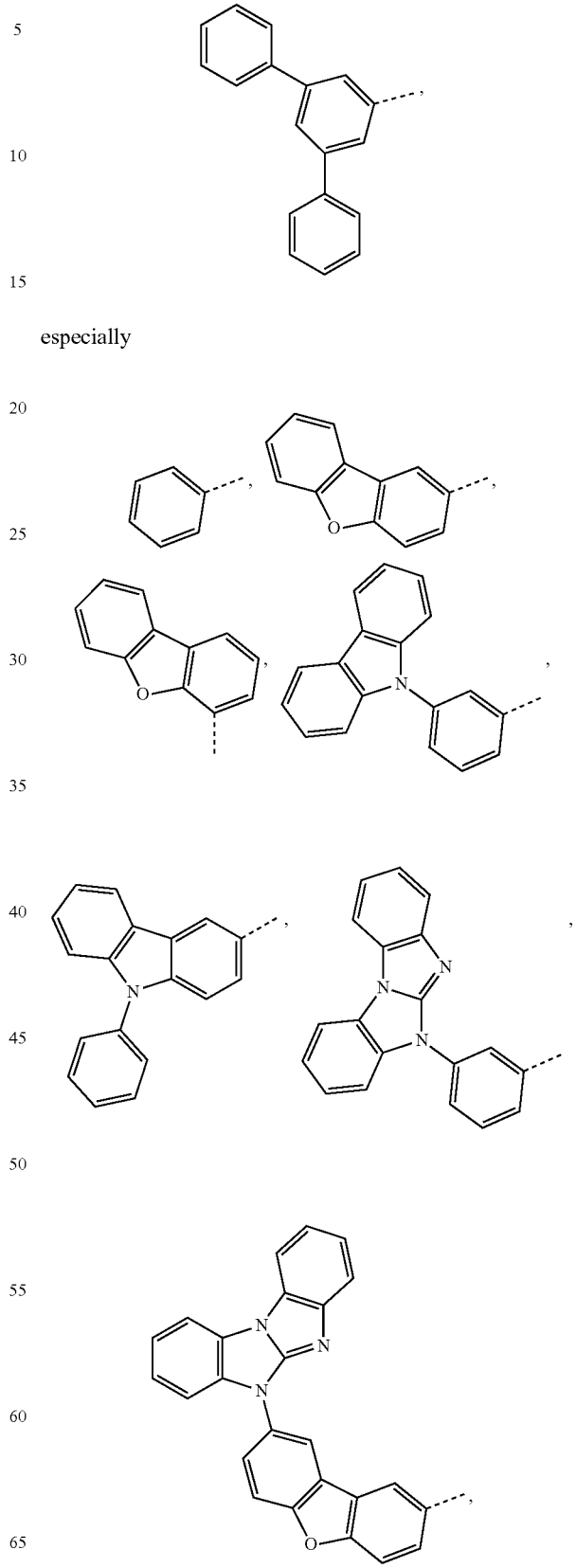

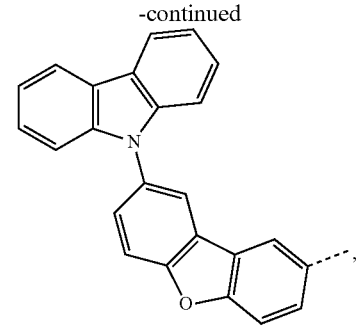
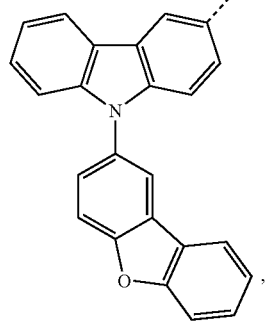
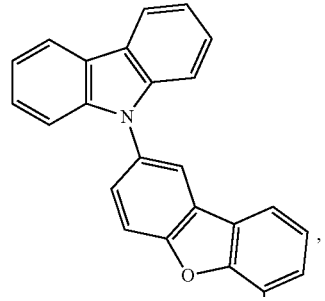
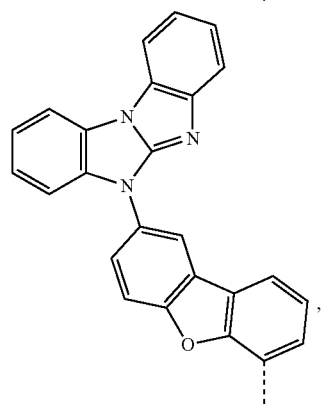
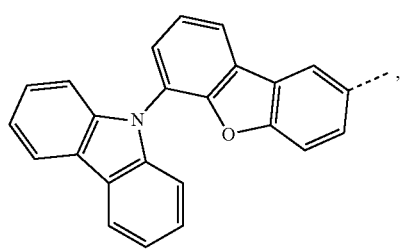
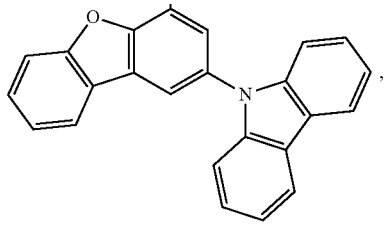
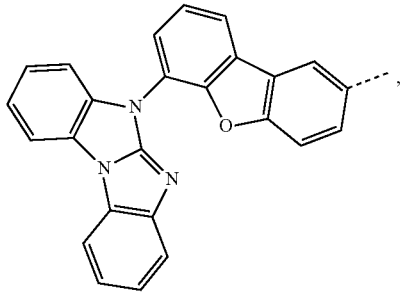
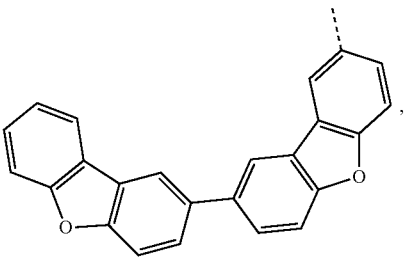
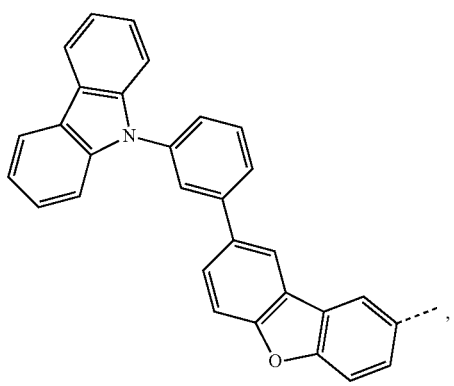
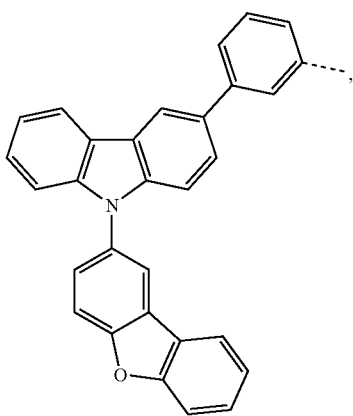

23
-continued
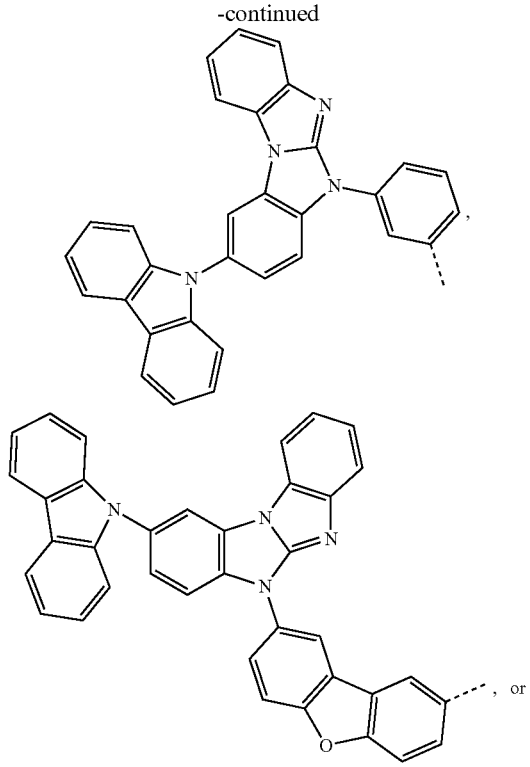
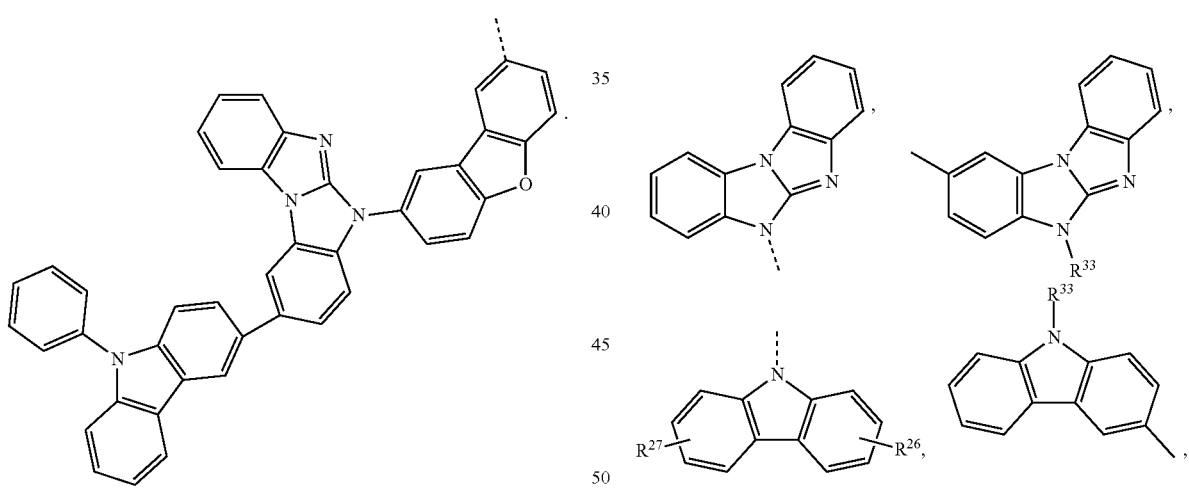
$X^2$ is preferably a group of formula -$(A^5)_v$-$(A^6)_s$-$(A^7)_t$-$(A^8)_u$—R$_{15}$,
v is 0, or 1, s is 0, or 1, t is 0, or 1, u is 0, or 1,
$A^5$, $A^6$, $A^7$ and $A^8$ are independently of each other
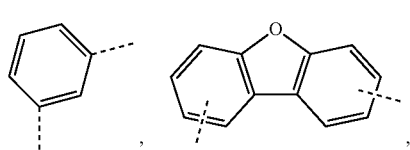
24
-continued
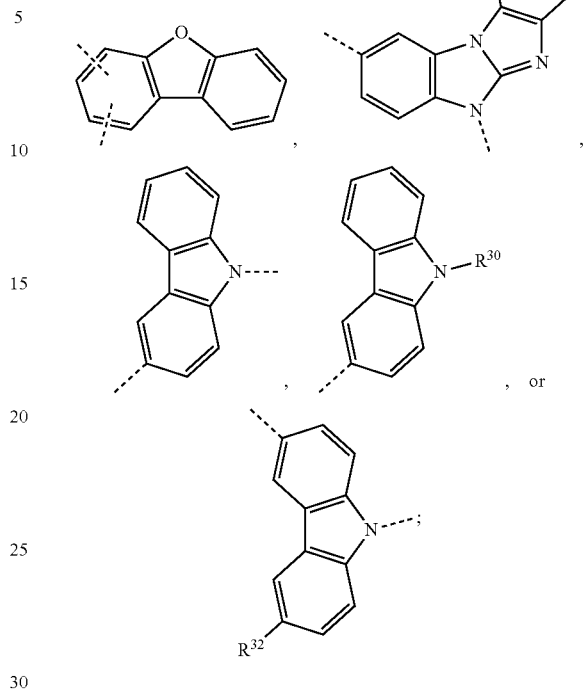
$R^{15}$ is a group of the formula
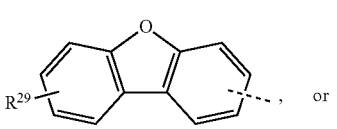
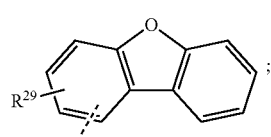

$R^{26}$, $R^{27}$, $R^{29}$ and $R^{32}$ are independently of each other H, or a group of the formula

[chemical structures: carbazole and benzimidazole groups]

$R^{30}$ and $R^{33}$ are independently of each other a group of formula

[chemical structures: phenyl, dibenzofuran groups]

[chemical structures: dibenzofuran, benzimidazole with $R^{31}$];

and $R^{31}$ is a group of formula

[chemical structures: phenyl, dibenzofuran]

[chemical structure: dibenzofuran]

More preferred $X^2$ is a group of formula $-(A^5)_v-(A^6)_s-(A^7)_t-(A^8)_u-R^{15}$, v is 0, or 1, s is 0, or 1, t is 0, or 1, u is 0, or 1, $A^5$, $A^6$, $A^7$ and $A^8$ are independently of each other

[chemical structures: phenyl, dibenzofuran]

-continued

[chemical structures: dibenzofuran groups]

[chemical structure: benzimidazole]

[chemical structures: carbazole, N-phenyl carbazole]

[chemical structure: extended carbazole-carbazole]

[chemical structure: carbazole-benzimidazole fused system];

$R^{15}$ is a group of the formula
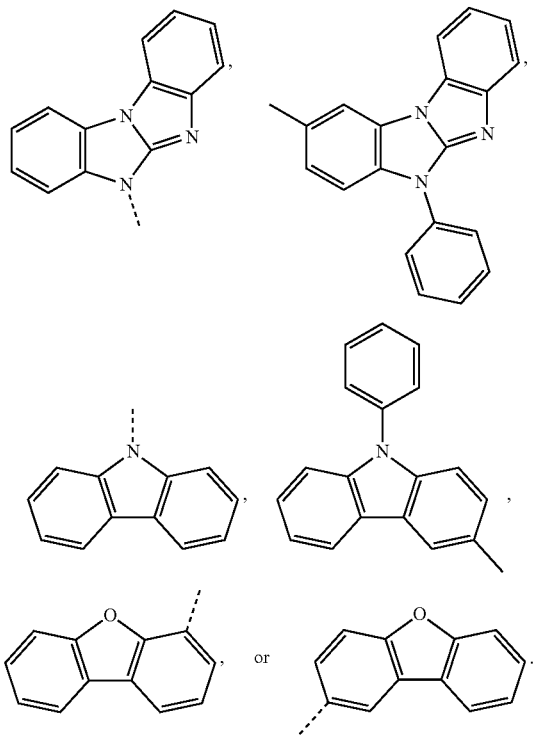
An example of $X^2$ is a group of formula
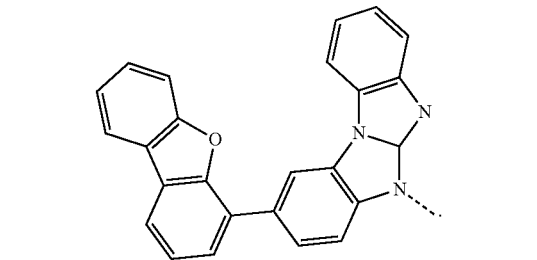
Most preferred $X^2$ is a group of formula
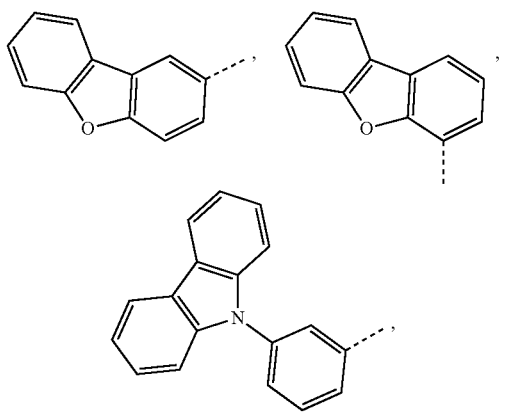
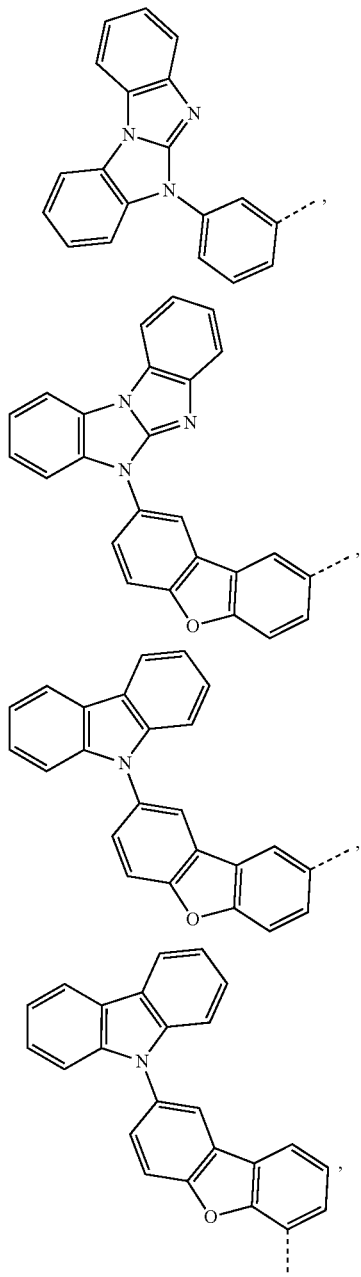
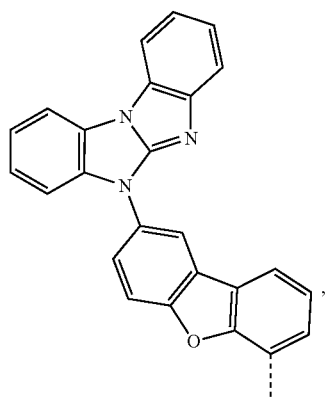

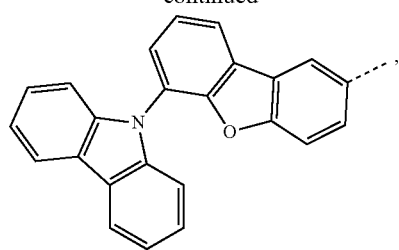
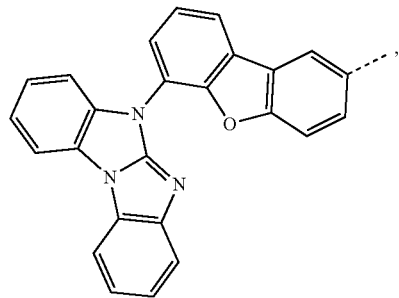
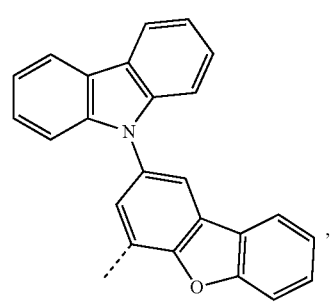
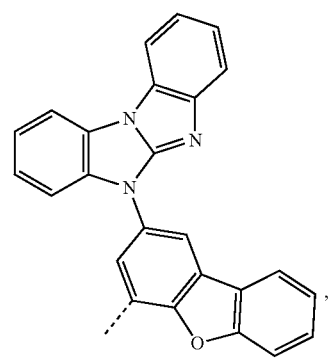
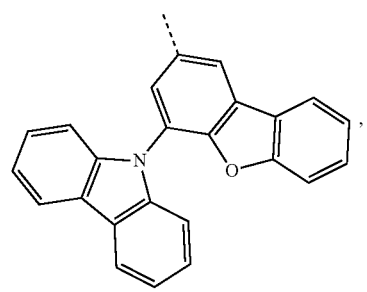
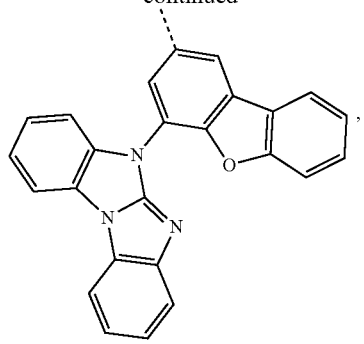
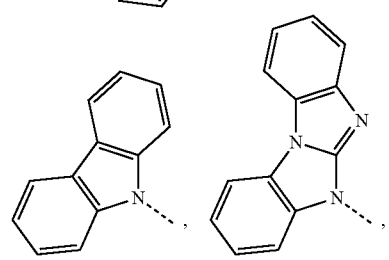
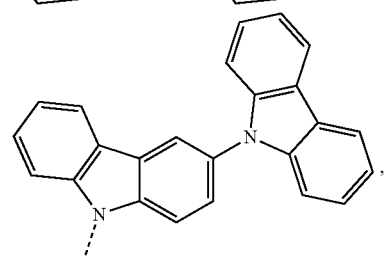
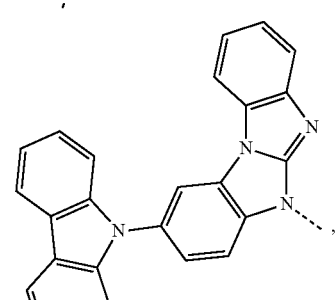
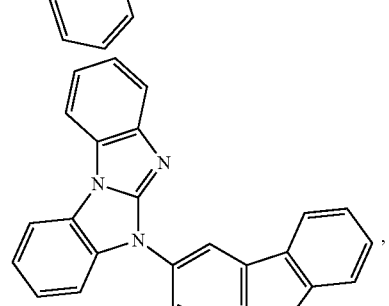
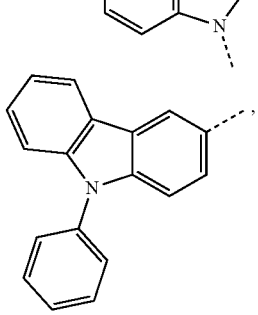

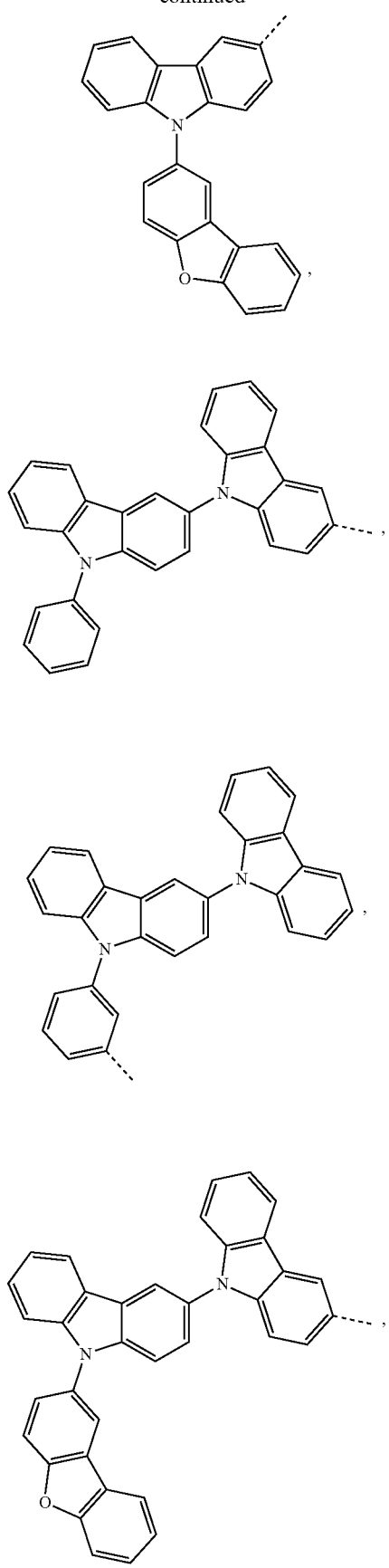
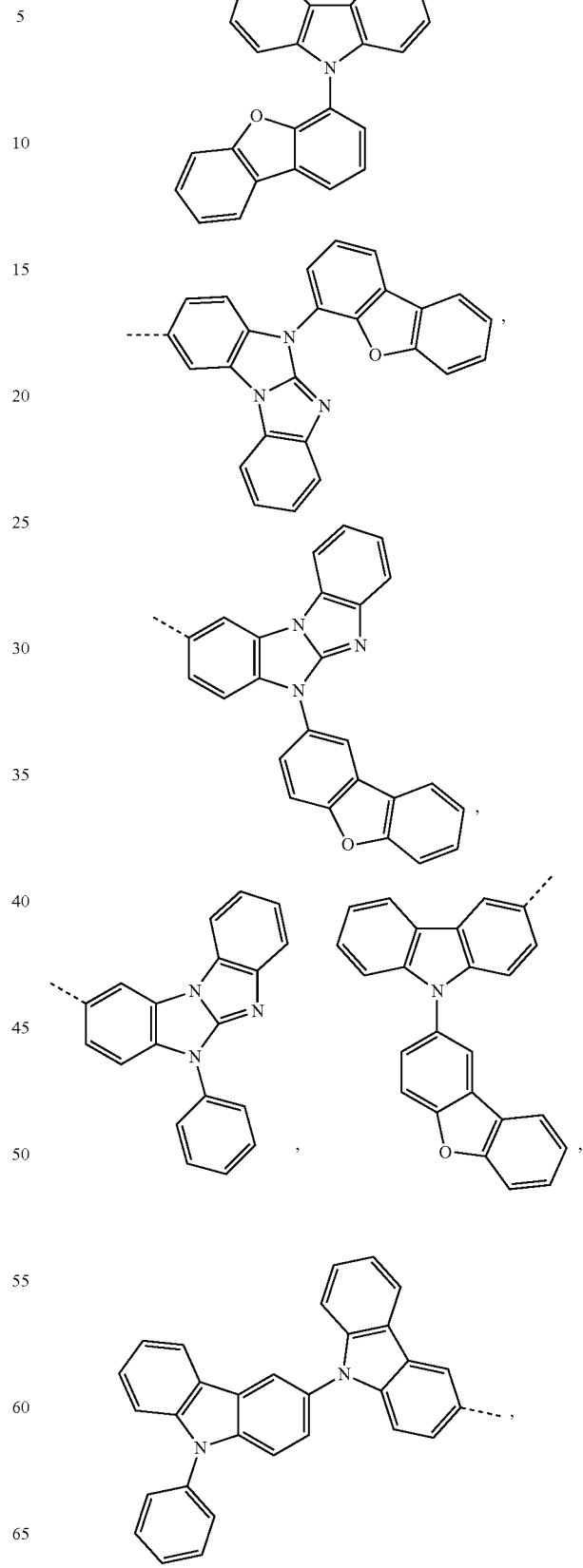

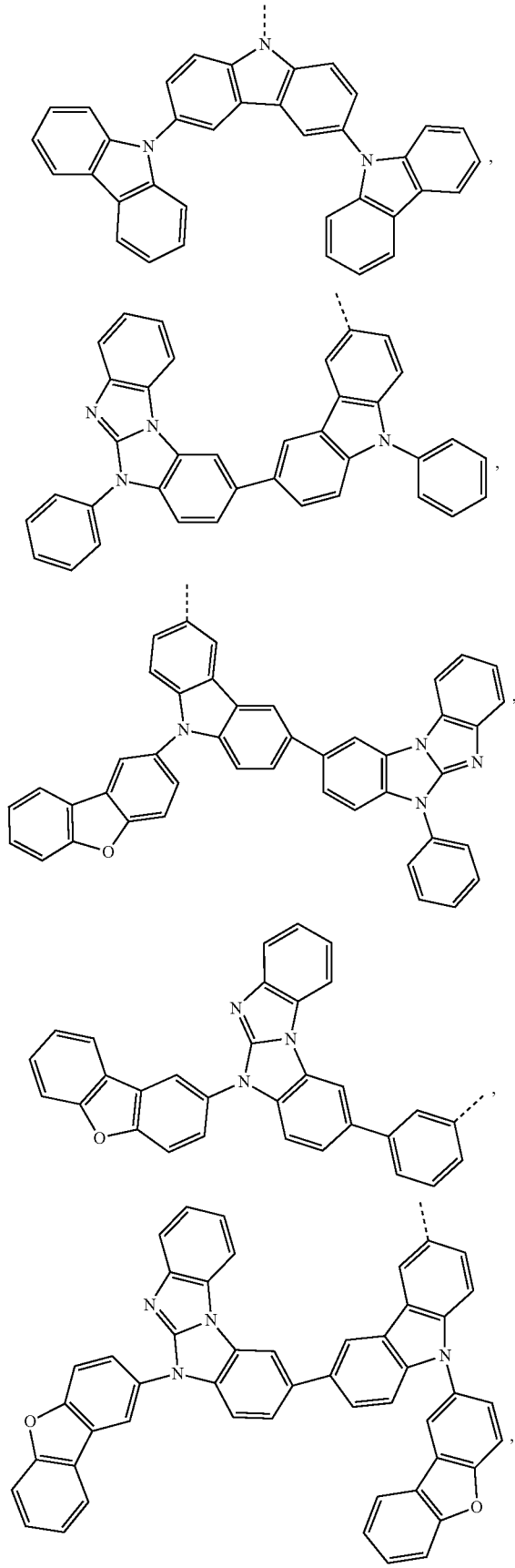

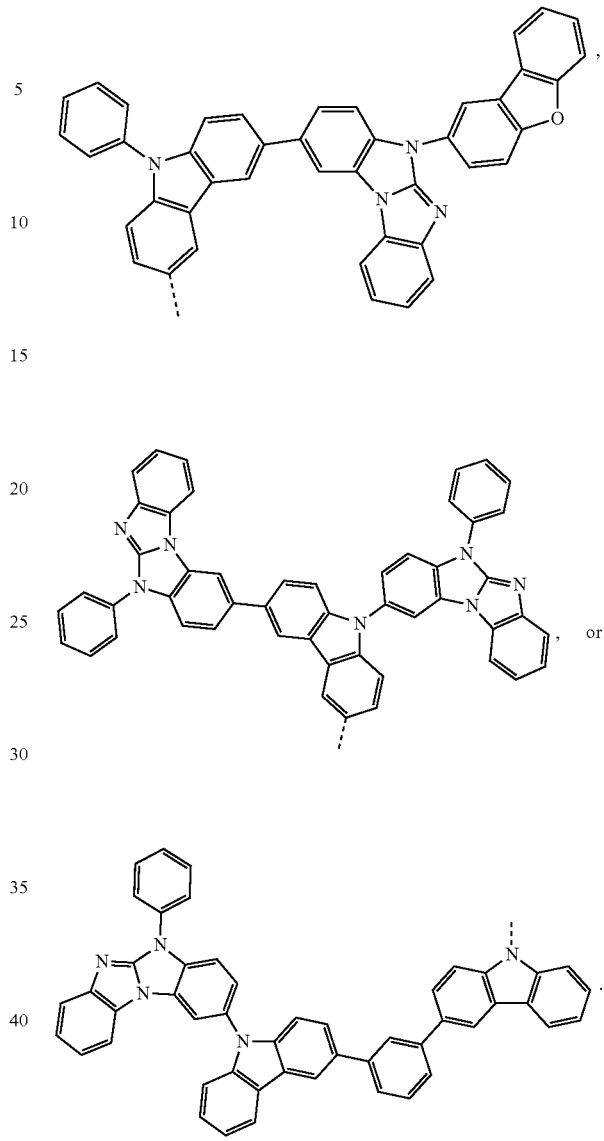

Compounds of formula (Ia) are preferred, where $X^1$ and $X^2$ have the preferred meanings given above. Compounds of formula (Ia) are more preferred, where $X^1$ and $X^2$ have the more preferred meanings given above. Compounds of formula (Ia) are most preferred, where $X^1$ and $X^2$ have the most preferred meanings given above.

In another preferred embodiment the present invention is directed to compounds of formula (Ia), comprising two groups

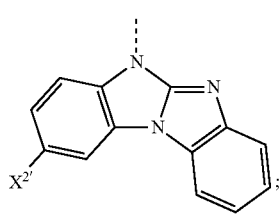

i.e compounds of formula

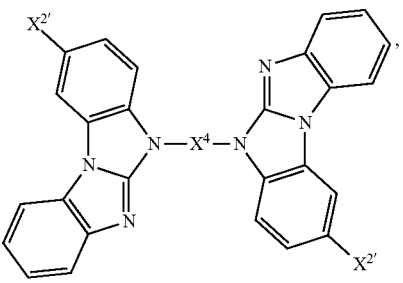

wherein $X^{2'}$ is a group of the formula $-(A^8)_u-R^{15}$, $-NR^{10}R^{11}$, or $Si(R^{12})(R^{13})(R^{14})$, $X^4$ is a group of formula $A^1-(A^2)_p-$, and p, u, $A^1$, $A^2$, $A^8$, $R^{10}$, $R^{11}$, $R^{12}$, $R^{13}$, $R^{14}$ and $R^{15}$ are as defined above. The groups $X^{2'}$ may be different, but are preferably the same. With respect to p, u, $A^1$, $A^2$, $A^8$, $R^{10}$, $R^{11}$, $R^{12}$, $R^{13}$, $R^{14}$ and $R^{15}$ the same preferences apply as with respect to the compounds of formula (I) and (Ia), respectively.

In another preferred embodiment the present invention is directed to compounds of formula (Ia), comprising two groups

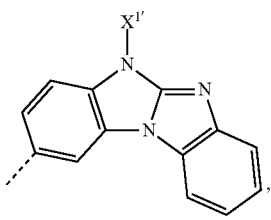

i.e compounds of formula

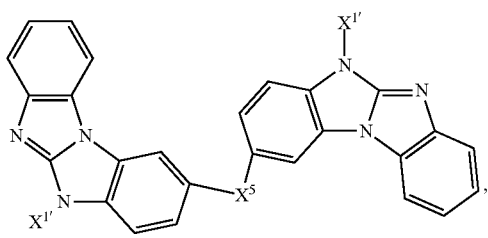

wherein $X^{1'}$ is a group of formula $-A^1-R^{16}$, or $-(A^4)_r-R^{16'}$; $X^5$ is a group of formula $-A^5-(A^6)_s-$, and r, s, $A^1$, $R^{16}$, $A^4$, $R^{16'}$, $A^5$ and $A^6$ are as defined above. The groups $X^{1'}$ may be different, but are preferably the same. With respect to r, s, $A^1$, $R^{16}$, $A^4$, $R^{16'}$, $A^5$ and $A^6$ the same preferences apply as with respect to the compounds of formula (I) and (Ia), respectively.

Examples of especially preferred compounds are compounds A-1 to A-45 shown in claim 8, which are particularly suitable as host and hole transport material. Compounds A-1, A-2, A-9, A-10, A-11, A-24, A-42, A-43, A-44 and A-45 are most preferred. Additional examples of preferred compounds are compounds A-46 to A-51 shown in claim 8.

Halogen is fluorine, chlorine, bromine and iodine.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, or octadecyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy groups ($C_1$-$C_{18}$alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentyloxy, 2-pentyloxy, 3-pentyloxy, 2,2-dimethylpropoxy, n-hexyloxy, n-heptyloxy, n-octyloxy, 1,1,3,3-tetramethylbutoxy and 2-ethylhexyloxy, preferably $C_1$-$C_4$alkoxy such as typically methoxy, ethoxy, n-propoxy, isopropoxy, n-butoxy, sec.-butoxy, isobutoxy, tert.-butoxy.

The term "cycloalkyl group" is typically $C_4$-$C_{18}$cycloalkyl, especially $C_5$-$C_{12}$cycloalkyl, such as cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted.

$C_6$-$C_{24}$aryl ($C_6$-$C_{18}$aryl), which optionally can be substituted, is typically phenyl, 4-methylphenyl, 4-methoxyphenyl, naphthyl, especially 1-naphthyl, or 2-naphthyl, biphenylyl, terphenylyl, pyrenyl, 2- or 9-fluorenyl, phenanthryl, or anthryl, which may be unsubstituted or substituted.

$C_2$-$C_{30}$heteroaryl represents a ring with five to seven ring atoms or a condensed ring system, wherein nitrogen, oxygen or sulfur are the possible hetero atoms, and is typically a heterocyclic group with five to 30 atoms having at least six conjugated i-electrons such as thienyl, benzothiophenyl, dibenzothiophenyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl, 4-imidazo[1,2-a]benzimidazoyl, 5-benzimidazo[1,2-a]benzimidazoyl, carbazolyl, or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, or a cyano group. The $C_6$-$C_{24}$aryl ($C_6$-$C_{18}$aryl) and $C_2$-$C_{30}$heteroaryl groups are preferably substituted by one, or more $C_1$-$C_8$alkyl groups.

If a substituent occurs more than one time in a group, it can be different in each occurrence. The wording "substituted by G" means that one, or more, especially one to three substituents G might be present.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$) $C_4H_9$), $CH_2$—CH($OR^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H; $C_1$-$C_8$alkylene-COO—$R^z$, e.g. $CH_2COOR_z$, $CH(CH_3)CO$-$OR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above;

$CH_2CH_2$—O—CO—CH=$CH_2$; $CH_2CH(OH)CH_2$—O—CO—C($CH_3$)=$CH_2$.

The synthesis of

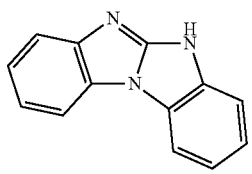 [SMILES: c1ccc2c(c1)nc1[nH]c3ccccc3n12]

is described, for example, in Achour, Reddouane; Zniber, Rachid, Bulletin des Societes Chimiques Belges 96 (1987) 787-92.

Suitable base skeletons of the formula

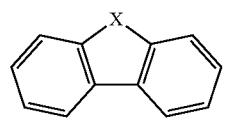

are either commercially available (especially in the cases when X is S, O, NH), or can be obtained by processes known to those skilled in the art. Reference is made to WO2010079051 and EP1885818.

The halogenation can be performed by methods known to those skilled in the art. Preference is given to brominating or iodinating in the 3 and 6 positions (dibromination) or in the 3 or 6 positions (monobromination) of the base skeleton of the formula (II) 2,8 positions (dibenzofuran and dibenzothiophene) or 3,6 positions (carbazole).

Optionally substituted dibenzofurans, dibenzothiophenes and carbazoles can be dibrominated in the 2,8 positions (dibenzofuran and dibenzothiophene) or 3,6 positions (carbazole) with bromine or NBS in glacial acetic acid or in chloroform. For example, the bromination with $Br_2$ can be effected in glacial acetic acid or chloroform at low temperatures, e.g. 0° C. Suitable processes are described, for example, in M. Park, J. R. Buck, C. J. Rizzo, Tetrahedron, 54 (1998) 12707-12714 for X=NPh, and in W. Yang et al., J. Mater. Chem. 13 (2003) 1351 for X=S. In addition, 3,6-dibromocarbazole, 3,6-dibromo-9-phenylcarbazole, 2,8-dibromodibenzothiophene, 2,8-dibromodibenzofuran, 2-bromocarbazole, 3-bromodibenzothiophene, 3-bromodibenzofuran, 3-bromocarbazole, 2-bromodibenzothiophene and 2-bromodibenzofuran are commercially available.

Monobromination in the 4 position of dibenzofuran (and analogously for dibenzothiophene) is described, for example, in J. Am. Chem. Soc. 1984, 106, 7150. Dibenzofuran (dibenzothiophene) can be monobrominated in the 3 position by a sequence known to those skilled in the art, comprising a nitration, reduction and subsequent Sandmeyer reaction.

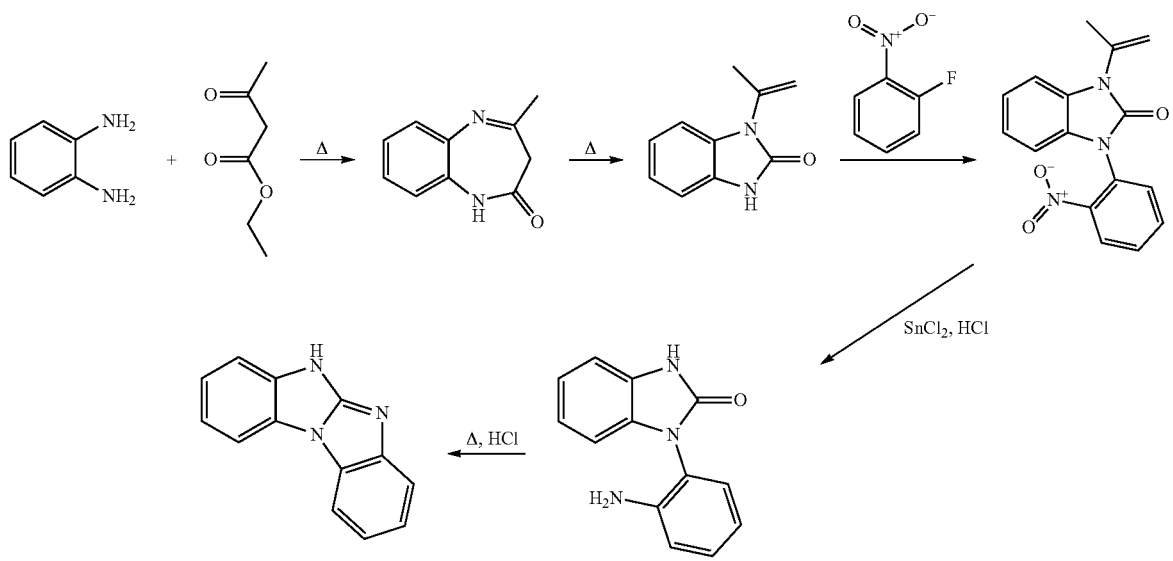

Monobromination in the 2 position of dibenzofuran or dibenzothiophene and monobromination in the 3 position of carbazole are effected analogously to the dibromination, with the exception that only one equivalent of bromine or NBS is added.

Alternatively, it is also possible to utilize iodinated dibenzofurans, dibenzothiophenes and carbazoles. The preparation is described, inter alia, in Tetrahedron. Lett. 47 (2006) 6957-6960, Eur. J. Inorg. Chem. 24 (2005) 4976-4984, J.

Heterocyclic Chem. 39 (2002) 933-941, J. Am. Chem. Soc. 124 (2002) 11900-11907, J. Heterocyclic Chem, 38 (2001) 77-87.

For the nucleophilic substitution, Cl- or F-substituted dibenzofurans, dibenzothiophenes and carbazoles are required. The chlorination is described, inter alia, in J. Heterocyclic Chemistry, 34 (1997) 891-900, Org. Lett., 6 (2004) 3501-3504; J. Chem. Soc. [Section] C: Organic, 16 (1971) 2775-7, Tetrahedron Left. 25 (1984) 5363-6, J. Org. Chem. 69 (2004) 8177-8182. The fluorination is described in J. Org. Chem. 63 (1998) 878-880 and J. Chem. Soc., Perkin Trans. 2, 5 (2002) 953-957.

The introduction of the group

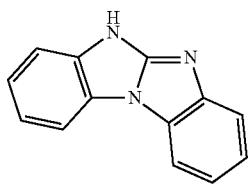 [SMILES: c1ccc2c(c1)nc1[nH]c3ccccc3n12]

is performed in the presence of a base. Suitable bases are known to those skilled in the art and are preferably selected from the group consisting of alkali metal and alkaline earth metal hydroxides such as NaOH, KOH, Ca(OH)$_2$, alkali metal hydrides such as NaH, KH, alkali metal amides such as NaNH$_2$, alkali metal or alkaline earth metal carbonates such as K$_2$CO$_3$ or Cs$_2$CO$_3$, and alkali metal alkoxides such as NaOMe, NaOEt. In addition, mixtures of the aforementioned bases are suitable. Particular preference is given to NaOH, KOH, NaH or K$_2$CO$_3$.

Heteroarylation can be effected, for example, by copper-catalyzed coupling of

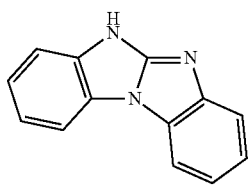 [SMILES: c1ccc2c(c1)nc1[nH]c3ccccc3n12]

to a halogenated compound of the formula

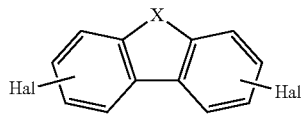

(Ullmann reaction).

The N-arylation was, for example, disclosed in H. Gilman and D. A. Shirley, J. Am. Chem. Soc. 66 (1944) 888; D. Li et al., Dyes and Pigments 49 (2001) 181-186 and Eur. J. Org. Chem. (2007) 2147-2151. The reaction can be performed in solvent or in a melt. Suitable solvents are, for example, (polar) aprotic solvents such as dimethyl sulfoxide, dimethylformamide, NMP, tridecane or alcohols.

The synthesis of 9-(8-bromodibenzofuran-2-yl)carbazole,

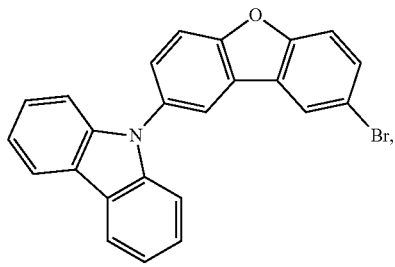 [SMILES: Brc1ccc2oc3ccc(-n4c5ccccc5c5ccccc54)cc3c2c1]

is described in WO2010079051. The synthesis of 2-bromo-8-iodo-dibenzofurane,

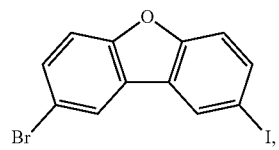 [SMILES: Brc1ccc2oc3ccc(I)cc3c2c1]

is described in EP1885818.

A possible synthesis route for the compound of formula

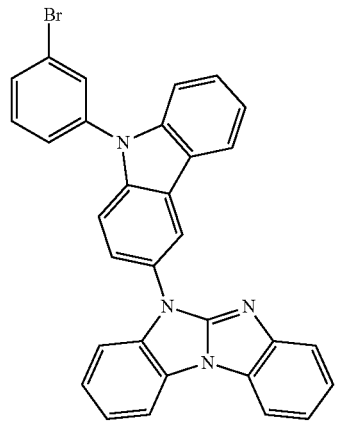 [SMILES: Brc1cccc(-n2c3ccccc3c3cc(-n4c5ccccc5n5c6ccccc6nc45)ccc32)c1]

is shown in the following scheme:

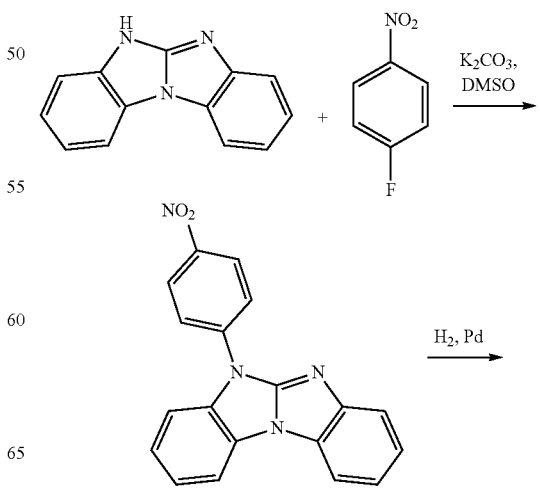

-continued

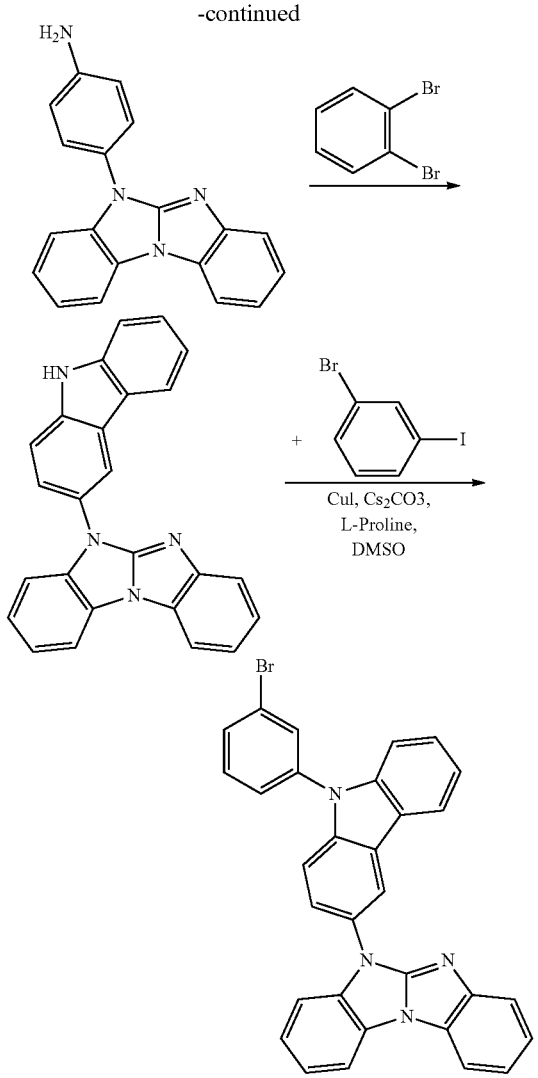

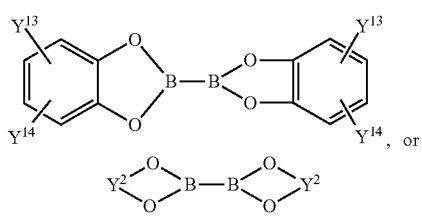

Reference is made to Angew. Chem. Int. Ed. 46 (2007) 1627-1629 and Synthesis 20 (2009) 3493.

Diboronic acid or diboronate group containing dibenzofurans, dibenzothiophenes and carbazoles can be readily prepared by an increasing number of routes. An overview of the synthetic routes is, for example, given in Angew. Chem. Int. Ed. 48 (2009) 9240-9261.

By one common route diboronic acid or diboronate group containing dibenzofurans, dibenzothiophenes, and carbazoles can be obtained by reacting halogenated dibenzofurans, dibenzothiophenes and carbazoles with $(Y^1O)_2B$—$B(OY^1)_2$,

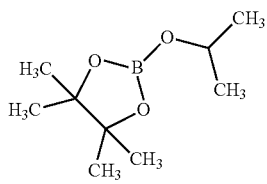

in the presence of a catalyst, such as, for example, [1,1'-bis(diphenylphosphino)ferrocene]dichloropalladium(II), complex $(Pd(Cl)_2(dppf))$, and a base, such as, for example, potassium acetate, in a solvent, such as, for example, dimethyl formamide, dimethyl sulfoxide, dioxane and/or toluene (cf. Prasad Appukkuttan et al., Synlett 8 (2003) 1204), wherein $Y^1$ is independently in each occurrence a $C_1$-$C_{18}$alkylgroup and $Y^2$ is independently in each occurrence a $C_2$-$C_{10}$alkylene group, such as —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{18}$alkylgroup, especially —$C(CH_3)_2C(CH_3)_2$—, —$C(CH_3)_2CH_2C(CH_3)_2$—, or —$CH_2C(CH_3)_2CH_2$—, and $Y^{13}$ and $Y^{14}$ are independently of each other hydrogen, or a $C_1$-$C_{18}$alkylgroup.

Diboronic acid or diboronate group containing dibenzofurans, dibenzothiophenes and carbazoles can also be prepared by reacting halogenated dibenzofurans, dibenzothiophenes and carbazoles with alkyl lithium reagents, such as, for example, n-butyl lithium, or t-buthyl lithium, followed by reaction with boronic esters, such as, for example, B(isopropoxy)$_3$, B(methoxy)$_3$, or

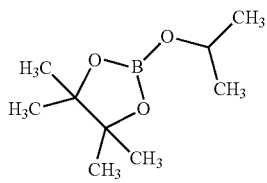

(cf. Synthesis (2000) 442-446).

Diboronic acid or diboronate group containing dibenzofurans, dibenzothiophenes and carbazoles can also be prepared by reacting dibenzofurans, dibenzothiophenes and carbazoles with lithium amides, such as, for example, lithium diisopropylamide (LDA) followed by reaction with boronic esters such as, for example, B(isopropoxy)$_3$, B(methoxy)$_3$, or

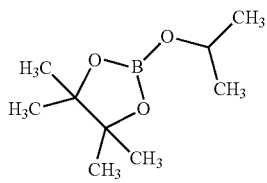

(J. Org. Chem. 73 (2008) 2176-2181).

Diboronic acid or diboronate group containing dibenzofurans, dibenzothiophenes and carbazoles, such as, for example,

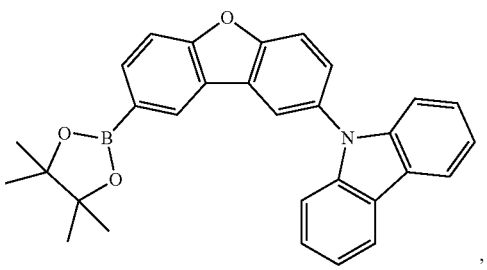 [SMILES: CC1(C)OB(c2ccc3oc4ccc(-n5c6ccccc6c6ccccc65)cc4c3c2)OC1(C)C]

can be reacted with equimolar amounts of halogenated dibenzofurans, dibenzothiophenes, carbazoles and 4H-imidazo[1,2-a]imidazoles, such as, for example,

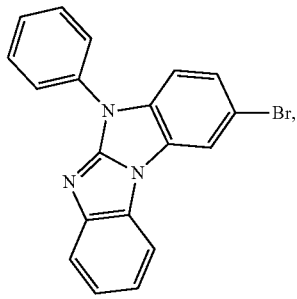 [SMILES: Brc1ccc2c(c1)n1c3ccccc3nc1n2-c1ccccc1]

in a solvent and in the presence of a catalyst. The catalyst may be one of the μ-halo(triisopropylphosphine)(η³-allyl) palladium(II) type (see for example WO99/47474).

Preferably, the Suzuki reaction is carried out in the presence of an organic solvent, such as an aromatic hydrocarbon or a usual polar organic solvent, such as benzene, toluene, xylene, tetrahydrofurane, or dioxane, or mixtures thereof, most preferred toluene. Usually, the amount of the solvent is chosen in the range of from 1 to 10 l per mol of boronic acid derivative. Also preferred, the reaction is carried out under an inert atmosphere such as nitrogen, or argon. Further, it is preferred to carry out the reaction in the presence of an aqueous base, such as an alkali metal hydroxide or carbonate such as NaOH, KOH, Na₂CO₃, K₂CO₃, Cs₂CO₃ and the like, preferably an aqueous K₂CO₃ solution is chosen. Usually, the molar ratio of the base to boronic acid or boronic ester derivative is chosen in the range of from 0.5:1 to 50:1, very especially 1:1. Generally, the reaction temperature is chosen in the range of from 40 to 180° C., preferably under reflux conditions. Preferred, the reaction time is chosen in the range of from 1 to 80 hours, more preferably from 20 to 72 hours. In a preferred embodiment a usual catalyst for coupling reactions or for polycondensation reactions is used, preferably Pd-based, which is described in WO2007/101820. The palladium compound is added in a ratio of from 1:10000 to 1:50, preferably from 1:5000 to 1:200, based on the number of bonds to be closed. Preference is given, for example, to the use of palladium(II) salts such as PdAc₂ or Pd₂dba₃ and to the addition of ligands selected from the group consisting of

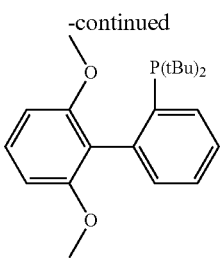

wherein

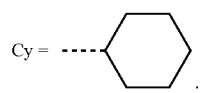

The ligand is added in a ratio of from 1:1 to 1:10, based on Pd. Also preferred, the catalyst is added as in solution or suspension. Preferably, an appropriate organic solvent such as the ones described above, preferably benzene, toluene, xylene, THF, dioxane, more preferably toluene, or mixtures thereof, is used. The amount of solvent usually is chosen in the range of from 1 to 10 l per mol of boronic acid derivative. Organic bases, such as, for example, tetraalkylammonium hydroxide, and phase transfer catalysts, such as, for example TBAB, can promote the activity of the boron (see, for example, Lead-beater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, G. Wegner in Macromol. Rapid Commun. 17 (1996) 239-252 and G. A. Molander und B. Canturk, Angew. Chem., 121 (2009) 9404-9425.

A possible synthetic route for compound A-42 is shown in the reaction scheme below:

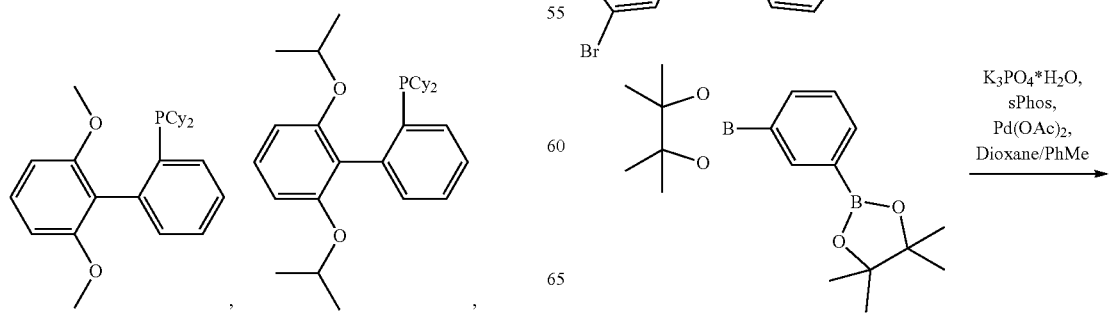

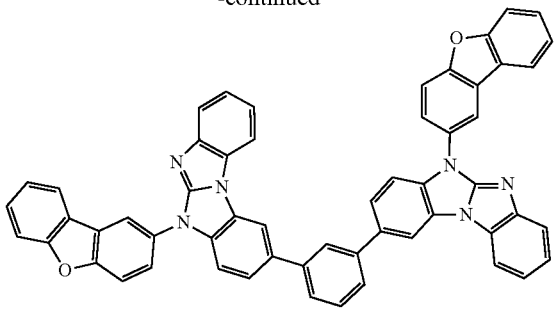

A possible synthetic route for compound B-1 is shown in the reaction scheme below:

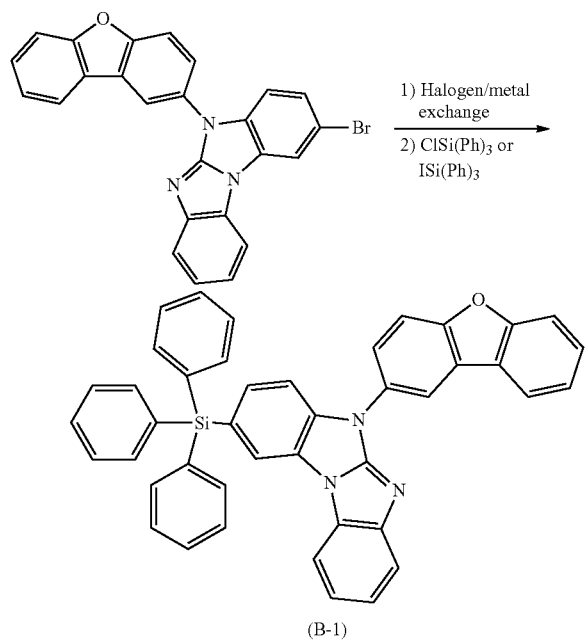

(B-1)

The halogen/metal exchange is done with nBuLi/THF at −78° C., or tBuLi/THF at −78° C. Reference is made to WO2010/079051, where the synthesis of such compounds is described.

Compounds of formula

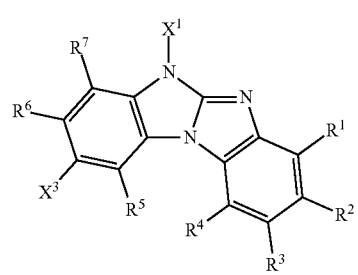

(II)

are new, intermediates in the production of compounds of formula (I) and form a further subject of the present invention.

$X^1$ is as defined above, or is a group of formula $A^1$-$(A^2)_p$-$(A^3)_q$-$(A^4)_r$—$R^{16''}$, $X^3$ is a group of formula -$(A^5)_v$-$(A^6)_s$-$(A^7)_t$-$(A^8)_u$—$R^{15'}$, wherein $R^{15'}$ and $R^{16''}$ are independently of each other Cl, Br, I, $ZnX^{12}$, $X^{12}$ is a halogen atom; —$SnR^{207}R^{206}R^{209}$, wherein $R^{207}$, $R^{208}$ and $R^{209}$ are identical or different and are H or $C_1$-$C_8$alkyl, wherein two radicals optionally form a common ring and these radicals are optionally branched or branched; —$B(OH)_2$, —$B(OY^1)_2$,

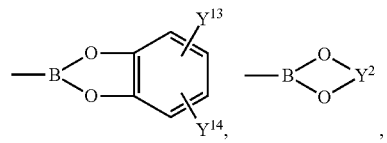

—$BF_4Na$, or —$BF_4K$, wherein $Y^1$ is independently in each occurrence a $C_1$-$C_{18}$alkyl group and $Y^2$ is independently in each occurrence a $C_2$-$C_{10}$alkylene group, such as —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially —$C(CH_3)_2C(CH_3)_2$—, —$C(CH_3)_2CH_2C(CH_3)_2$—, or —$CH_2C(CH_3)_2CH_2$—, and $Y^{13}$ and $Y^{14}$ are independently of each other hydrogen, or a $C_1$-$C_{10}$alkyl group.

p, q, r, $A^1$, $A^2$, $A^3$, $A^4$, s, t, u, v, $A^5$, $A^6$, $A^7$, $A^8$, $R^1$, $R^2$, $R^3$, $R^4$, $R^5$, $R^6$ and $R^7$ are as defined above. With respect to p, q, r, $A^1$, $A^2$, $A^3$, $A^4$, s, t, u, v, $A^5$, $A^6$, $A^7$, $A^8$, $R^1$, $R^2$, $R^3$, $R^4$, $R^5$, $R^6$, $R^7$ and $X^1$ the same preferences apply as for the compounds of formula (I).

Examples of the intermediates are shown below:

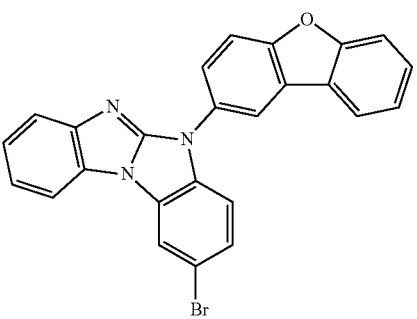

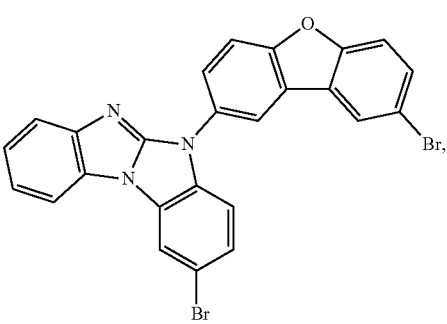

-continued

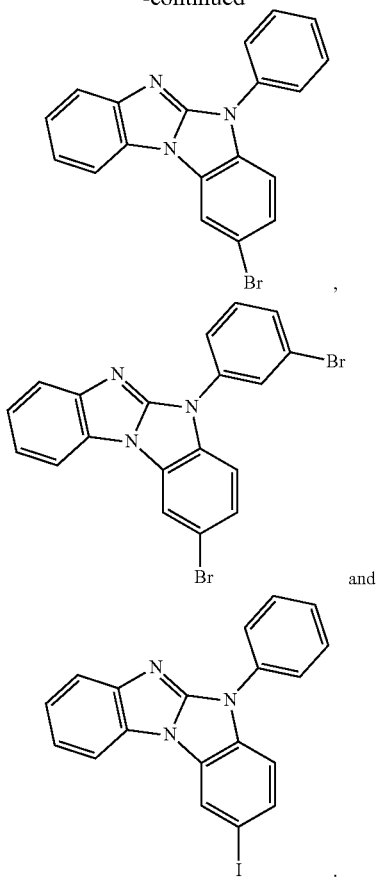

and

A process for the preparation of a compound of formula (II)

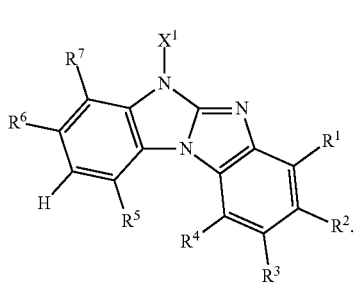

wherein $X^3$ is Cl, Br, or I; comprises halogenation of a compound of formula (III)

With respect to $R^1$, $R^2$, $R^3$, $R^4$, $R^5$, $R^6$, $R^7$ and $X^1$ the same preferences apply as with respect to the compounds of formula (I).

The bromination of 5-phenybenzimidazolo[1,2-a]benzimidazole can be carried out in analogy to the bromination of carbazole, which is, for example, described in J. Mater. Chem. 18 (2008) 1296-1301.

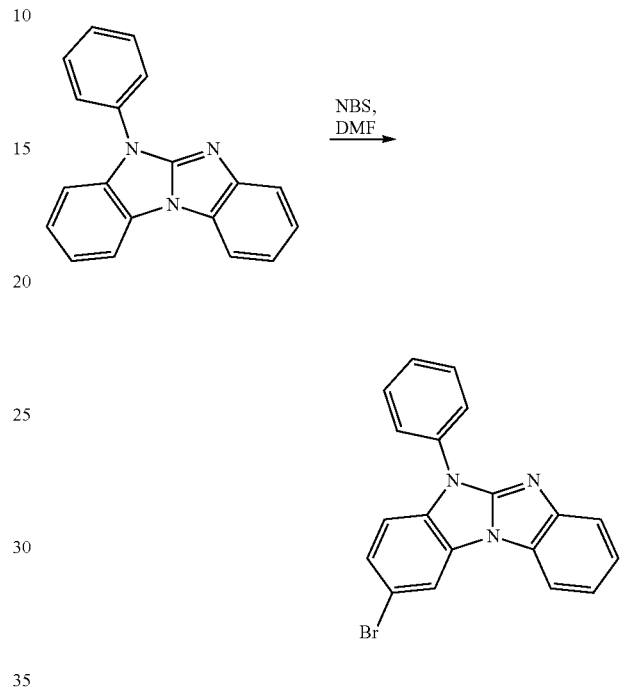

Other bromination methods are, for example, described in Helvetica Chimica Acta 89 (2006) 1123 and SYNLETT 17 (2006) 2841-2845. 10.206

Selective halogenation of (III) with a halogenation agent results in the compounds of formula (II). Halogenation agents are, for example, N-chlorosuccinimide (NCS) (Synlett 18 (2005) 2837-2842); $Br_2$ (Synthesis 10 (2005) 1619-1624), N-bromosuccinimide (NBS)(Organic Letters 12 (2010) 2194-2197; Synlett (2006) 2841-2845), 1,3-dibromo-5,5-dimethylhydantoin (DBH) (Organic Process Research & Development 10 (2006) 822-828, US2002/0151456), $CuBr_2$ (Synthetic Communications 37 (2007) 1381-1388); $R_4NBr_3$ (Can. J. Chem. 67 (1989) 2062), N-iodosuccinimide (NIS) (Synthesis 12 (2001) 1794-1799, J. Heterocyclic Chem. 39 (2002) 933), $KI/KIO_3$(Org. Lett. 9 (2007) 797, Macromolecules 44 (2011) 1405-1413), $NaIO_4/I_2/H_2SO_4$ or $NaIO_4/KI/H_2SO_4$ (J. Heterocyclic Chem. 38 (2001) 77; J. Org. Chem. 75 (2010) 2578-2588); iodine monochloride (ICl; Synthesis (2008) 221-224). Additional methods are described in J. Org. Chem. 74 (2009) 3341-3349; J. Org. Chem. 71 (2006) 7422-7432, Eur. J. Org. Chem. (2008) 1065-1071, Chem. Asian J. 5 (2010) 2162-2167, Synthetic. Commun. 28 (1998) 3225.

Examples of solvents, which can be used in the halogenation, are dimethylformamide (DMF), $CH_2Cl_2$, $CHCl_3$, $CCl_4$, ethanol (EtOH), acetic acid (AcOH), $H_2SO_4$, $C_6H_5Cl$ and mixtures thereof. The halogenation can be done in the presence of acids and lewis acids, respectively, such as, for example, $H_2SO_4$, $ZrCl_4$, $TiCl_4$, $AlCl_3$, $HfCl_4$ and $AlCl_3$ (Synlett 18 (2005) 2837-2842).

Preferably, a compound of formula

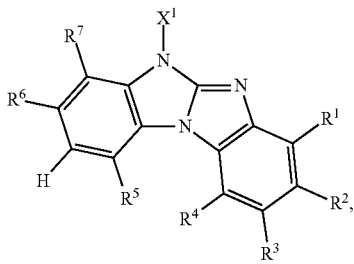

(III)

especially

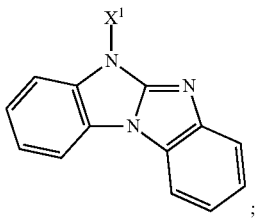

;

is reacted with NBS in a solvent, such as, for example, DMF, acetic acid, chloroform, dichloromethane, chlorobenzene, and mixtures thereof; at a temperature of −40° C. to 150° C. DMF represents the preferred solvent.

The halogenated intermediates (III), wherein $X^3$ is Cl, Br, or I, can be transformed to the boronic ester intermediates (III) by reacting halogenated intermediates (II) with $(Y^1O)_2B—B(OY^1)_2$,

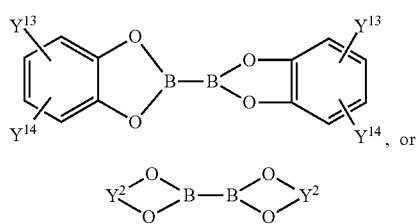

in the presence of a catalyst, such as, for example, [1,1′-bis(diphenylphosphino)ferrocene]dichloropalladium(II), complex ($Pd(Cl)_2(dppf)$), and a base, such as, for example, potassium acetate, in a solvent, such as, for example, dimethyl formamide, dimethyl sulfoxide, dioxane and/or toluene (cf. Prasad Appukkuttan et al., Synlett 8 (2003) 1204).

An overview of the preparation of boronic reagents is given in Angew. Chem. 121 (2009) 9404-9425, Chem. Rev. 95 (1995) 2457-2483, Angew. Chem. Int. Ed. 41 (2002) 4176-4211, Tetrahedron 66 (2010) 8121-8136.

Diboronic acid or diboronate intermediates (III) can also be prepared by reacting halogenated intermediates (III) with alkyl lithium reagents, such as, for example, n-butyl lithium, or t-buthyl lithium, followed by reaction with boronic esters, such as, for example, B(isopropoxy)$_3$, B(methoxy)$_3$, or

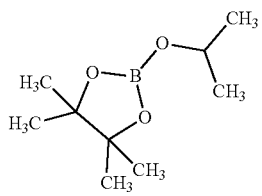

(cf. Synthesis (2000) 442-446).

The compounds of formula I can be obtained starting from the intermediates and suitable co-reactants, for example, by Suzuki-, Stille-, or Negishi-coupling reactions.

A process for the preparation of a compound of formula

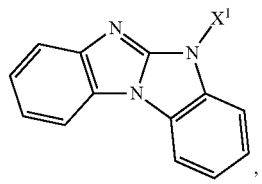

, wherein $X^1$ is as defined above, may comprise (a) heating a compound of formula

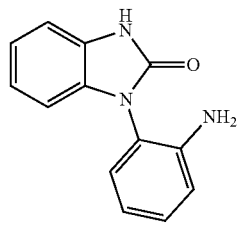 [SMILES: Nc1ccccc1-n1c(=O)[nH]c2ccccc21]

in $H_3PO_4$, polyphosporic acid $CH_3SO_3H/P_2O_5$, $CH_3SO_3H$, or sulfuric acid to obtain a compound of formula

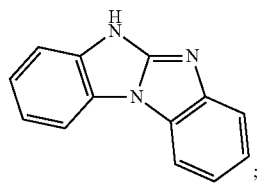 [SMILES: c1ccc2c(c1)nc1[nH]c3ccccc3n12]

;

and (b) reacting the compound of formula XI to a compound of formula (I). Various examples for step b) are illustrated above. In step a) a solvent, or mixtures of solvents having a boiling point above 140° C., such as, for example, xylene, or mesitylen, may be present. Compounds of formula

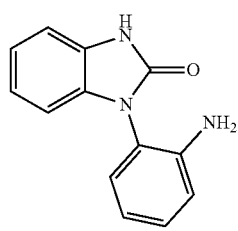 [SMILES: Nc1ccccc1-n1c(=O)[nH]c2ccccc21]

are stirred under an atmosphere of inert gas, such as, for example, nitrogen, or argon, at a temperature above 140° C., preferably above 160° C., more preferably above 180° C., for a time of 30 minutes to 3 weeks, preferably 1 to 48 h.

It has been found that the compounds of the formula I are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs), the compounds of the formula I being particularly suitable in OLEDs for use as matrix material in a light-emitting layer and/or as hole and/or exciton blocker material and/or as electron and/or exciton blocker material, especially in combination with a phosphorescence emitter. In the case of use of the inventive compounds of the formula I in OLEDs, OLEDs which have good efficiencies and a long lifetime and which can be operated especially at a low use and operating voltage are obtained. The inventive compounds of the formula I are suitable especially for use as matrix and/or hole/exciton blocker materials for blue and green emitters, for example light blue or deep blue emitters, these being especially phosphorescence emitters. Furthermore, the compounds of the formula I can be used as conductor/complementary materials in organic electronics applications selected from switching elements and organic solar cells.

The compounds of the formula I can be used as matrix material and/or hole/exciton blocker material and/or electron/exciton blocker material and/or hole injection material and/or electron injection material and/or hole conductor material (hole transport material) and/or electron conductor material (electron transport material), preferably as matrix material and/or electron/exciton blocker and/or hole transporting material in organic electronics applications, especially in OLEDs. The inventive compounds of the formula I are more preferably used as matrix materials in organic electronics applications, especially in OLEDs.

In the emission layer or one of the emission layers of an OLED, it is also possible to combine an emitter material with a matrix material of the compound of the formula I and a further matrix material which has, for example, a good hole conductor (hole transport) property. This achieves a high quantum efficiency of this emission layer.

When a compound of the formula I is used as matrix material in an emission layer and additionally as hole/exciton blocker material and/or electron/exciton blocker material, owing to the chemical identity or similarity of the materials, an improved interface between the emission layer and the adjacent hole/exciton blocker material and/or electron/exciton blocker material is obtained, which can lead to a decrease in the voltage with equal luminance and to an extension of the lifetime of the OLED. Moreover, the use of the same material for hole/exciton blocker material and/or electron/exciton blocker material and for the matrix of an emission layer allows the production process of an OLED to be simplified, since the same source can be used for the vapor deposition process of the material of one of the compounds of the formula I.

Suitable structures of organic electronic devices are known to those skilled in the art and are specified below.

The organic transistor generally includes a semiconductor layer formed from an organic layer with hole transport capacity and/or electron transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or electron transport capacity. In addition, it is possible for further layers known to those skilled in the art to be present in the organic solar cell. The layer with hole transport capacity may comprise the compounds of formula I.

It is likewise possible that the compounds of the formula I are present both in the light-emitting layer (preferably as matrix material) and in the blocking layer for electrons (as electron/exciton blockers).

The present invention further provides an organic light-emitting diode comprising an anode An and a cathode Ka and a light-emitting layer E arranged between the anode An and the cathode Ka, and if appropriate at least one further layer selected from the group consisting of at least one blocking layer for holes/excitons, at least one blocking layer for electrons/excitons, at least one hole injection layer, at least one hole conductor layer, at least one electron injection layer and at least one electron conductor layer, wherein the at least one compound of the formula I is present in the light-emitting layer E and/or in at least one of the further layers. The at least one compound of the formula I is preferably present in the light-emitting layer and/or the blocking layer for holes.

The present application further relates to a light-emitting layer comprising at least one compound of the formula I.

Structure of the Inventive OLED

The inventive organic light-emitting diode (OLED) thus generally has the following structure: an anode (An) and a cathode (Ka) and a light-emitting layer E arranged between the anode (An) and the cathode (Ka).

The inventive OLED may, for example—in a preferred embodiment—be formed from the following layers:

1. Anode
2. Hole conductor layer
3. Light-emitting layer
4. Blocking layer for holes/excitons
5. Electron conductor layer
6. Cathode Layer sequences different than the aforementioned structure are also possible, and are known to those skilled in the art. For example, it is possible that the OLED does not have all of the layers mentioned; for example, an OLED with layers (1) (anode), (3) (light-emitting layer) and (6) (cathode) is likewise suitable, in which case the functions of the layers (2) (hole conductor layer) and (4) (blocking layer for holes/excitons) and (5) (electron conductor layer) are assumed by the adjacent layers. OLEDs which have layers (1), (2), (3) and (6), or layers (1), (3), (4), (5) and (6), are likewise suitable. In addition, the OLEDs may have a blocking layer for electrons/excitons between the hole conductor layer (2) and the Light-emitting layer (3).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole conductor layer, in one embodiment, may simultaneously block excitons and/or electrons.

Furthermore, the individual layers of the OLED among those specified above may in turn be formed from two or more layers. For example, the hole conductor layer may be formed from a layer into which holes are injected from the electrode, and a layer which transports the holes away from the hole-injecting layer into the light-emitting layer. The electron conduction layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used as emitter substances in accordance with the invention.

In order to obtain particularly efficient OLEDs, for example, the HOMO (highest occupied molecular orbital) of the hole conductor layer should be matched to the work function of the anode, and the LUMO (lowest unoccupied molecular orbital) of the electron conductor layer should be matched to the work function of the cathode, provided that the aforementioned layers are present in the inventive OLEDs.

The anode (1) is an electrode which provides positive charge carriers. It may be formed, for example, from materials which comprise a metal, a mixture of various metals, a metal alloy, a metal oxide or a mixture of various metal oxides. Alternatively, the anode may be a conductive polymer. Suitable metals comprise metals and alloys of the metals of the main groups, transition metals and of the lanthanoids, especially the metals of groups Ib, IVa, Va and VIa of the periodic table of the elements, and the transition metals of group VIIIa. When the anode is to be transparent, generally mixed metal oxides of groups IIb, IIIb and IVb of the periodic table of the elements (IUPAC version) are used, for example indium tin oxide (ITO). It is likewise possible that the anode (1) comprises an organic material, for example polyaniline, as described, for example, in Nature, Vol. 357, pages 477 to 479 (Jun. 11, 1992). At least either the anode or the cathode should be at least partly transparent in order to be able to emit the light formed. The material used for the anode (1) is preferably ITO.

Suitable hole conductor materials for layer (2) of the inventive OLEDs are disclosed, for example, in Kirk-Othmer Encyclopedia of Chemical Technology, 4th edition, Vol. 18, pages 837 to 860, 1996. Both hole-transporting molecules and polymers can be used as the hole transport material. Hole-transporting molecules typically used are selected from the group consisting of tris[N-(1-naphthyl)-N-(phenylamino)]triphenylamine (1-NaphDATA), 4,4'-bis[N-(1-naphthyl)-N-phenylamino]biphenyl (α-NPD), N,N'-diphenyl-N,N'-bis(3-methylphenyl)[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA), 4,4',4"-tris(N-carbazolyl)triphenylamine (TCTA), N,N'-bis(naphthalen-2-yl)-N,N'-bis(phenyl)benzidine (β-NPB), N,N'-bis(3-methylphenyl)-N,N'-bis(phenyl)-9,9-spirobifluorene (Spiro-TPD), N,N'-bis(naphthalen-1-yl)-N,N'-bis(phenyl)-9,9-spirobifluorene (Spiro-NPB), N,N'-bis(3-methylphenyl)-N,N'-bis(phenyl)-9,9-dimethylfluorene (DMFL-TPD), di[4-(N,N-ditolylamino)phenyl]cyclohexane, N,N'-bis(naphthalen-1-yl)-N,N'-bis(phenyl)-9,9-dimethylfluorene, N,N'-bis(naphthalen-1-yl)-N,N'-bis(phenyl)-2,2-dimethylbenzidine, N,N'-bis(naphthalen-1-yl)-N,N'-bis(phenyl)benzidine, N,N'-bis(3-methylphenyl)-N,N'-bis(phenyl)benzidine, 2,3,5,6-tetrafluoro-7,7,8,8-tetracyanoquinodimethane (F4-TCNQ), 4,4',4"-tris(N-3-methylpheny-N-phenylamino)triphenylamine, 4,4',4"-tris(N-(2-naphthyl)-N-phenyl-amino)triphenylamine, pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di[4-(N,N-ditolylamino)phenyl]benzidine (NTNPB), N,N'-diphenyl-N,N'-di[4-(N,N-diphenylamino)phenyl]benzidine (NPNPB), N,N'-di(naphthalen-2-yl)-N,N'-diphenylbenzene-1,4-diamine (β-NPP), N,N'-bis(3-methylphenyl)-N,N'-bis(phenyl)-9,9-diphenylfluorene (DPFL-TPD), N,N'-bis(naphthalen-1-yl)-N,N'-bis(phenyl)-9,9-diphenylfluorene (DPFL-NPB), 2,2',7,7'-tetrakis(N,N-diphenylamino)-9,9'-spirobifluorene (Spiro-TAD), 9,9-bis[4-(N,N-bis(biphenyl-4-yl)amino)phenyl]-9H-fluorene (BPAPF), 9,9-bis[4-(N,N-bis(naphthalen-2-yl)amino)phenyl]-9H-fluorene (NPAPF), 9,9-bis[4-(N, N-bis(naphthalen-2-yl)-N,N'-bisphenylamino)phenyl]-9H-fluorene (NPBAPF), 2,2',7,7'-tetrakis[N-naphthalenyl(phenyl)amino]-9,9'-spirobifluorene (Spiro-2NPB), N,N'-bis(phenanthren-9-yl)-N,N'-bis(phenyl)benzidine (PAPB), 2,7-bis[N,N-bis(9,9-spirobifluoren-2-yl)amino]-9,9-spirobifluorene (Spiro-5), 2,2'-bis[N,N-bis(biphenyl-4-yl)amino]-9,9-spirobifluorene (2,2'-Spiro-DBP), 2,2'-bis(N,N-diphenylamino)-9,9-spirobifluorene (Spiro-BPA), 2,2',7,7'-tetra(N,N-ditolyl)aminospirobifluorene (Spiro-TTB), N,N,N',N'-tetranaphthalen-2-ylbenzidine (TNB), porphyrin compounds and phthalocyanines such as copper phthalocyanines and titanium oxide phthalocyanines. Hole-transporting polymers typically used are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in one embodiment—it is possible to use carbene complexes as hole conductor materials, the band gap of the at least one hole conductor material generally being greater than the band gap of the emitter material used. In the context of the present application, "band gap" is understood to mean the triplet energy. Suitable carbene complexes are, for example, carbene complexes as described in WO 2005/019373 A2, WO 2006/056418 A2, WO 2005/

113704, WO 2007/115970, WO 2007/115981 and WO 2008/000727. One example of a suitable carbene complex is Ir(dpbic)$_3$ with the formula:

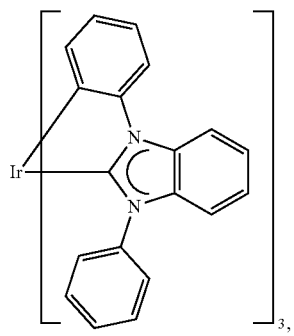

which is disclosed, for example, in WO2005/019373. In principle, it is possible that the hole conductor layer comprises at least one compound of the formula I as hole conductor material.

The light-emitting layer (3) comprises at least one emitter material. In principle, it may be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula I can be used as the matrix in the light-emitting layer.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006121811 A1, WO 2007095118 A2, WO 2007/115970, WO 2007/115981, WO 2008/000727, WO2010129323, WO2010056669 and WO10086089.

Further suitable metal complexes are the commercially available metal complexes tris(2-phenylpyridine)iridium (III), iridium(III) tris(2-(4-tolyl)pyridinato-N,C$^{2'}$), bis(2-phenylpyridine)(acetylacetonato)iridium(III), iridium(III) tris(1-phenylisoquinoline), iridium(III) bis(2,2'-benzothienyl)pyridinato-N,C$^{3'}$)(acetylacetonate), tris(2-phenylquinoline)iridium(III), iridium(III) bis(2-(4,6-difluorophenyl)pyridinato-N,C$^2$)picolinate, iridium(III) bis(1-phenylisoquinoline)(acetylacetonate), bis(2-phenylquinoline)(acetylacetonato) iridium(III), iridium(III) bis(di-benzo[f,h]quinoxaline)(acetylacetonate), iridium(III) bis(2-methyldibenzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-yl)isoquinoline](acetylacetonato)iridium(III), bis(2-phenylbenzothiazolato)(acetylacetonato)iridium(III), bis(2-(9,9-dihexylfluorenyl)-1-pyridine)(acetylacetonato)iridium(III), bis(2-benzo[b]thiophen-2-ylpyridine)(acetylacetonato) iridium(III).

In addition, the following commercially available materials are suitable: tris(dibenzoylacetonato)mono (phenanthroline)europium(III), tris(dibenzoylmethane) mono(phenanthroline)europium(III), tris(dibenzoylmethane)mono(5-aminophenanthroline) europium(III), tris(di-2-naphthoylmethane)mono (phenanthroline)europium(III), tris(4-bromobenzoylmethane)mono(phenanthroline)europium (III), tris(di(biphenyl)methane)mono(phenanthroline) europium(III), tris(dibenzoylmethane)mono(4,7-diphenylphenanthroline)europium(III), tris (dibenzoylmethane)mono(4,7-di-methylphenanthroline) europium(III), tris(dibenzoylmethane)mono(4,7-dimethylphenanthrolinedisulfonic acid)europium(III) disodium salt, tris[di(4-(2-(2-ethoxyethoxy)ethoxy)benzoyl-methane)]mono(phenanthroline)europium(III) and tris[di[4-(2-(2-ethoxyethoxy)ethoxy)benzoylmethane)]mono(5-aminophenanthroline)europium(III), osmium(II) bis(3-(trifluoromethyl)-5-(4-tert-butylpyridyl)-1,2,4-triazolato) diphenylmethylphosphine, osmium(II) bis(3-(trifluoromethyl)-5-(2-pyridyl)-1,2,4-triazole) dimethylphenylphosphine, osmium(II) bis(3-(trifluoromethyl)-5-(4-tert-butylpyridyl)-1,2,4-triazolato) dimethylphenylphosphine, osmium(II) bis(3-(trifluoromethyl)-5-(2-pyridyl)pyrazolato) dimethylphenylphosphine, tris[4,4'-di-tert-butyl(2,2')-bipyridine]ruthenium(III), osmium(II) bis(2-(9,9-dibutylfluorenyl)-1-isoquinoline(acetylacetonate).

The light emitting layer comprises preferably a compound of the formula

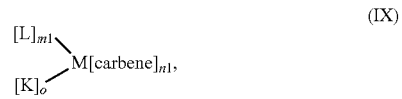 (IX)

which are described in WO 2005/019373 A2, wherein the symbols have the following meanings:

M is a metal atom selected from the group consisting of Co, Rh, Ir, Nb, Pd, Pt, Fe, Ru, Os, Cr, Mo, W, Mn, Tc, Re, Cu, Ag and Au in any oxidation state possible for the respective metal atom;

Carbene is a carbene ligand which may be uncharged or monoanionic and monodentate, bidentate or tridentate, with the carbene ligand also being able to be a biscarbene or triscarbene ligand;

L is a monoanionic or dianionic ligand, which may be monodentate or bidentate;

K is an uncharged monodentate or bidentate ligand selected from the group consisting of phosphines; phosphonates and derivatives thereof, arsenates and derivatives thereof; phosphites; CO; pyridines; nitriles and conjugated dienes which form a π complex with M$^1$;

n1 is the number of carbene ligands, where n1 is at least 1 and when n1>1 the carbene ligands in the complex of the formula I can be identical or different;

m1 is the number of ligands L, where m1 can be 0 or ≥1 and when m1>1 the ligands L can be identical or different;

o is the number of ligands K, where o can be 0 or ≥1 and when o>1 the ligands K can be identical or different;

where the sum n1+m1+o is dependent on the oxidation state and coordination number of the metal atom and on the denticity of the ligands carbene, L and K and also on the charge on the ligands, carbene and L, with the proviso that n1 is at least 1.

Carbene complexes which are suitable triplet emitters are described, for example, in WO 2006/056418 A2, WO 2005/113704, WO 2007/115970, WO 2007/115981 and WO 2008/000727, WO2009050281, WO2009050290, WO2011051404 and WO2011073149.

More preferred are metal-carbene complexes of the general formula

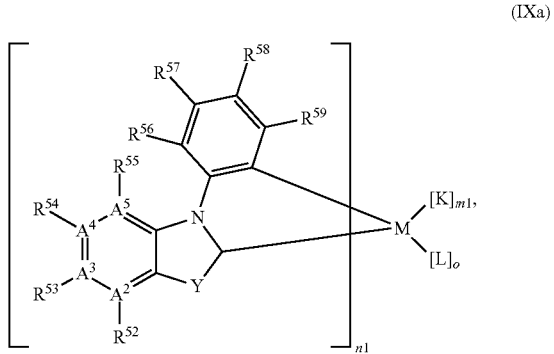

(IXa)

which are described in U.S. patent application Nos. 61/286,046, 61/323,885 and Europen patent application 10187176.2 (PCT/EP2010/069541), where M, n1, Y, $A^2$, $A^3$, $A^4$, $A^5$, $R^{51}$, $R^{52}$, $R^{53}$, $R^{54}$, $R^{55}$, $R^{56}$, $R^{57}$, $R^{58}$, $R^{59}$, K, L, m1 and o are each defined as follows:

M is Ir, or Pt, n1 is an integer selected from 1, 2 and 3,

Y is $NR^{51}$, O, S or $C(R^{25})_2$, $A^2$, $A^3$, $A^4$, and $A^5$ are each independently N or C, where 2 A=nitrogen atoms and at least one carbon atom is present between two nitrogen atoms in the ring, $R^{51}$ is a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, $R^{52}$, $R^{53}$, $R^{54}$ and $R^{55}$ are each, if $A^2$, $A^3$, $A^4$ and/or $A^5$ is N, a free electron pair, or, if $A^2$, $A^3$, $A^4$ and/or $A^5$ is C, each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{53}$ and $R^{54}$ together with $A^3$ and $A^4$ form an optionally substituted, unsaturated ring optionally interrupted by at least one further heteroatom and having a total of 5 to 18 carbon atoms and/or heteroatoms, $R^{56}$, $R^{57}$, $R^{58}$ and $R^{59}$ are each independently hydrogen, linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, cycloheteroalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, group with donor or acceptor action, or $R^{56}$ and $R^{57}$, $R^{57}$ and $R^{58}$ or $R^{58}$ and $R^{59}$, together with the carbon atoms to which they are bonded, form a saturated, unsaturated or aromatic, optionally substituted ring optionally interrupted by at least one heteroatom and having a total of 5 to 18 carbon atoms and/or heteroatoms, and/or if $A^5$ is C, $R^{55}$ and $R^{56}$ together form a saturated or unsaturated, linear or branched bridge optionally comprising heteroatoms, an aromatic unit, heteroaromatic unit and/or functional groups and having a total of 1 to 30 carbon atoms and/or heteroatoms, to which is optionally fused a substituted or unsubstituted, five- to eight-membered ring comprising carbon atoms and/or heteroatoms, $R^{25}$ is independently a linear or branched alkyl radical optionally interrupted by at least one heteroatom, optionally bearing at least one functional group and having 1 to 20 carbon atoms, cycloalkyl radical optionally interrupted by at least one heteroatom, optionally bearing at least one functional group and having 3 to 20 carbon atoms, substituted or unsubstituted aryl radical optionally interrupted by at least one heteroatom, optionally bearing at least one functional group and having 6 to 30 carbon atoms, substituted or unsubstituted heteroaryl radical optionally interrupted by at least one heteroatom, optionally bearing at least one functional group and having a total of 5 to 18 carbon atoms and/or heteroatoms, K is an uncharged mono- or bidentate ligand, L is a mono- or dianionic ligand, preferably monoanionic ligand, which may be mono- or bidentate, m1 is 0, 1 or 2, where, when m1 is 2, the K ligands may be the same or different, o is 0, 1 or 2, where, when o is 2, the L ligands may be the same or different.

The compound of formula IX is preferably a compound of the formula:

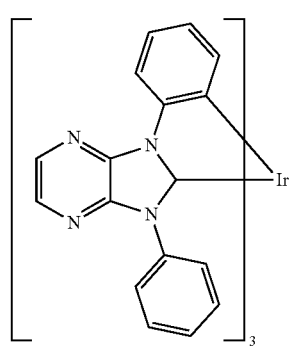

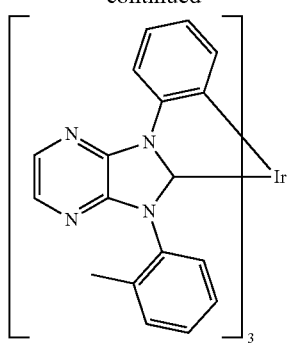
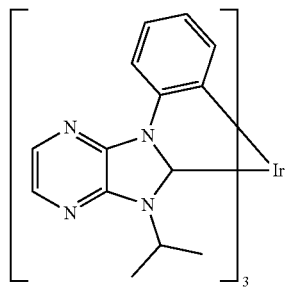
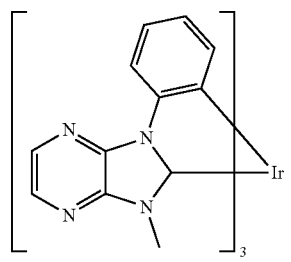
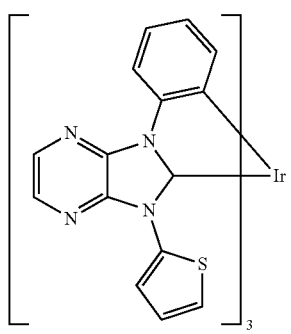
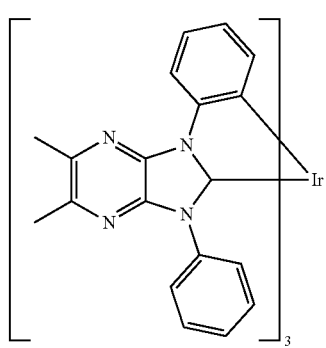
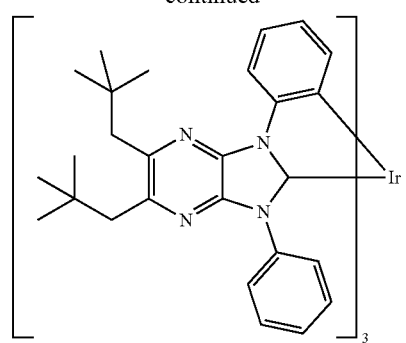
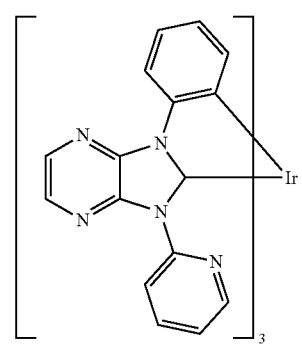
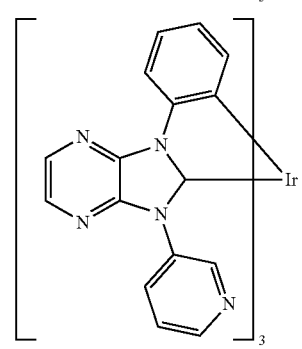
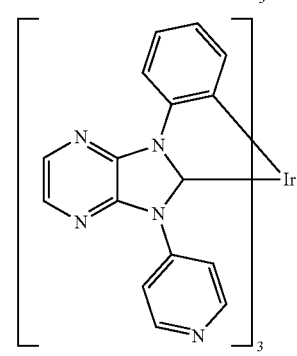
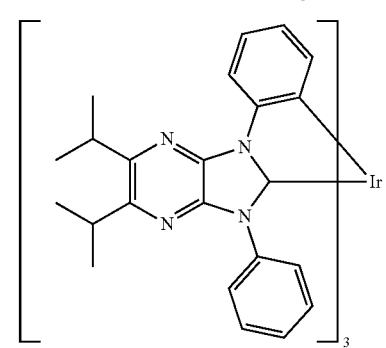

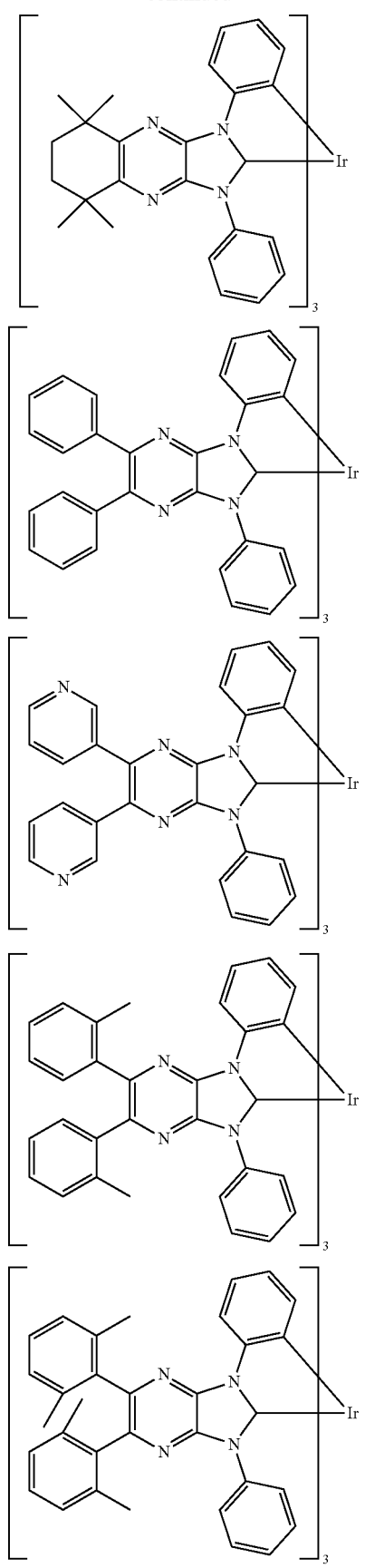
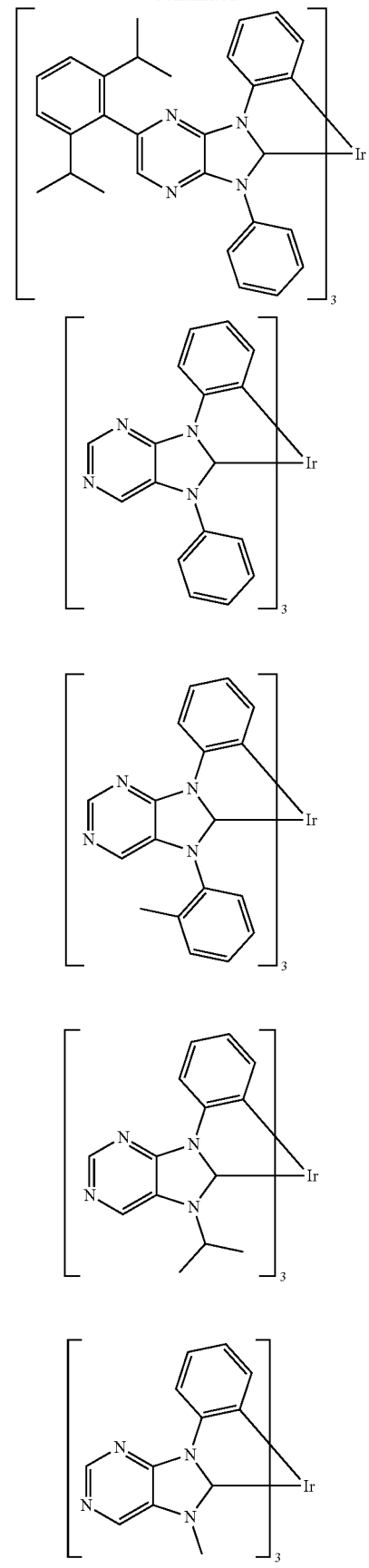

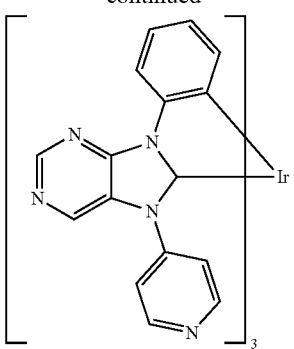
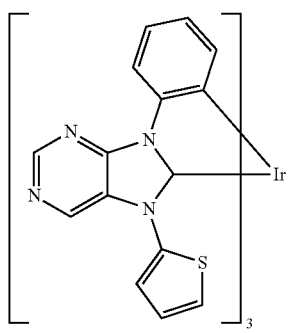
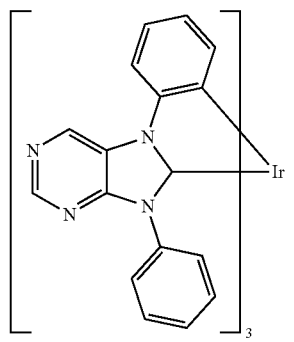
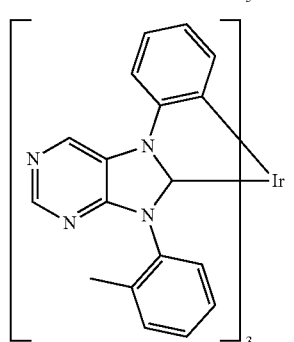
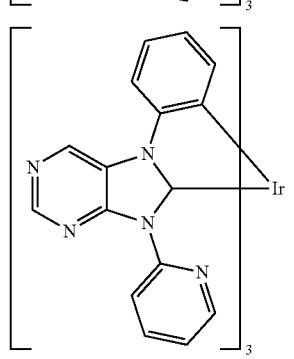
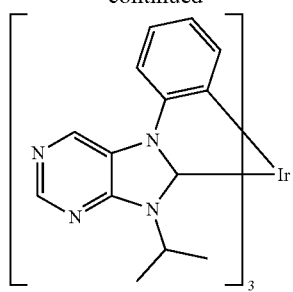
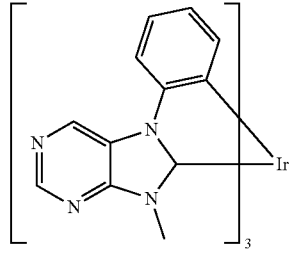
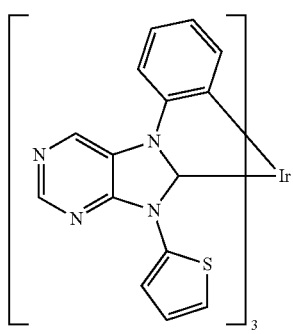
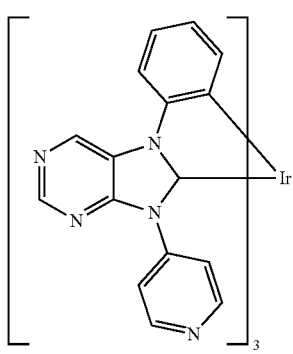
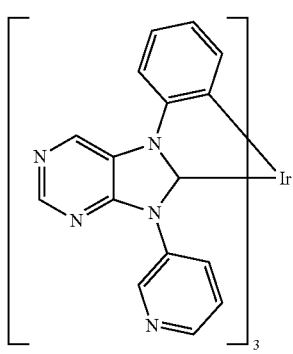

-continued
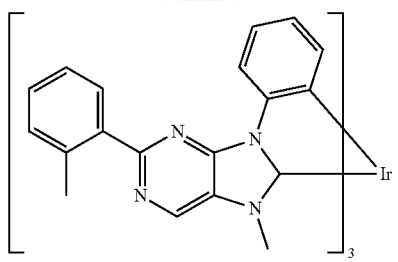
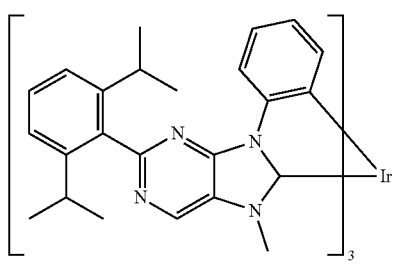
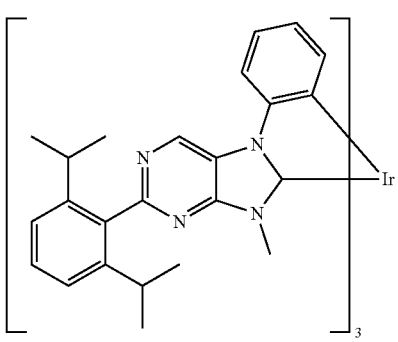
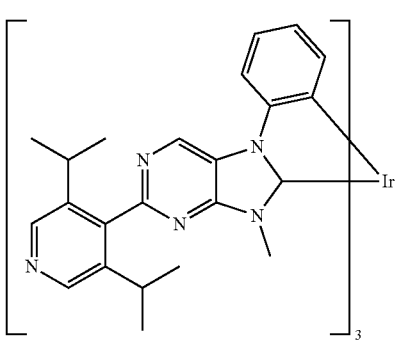
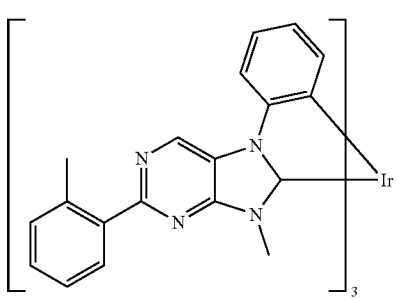
-continued
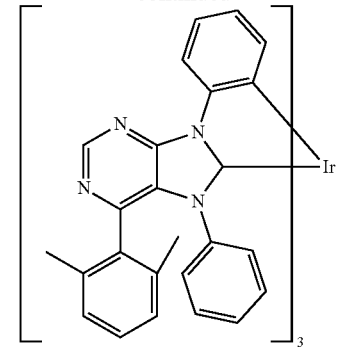
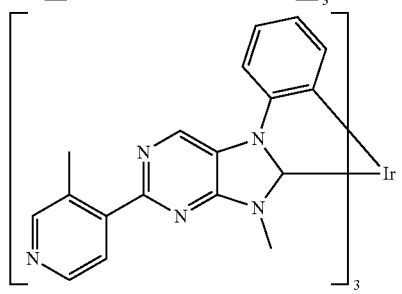
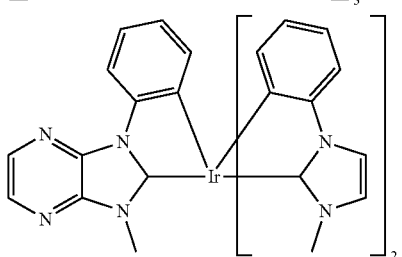
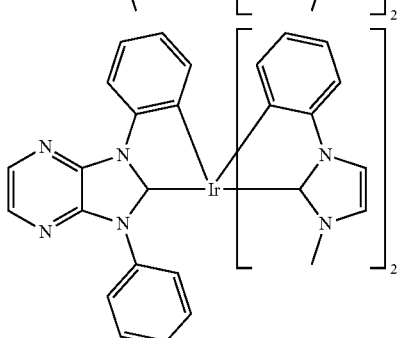
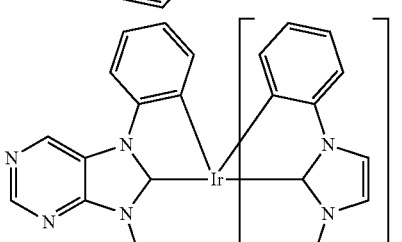
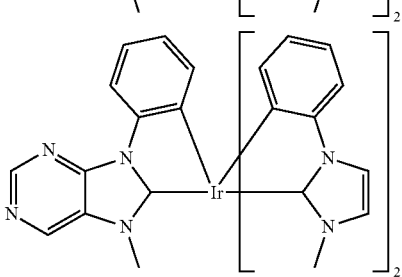

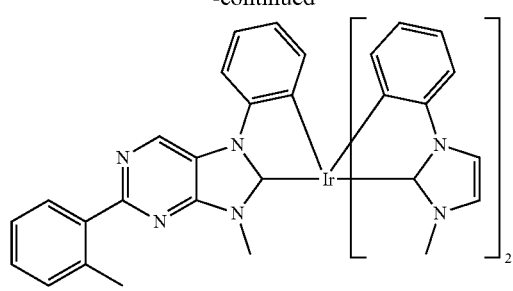
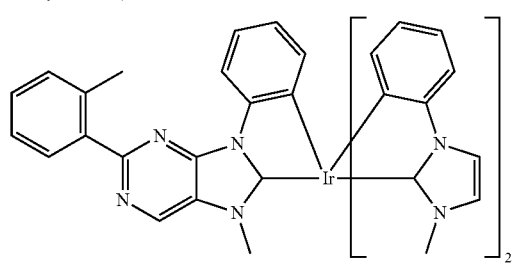
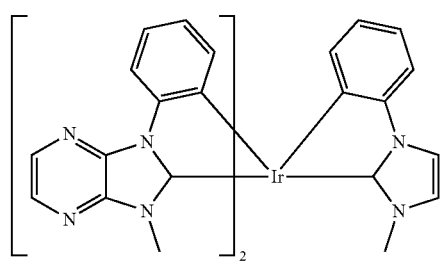
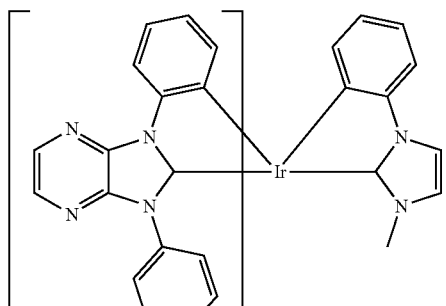
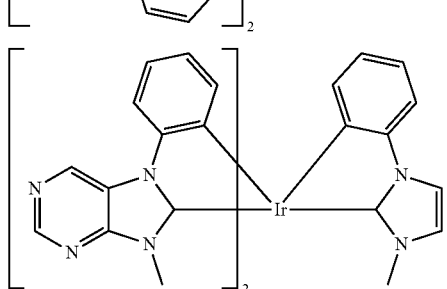
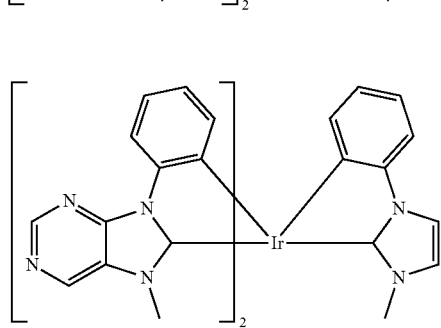
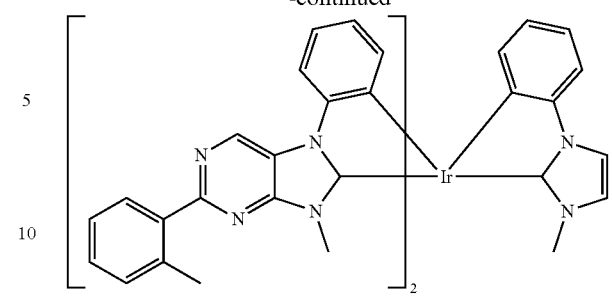
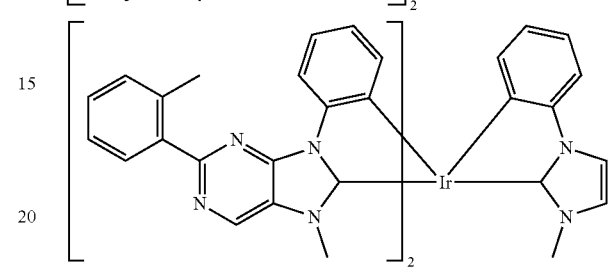
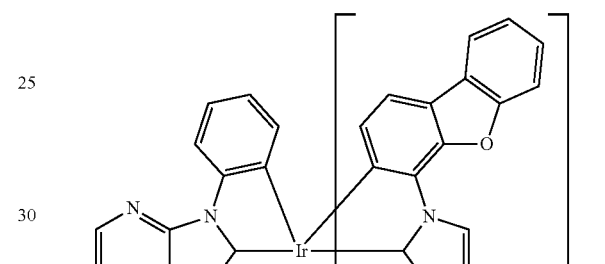
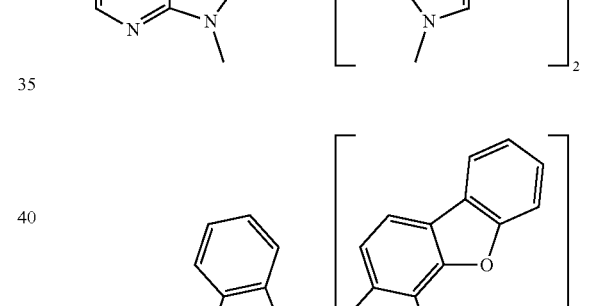
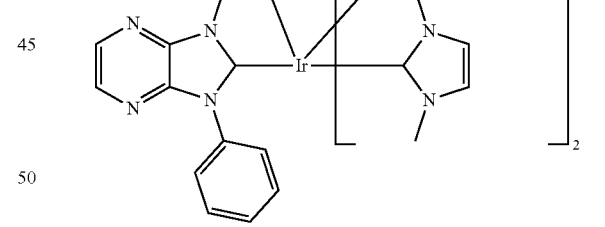
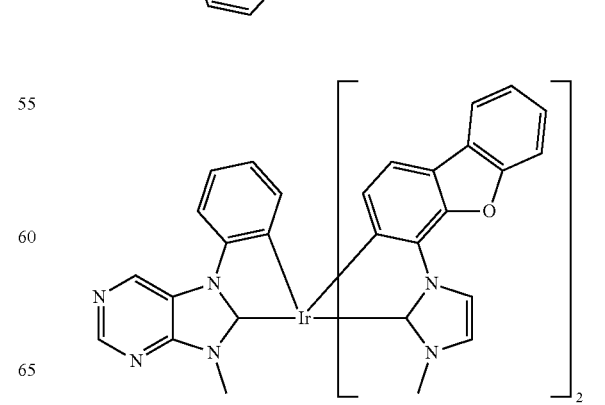

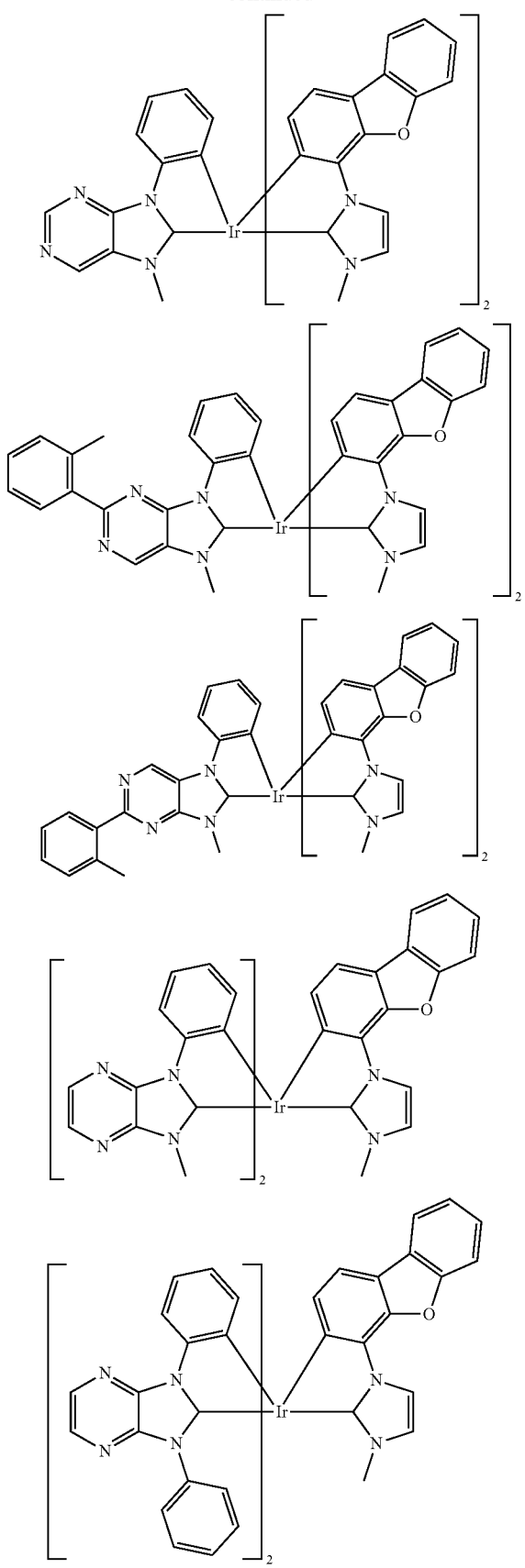
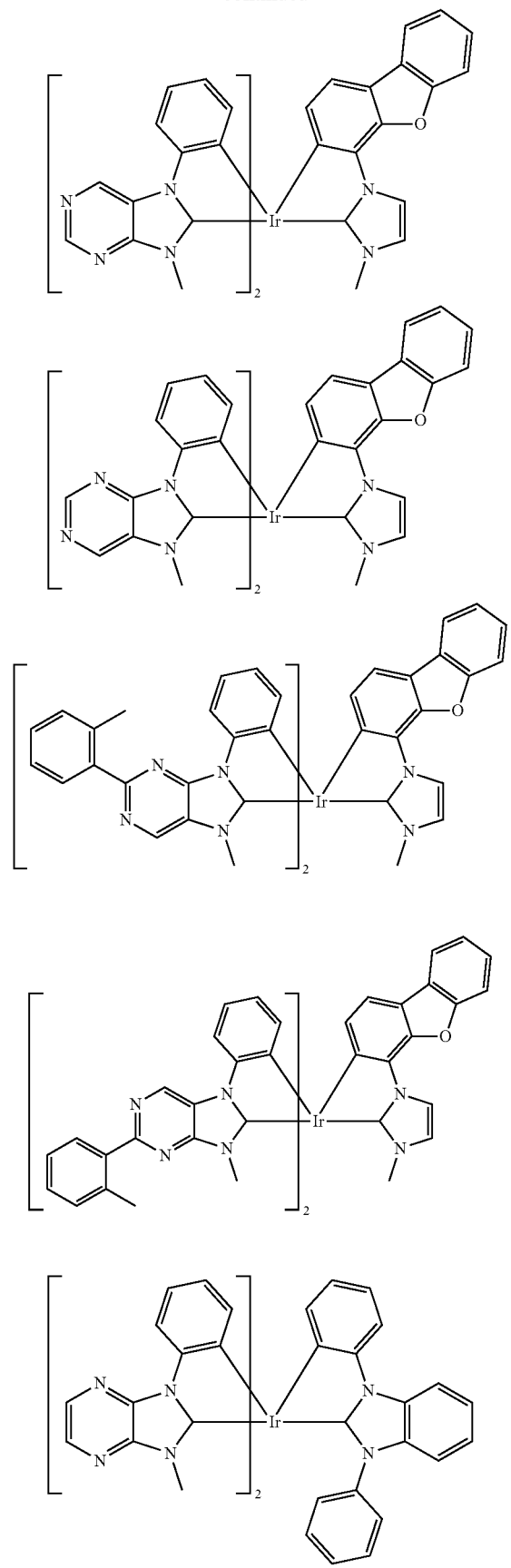

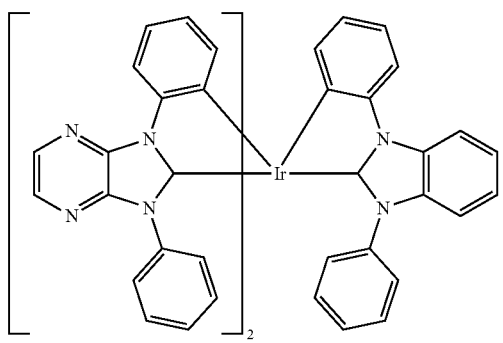
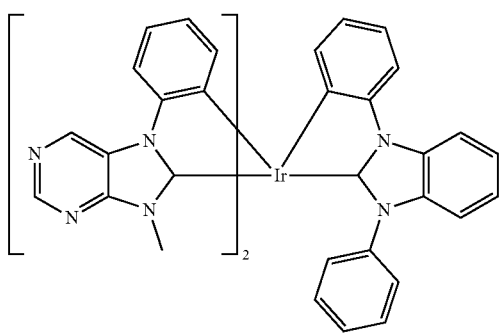
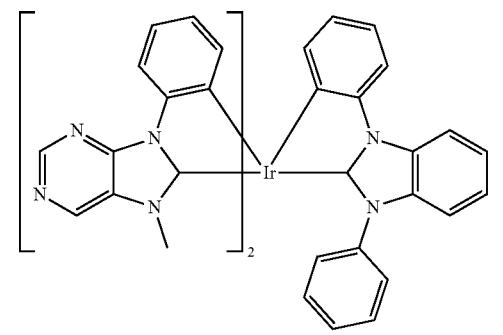
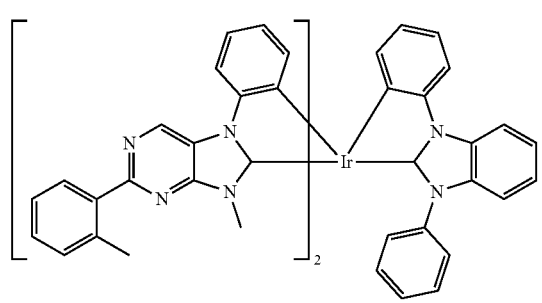
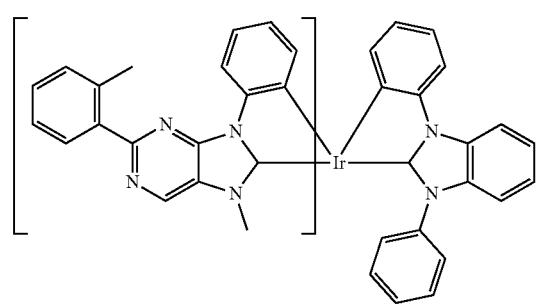
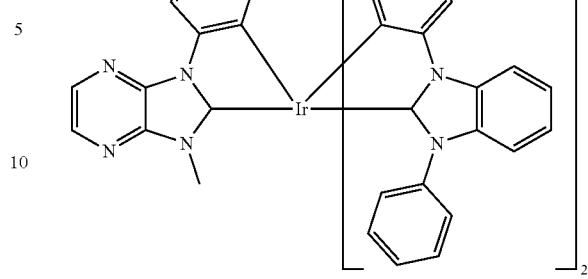
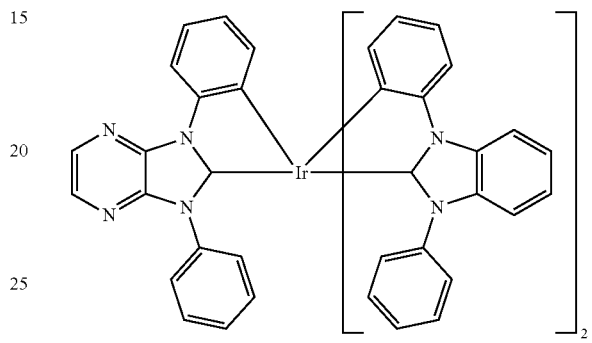
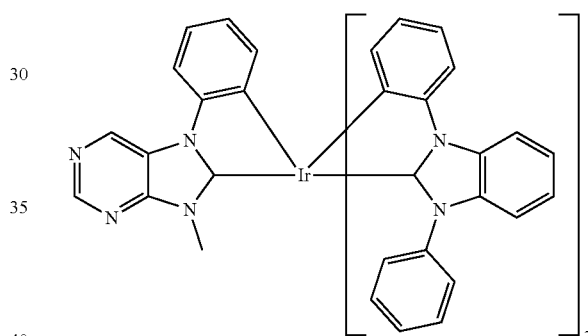
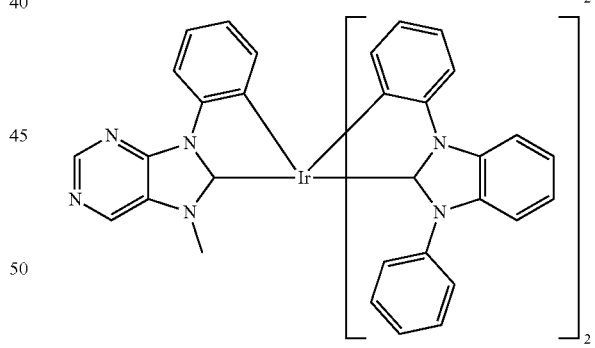
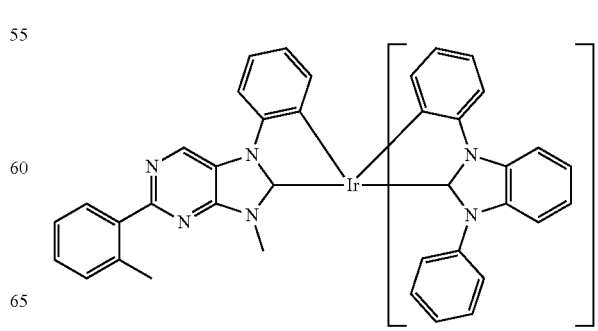

-continued
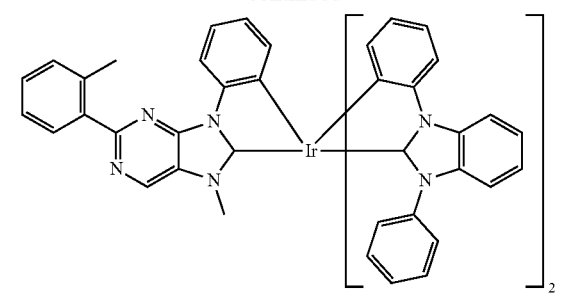
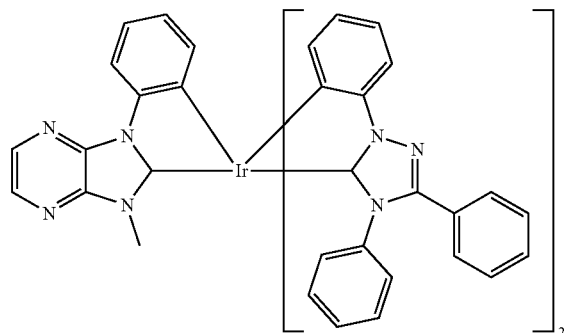
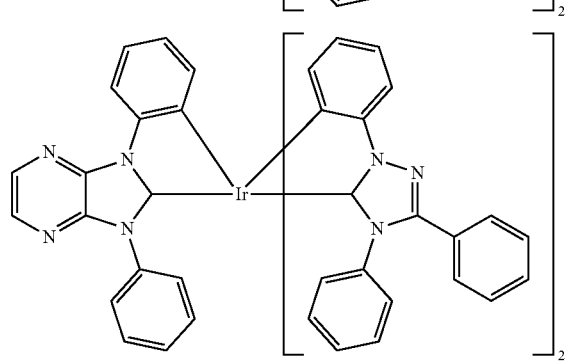
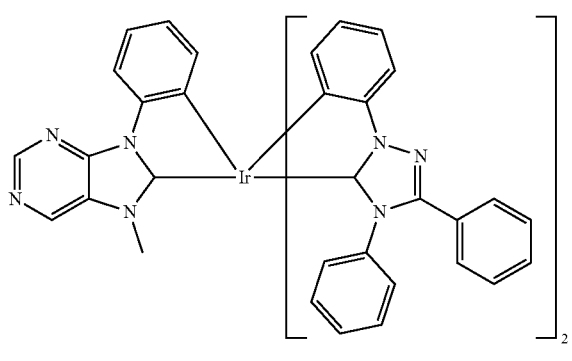
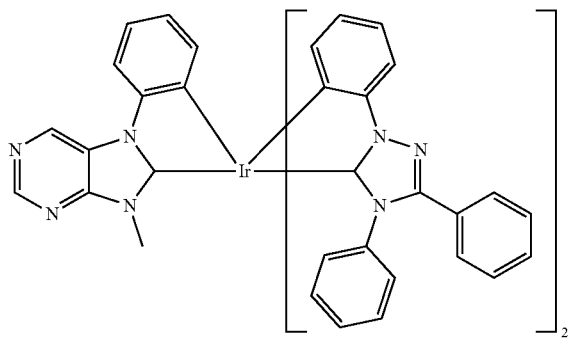
-continued
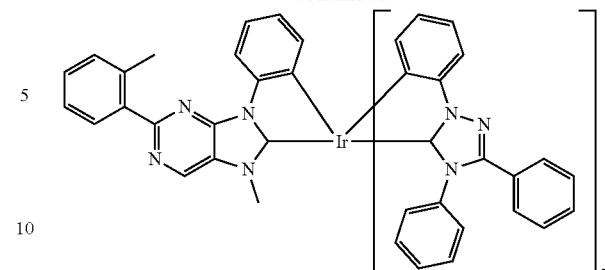
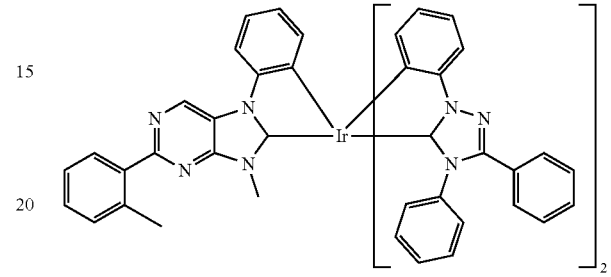
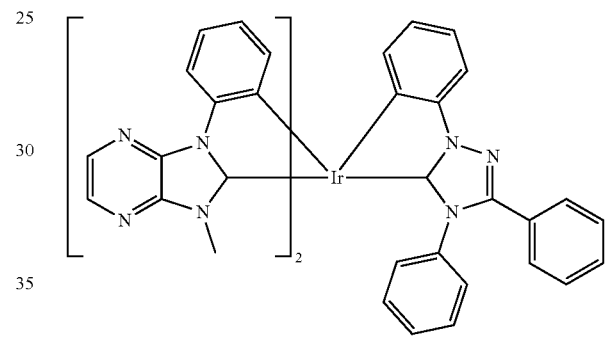
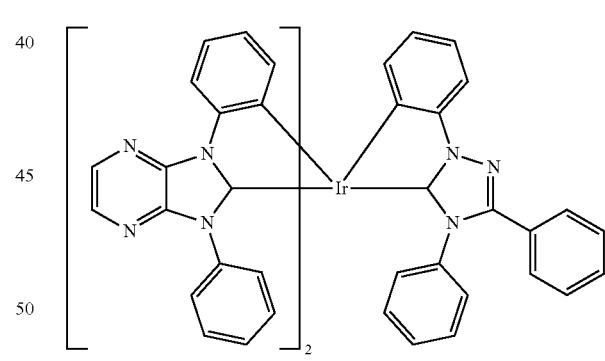
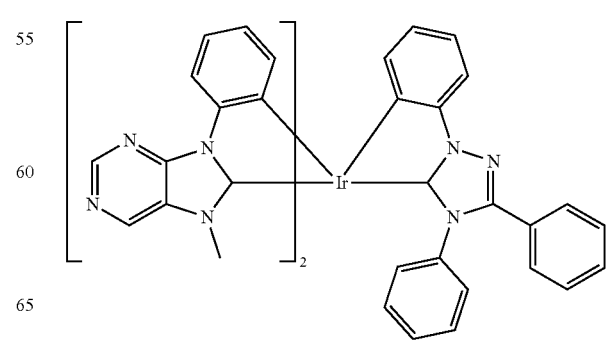

75
-continued
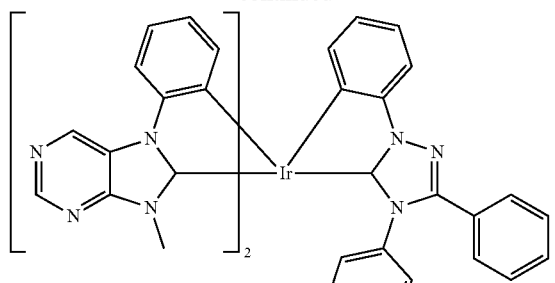
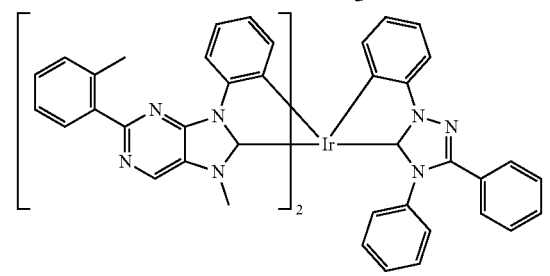
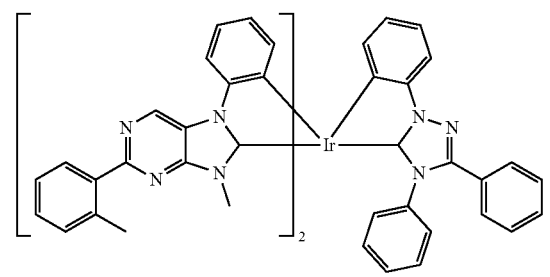
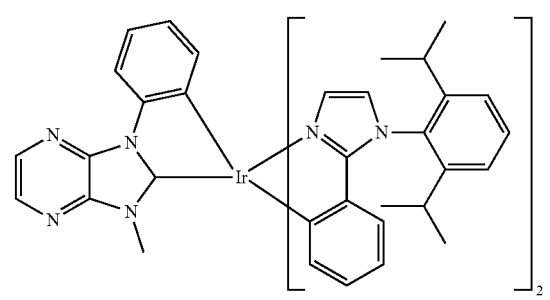
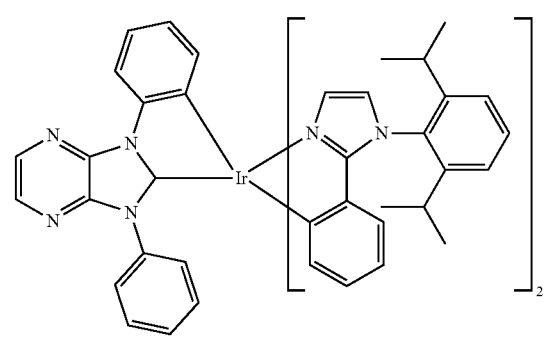
76
-continued
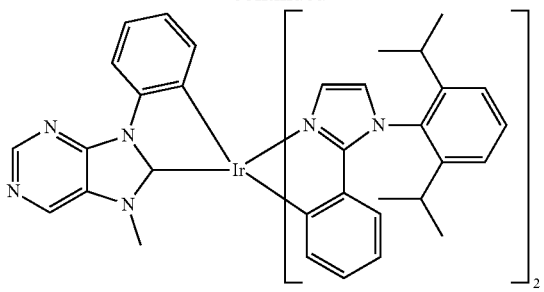
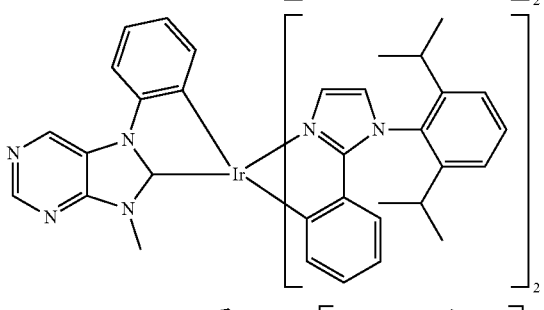
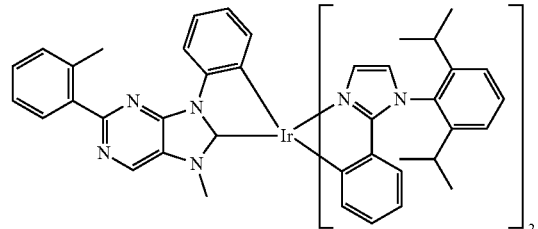
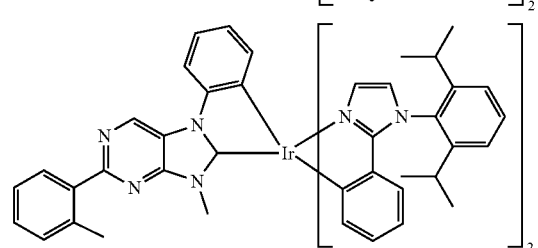
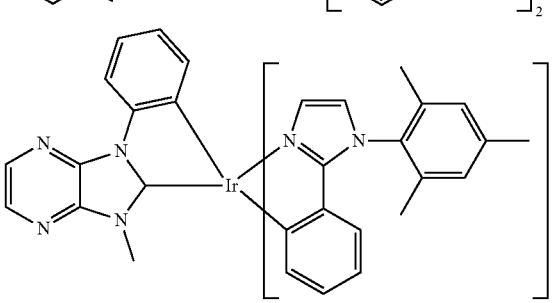
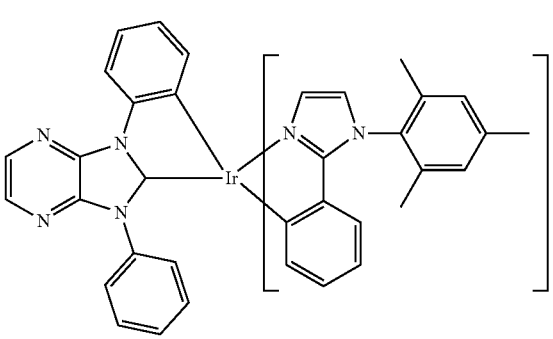

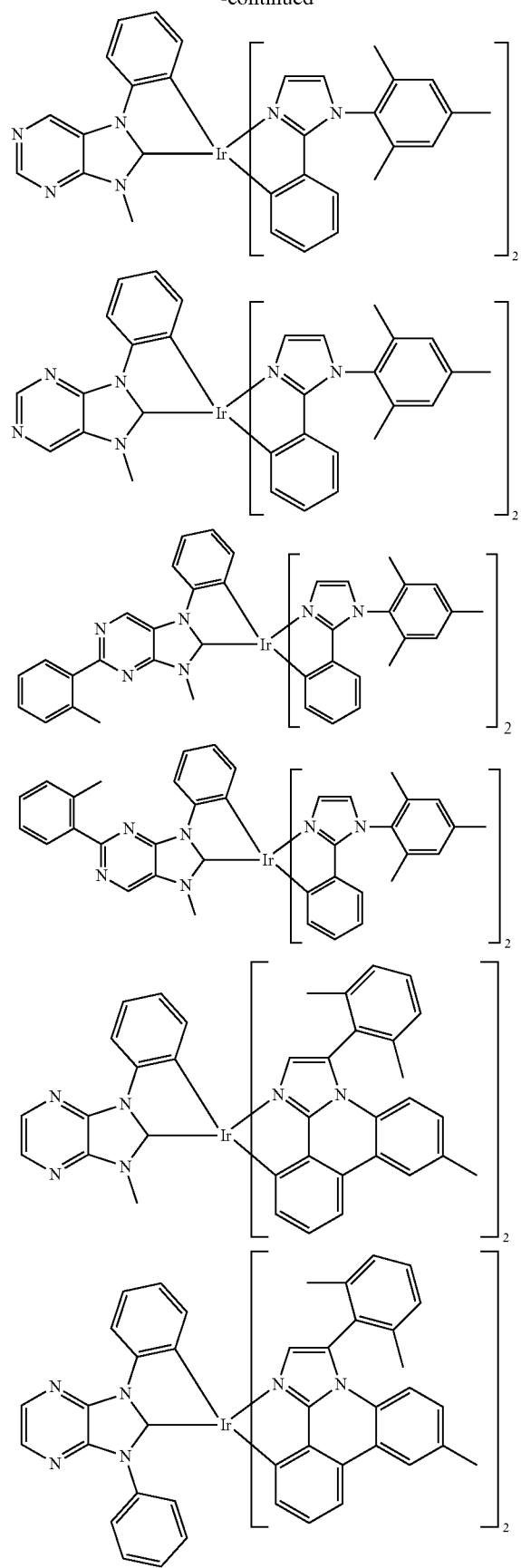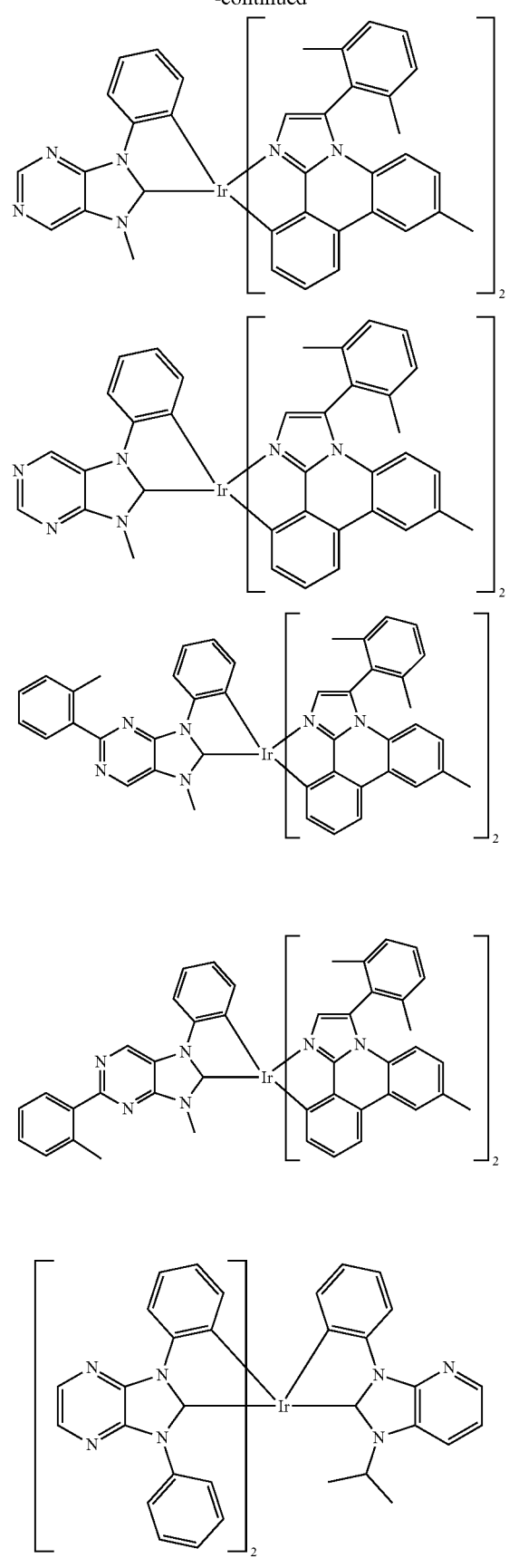

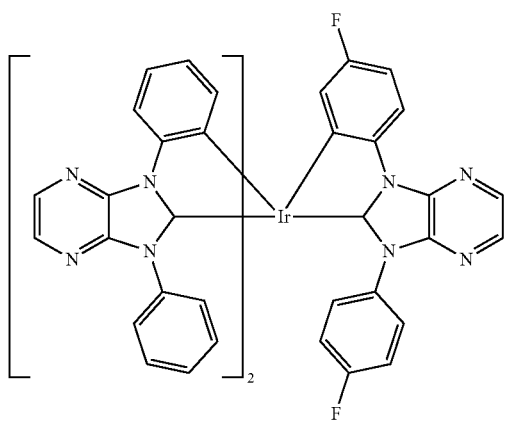
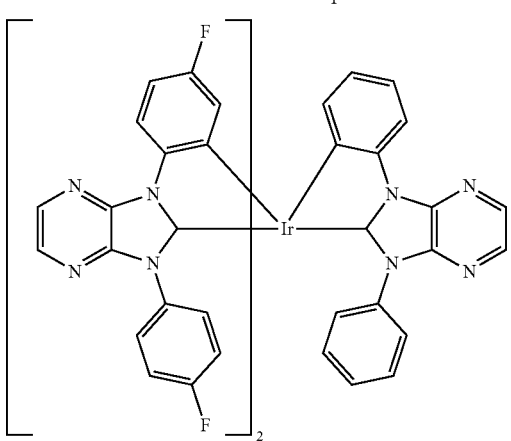
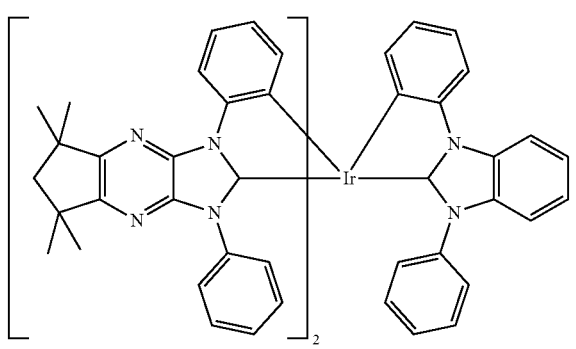
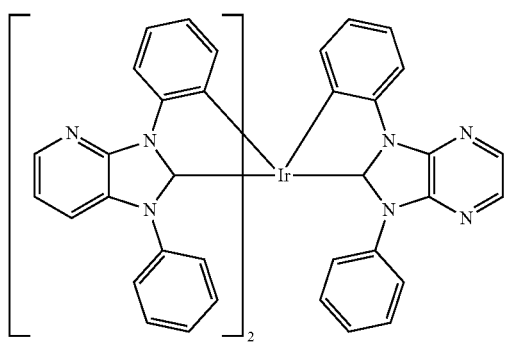

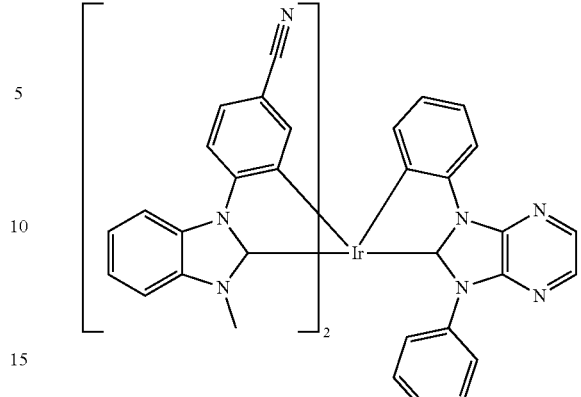
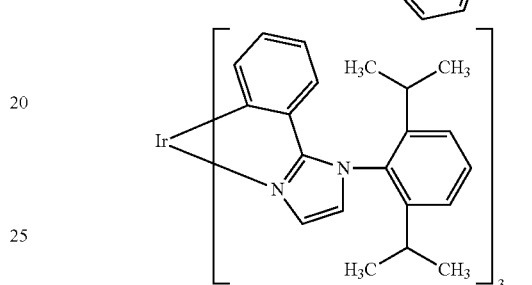
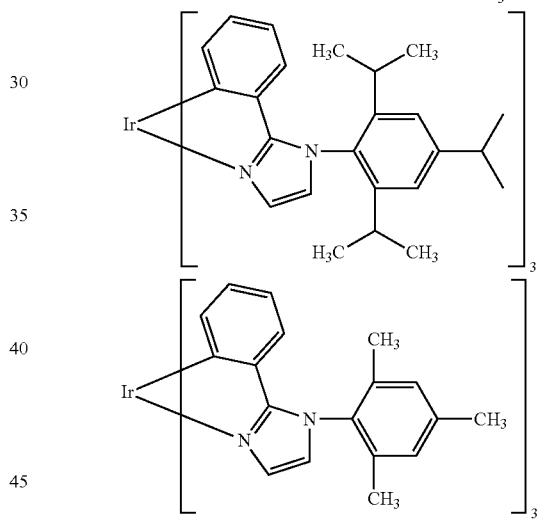
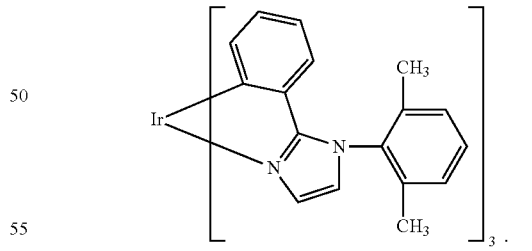

The homoleptic metal-carbene complexes may be present in the form of facial or meridional isomers, preference being given to the facial isomers.

In the case of the heteroleptic meta-carbene complexes, four different isomers may be present, preference being given to the pseudo-facial isomers.

The light-emitting layer may comprise further components in addition to the emitter material. For example, a fluroescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, be a small molecule, for example 4,4'-N,N'-dicarbazolebiphenyl (CDP=CBP) or tertiary aromatic amines, for example TCTA. In a preferred embodiment of the present invention, at least one compound of the formula I is used as matrix material.

In a preferred embodiment, the light-emitting layer is formed from 2 to 40% by weight, preferably 5 to 35% by weight, of at least one of the aforementioned emitter materials and 60 to 98% by weight, preferably 75 to 95% by weight, of at least one of the aforementioned matrix materials—in one embodiment at least one compound of the formula I—where the sum total of the emitter material and of the matrix material adds up to 100% by weight.

In particularly preferred embodiment, the light-emitting layer comprises a compound of formula I, such as, for example, (A-43)

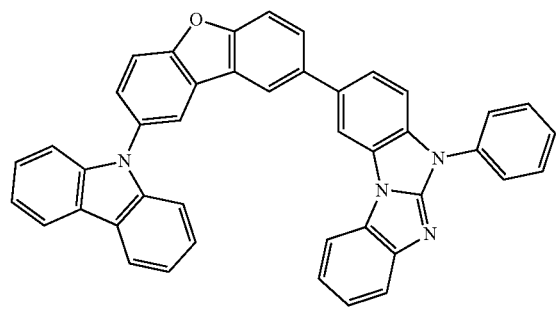

, and two carbene complexes, preferably of formula

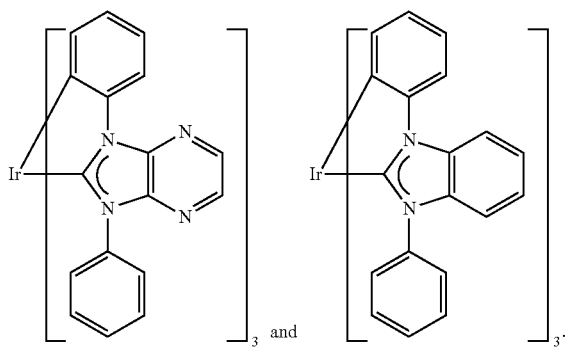

In said embodiment, the light-emitting layer is formed from 2 to 40% by weight, preferably 5 to 35% by weight, of

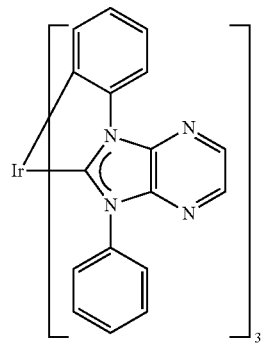

and 60 to 98% by weight, preferably 65 to 95% by weight, of a compound of the formula I and

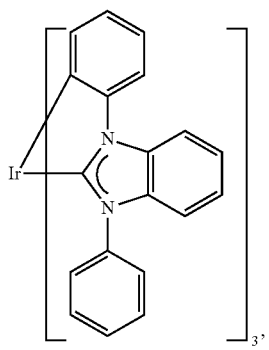

where the sum total of the carben complexes and of the compound of formula I adds up to 100% by weight.

Suitable metal complexes for use together with the compounds of the formula I as matrix material and/or hole/exciton blocker material and/or electron/exciton blocker material and/or hole injection material and/or electron injection material and/or hole conductor material and/or electron conductor material, preferably as matrix material and/or hole/exciton blocker material, in OLEDs are thus, for example, also carbene complexes as described in WO 2005/019373 A2, WO 2006/056418 A2, WO 2005/113704, WO 2007/115970, WO 2007/115981 and WO 2008/000727. Explicit reference is made here to the disclosure of the WO applications cited, and these disclosures shall be considered to be incorporated into the content of the present application.

If the blocking layer for holes/excitons (4) does not comprise any compounds of the formula I, the OLED has—if a blocking layer for holes is present—hole blocker materials typically used in OLEDs, such as 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato)aluminum(III) (BAlq), phenothiazine S,S-dioxide derivates and 1,3,5-tris(N-phenyl-2-benzylimidazolyl)benzene) (TPBI), TPBI also being suitable as electron-conducting material. Further suitable hole blockers and/or electron conductor materials are 2,2',2"-(1,3,5-benzenetriyl)tris(1-phenyl-1-H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazo-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazo-2-yl]-2, 2'-bipyridyl, 2-phenyl-9,10-di(naphthalene-2-yl)anthracene, 2,7-bis[2-(2,2'-bipyridin-6-yl)-1,3,4-oxadiazo-5-yl]-9,9-dimethylfluorene, 1,3-bis[2-(4-tert-butylphenyl)-1,3,4-oxadiazo-5-yl]benzene, 2-(naphthalene-2-yl)-4,7-diphenyl-1,10-phenanthroline, tris(2,4,6-trimethyl-3-(pyridin-3-yl)phenyl) borane, 2,9-bis(naphthalene-2-yl)-4,7-diphenyl-1,10-phenanthroline, 1-methyl-2-(4-(naphthalene-2-yl)phenyl)-1H-imidazo[4,5-f][1,10]phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications PCT/EP2008/058207 and PCT/EP2008/058106, which were yet to be published at the priority date of the present application, and disilyl compounds as disclosed in WO2008/034758, as a blocking layer for holes/excitons (4) or as matrix materials in the light-emitting layer (3).

Suitable electron conductor materials for the layer (5) of the inventive OLEDs comprise metals chelated to oxinoid compounds, such as 2,2',2"-(1,3,5-phenylene)tris[1-phenyl-1H-benzimidazole] (TPBI), tris(8-quinolinolato)aluminum (Alq$_3$), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), 8-hydroxyquinolinolatolithium (Liq), 4,7-diphenyl-1,10-phenanthroline (BPhen), bis(2-methyl-8-quinolinolato)-4-(phenylphenolato)aluminum (BAlq), 1,3-bis[2-(2,2'-bipyridin-6-yl)-1,3,4-oxadiazo-5-yl]benzene (Bpy-OXD), 6,6'-bis[5-(biphenyl-4-yl)-1,3,4-oxadiazo-2-yl]-2,2'-bipyridyl (BP-OXD-Bpy), 4-(naphthalen-1-yl)-3,5-diphenyl-4H-1,2,4-triazole (NTAZ), 2,9-bis(naphthalen-2-yl)-4,7-diphenyl-1,10-phenanthroline (NBphen), 2,7-bis[2-(2,2'-bipyridin-6-yl)-1,3,4-oxadiazo-5-yl]-9,9-dimethylfluorene (Bby-FOXD), 1,3-bis[2-(4-tert-butylphenyl)-1,3,4-oxadiazo-5-yl] benzene (OXD-7), tris(2,4,6-trimethyl-3-(pyridin-3-yl) phenyl)borane (3TPYMB), 1-methyl-2-(4-(naphthalen-2-yl) phenyl)-1H-imidazo[4,5-f][1,10]phenanthroline (2-NPIP), 2-phenyl-9,10-di(naphthalen-2-yl)anthracene (PADN), 2-(naphthalen-2-yl)-4,7-diphenyl-1,10-phenanthroline (HNBphen). The layer (5) may serve both to facilitate electron transport and as a buffer layer or barrier layer in order to prevent quenching of the exciton at the interfaces of the layers of the OLED. The layer (5) preferably improves the mobility of the electrons and reduces quenching of the exciton. In a preferred embodiment, TPBI is used as the electron conductor material. In another preferred embodiment, BCP is used as the electron conductor material. In principle, it is possible that the electron conductor layer comprises at least one compound of the formula I as electron conductor material.

Among the materials mentioned above as hole conductor materials and electron conductor materials, some may fulfil several functions. For example, some of the electron-conducting materials are simultaneously hole-blocking materials when they have a low-lying HOMO. These can be used, for example, in the blocking layer for holes/excitons (4). However, it is likewise possible that the function as a hole/exciton blocker is also adopted by the layer (5), such that the layer (4) can be dispensed with.

The charge transport layers can also be electronically doped in order to improve the transport properties of the materials used, in order firstly to make the layer thicknesses more generous (avoidance of pinholes/short circuits) and in order secondly to minimize the operating voltage of the device. For example, the hole conductor materials can be doped with electron acceptors; for example, phthalocyanines or arylamines such as TPD or TDTA can be doped with tetrafluorotetracyanquinodimethane (F4-TCNQ) or with $MoO_3$ or $WO_3$. The electron conductor materials can be doped, for example, with alkali metals, for example $Alq_3$ with lithium. In addition, electron conductors can be doped with salts such as $Cs_2CO_3$, or 8-hydroxyquinolatolithium (Liq). Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo. Appl. Phys. Lett., Vol. 82, No. 25, 23 Jun. 2003 and Pfeiffer et al., Organic Electronics 2003, 4, 89-103. For example, the hole conductor layer may, in addition to a carbene complex, e.g. Ir(dpbic)$_3$, be doped with $MoO_3$ or $WO_3$. For example, the electron conductor layer may comprise BCP doped with $Cs_2CO_3$.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the periodic table of the elements (old IUPAC version), comprising the lanthanides and actinides, for example samarium. In addition, it is also possible to use metals such as aluminum or indium, and combinations of all metals mentioned. In addition, alkali metal, especially lithium-comprising organometallic compounds, or alkali metal fluorides, such as, for example, LiF, CsF, or KF can be applied between the organic layer and the cathode in order to reduce the operating voltage.

The OLED according to the present invention may additionally comprise further layers which are known to those skilled in the art. For example, a layer which facilitates the transport of the positive charge and/or matches the band gaps of the layers to one another may be applied between the layer (2) and the light-emitting layer (3). Alternatively, this further layer may serve as a protective layer. In an analogous manner, additional layers may be present between the light-emitting layer (3) and the layer (4) in order to facilitate the transport of negative charge and/or to match the band gaps between the layers to one another. Alternatively, this layer may serve as a protective layer.

In a preferred embodiment, the inventive OLED, in addition to layers (1) to (6), comprises at least one of the following layers mentioned below:
  a hole injection layer between the anode (1) and the hole-transporting layer (2) having a thickness of 2 to 100 nm, preferably 5 to 50 nm;
  a blocking layer for electrons between the hole-transporting layer (2) and the light-emitting layer (3);
  an electron injection layer between the electron-transporting layer (5) and the cathode (6).

Materials for a hole injection layer may be selected from copper phthalocyanine, 4,4',4"-tris(N-3-methylphenyl-N-phenylamino)triphenylamine (m-MTDATA), 4,4',4"-tris(N-(2-naphthyl)-N-phenylamino)triphenylamine (2T-NATA), 4,4',4"-tris(N-(1-naphthyl)-N-phenylamino)triphenylamine (1T-NATA), 4,4',4"-tris(N,N-diphenylamino)triphenylamine (NATA), titanium oxide phthalocyanine, 2,3,5,6-tetrafluoro-7,7,8,8-tetracyanoquinodimethane (F4-TCNQ), pyrazino[2, 3-f][1,10]phenanthroline-2,3-dicarbonitrile (PPDN), N,N, N',N'-tetrakis(4-methoxyphenyl)benzidine (MeO-TPD), 2,7-bis[N,N-bis(4-methoxyphenyl)amino]-9,9-spirobifluorene (MeO-Spiro-TPD), 2,2'-bis[N,N-bis(4-methoxyphenyl)amino]-9,9-spirobifluorene (2,2'-MeO-Spiro-TPD), N,N'-diphenyl-N,N'-di-[4-(N,N-ditolylamino)phenyl]benzidine (NTNPB), N,N'-diphenyl-N,N'-di-[4-(N,N-diphenylamino)phenyl]benzidine (NPNPB), N,N'-di(naphthalen-2-yl)-N,N'-diphenylbenzene-1,4-diamine (α-NPP). In principle, it is possible that the hole injection layer comprises at least one compound of the formula I as hole injection material. In addition, polymeric hole-injection materials can be used such as poly(N-vinylcarbazole) (PVK), polythiophenes, polypyrrole, polyaniline, self-doping polymers, such as, for example, sulfonated poly(thiophene-3-[2[(2-methoxyethoxy)ethoxy]-2,5-diyl) (Plexcore® OC Conducting Inks commercially available from Plextronics), and copolymers such as poly(3,4-ethylenedioxythiophene)/poly(4-styrenesulfonate) also called PEDOT/PSS.

As a material for the electron injection layer, LiF, for example, can be selected. In principle, it is possible that the electron injection layer comprises at least one compound of the formula I as electron injection material.

The person skilled in the art is aware (for example on the basis of electrochemical studies) of how suitable materials have to be selected. Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

In general, the different layers have the following thicknesses: anode (1) 50 to 500 nm, preferably 100 to 200 nm; hole-conducting layer (2) 5 to 100 nm, preferably 20 to 80 nm, light-emitting layer (3) 1 to 100 nm, preferably 10 to 80 nm, blocking layer for holes/excitons (4) 2 to 100 nm, preferably 5 to 50 nm, electron-conducting layer (5) 5 to 100 nm, preferably 20 to 80 nm, cathode (6) 20 to 1000 nm, preferably 30 to 500 nm. The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer have greater thicknesses than the layer thicknesses specified when they are electrically doped.

Use of the compounds of the formula I in at least one layer of the OLED, preferably in the light-emitting layer (preferably as a matrix material) and/or in the blocking layer for holes/excitons makes it possible to obtain OLEDs with high efficiency and with low use and operating voltage. Frequently, the OLEDs obtained by the use of the compounds of the formula I additionally have high lifetimes. The efficiency of the OLEDs can additionally be improved by optimizing the other layers of the OLEDs. For example, high-efficiency cathodes such as Ca or Ba, if appropriate in combination with an intermediate layer of LiF, can be used. Shaped substrates and novel hole-transporting materials which bring about a reduction in the operating voltage or an increase in the quantum efficiency are likewise usable in the inventive OLEDs. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all apparatus in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, tablet PCs, laptops, digital cameras, MP3 players, vehicles and destination displays on buses and trains. Further devices in which the inventive OLEDs can be used are, for example, keyboards; items of clothing; furniture; wallpaper.

In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, tablet PCs, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer.

The following examples are included for illustrative purposes only and do not limit the scope of the claims. Unless otherwise stated, all parts and percentages are by weight.

EXAMPLES

Example 1

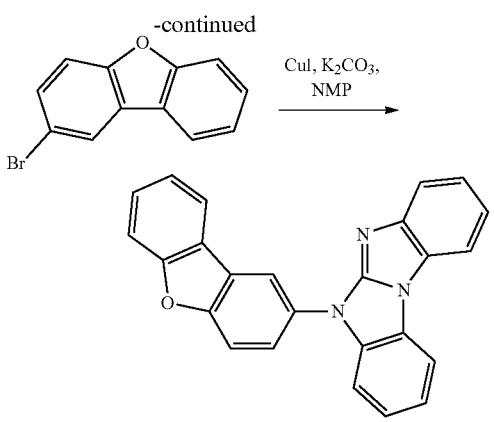

a) A mixture of 5.00 g (24.1 mmol) 6H-benzimidazolo[1,2-a]benzimidazole, 6.56 g (26.5 mmol) 2-bromodibenzofuran, 5.00 g (36.2 mmol) potassium carbonate and 920 mg (4.8 mmol) copper (I) iodide in 50 ml 1-methyl-2-pyrrolidon (NMP) are stirred under argon at 200° C. for 24 h. The reaction mixture is cooled to 20° C. and 100 ml dichloromethane are added. The reaction mixture is filtered on silica gel with dichloromethane. The organic phase is washed with water and is dried with magnesium sulfate. The solvent is distilled off. The product is decocted with methyl ethyl ketone (MEK) and filtered off. (yield: 2.50 g (28%)).

$^1$H NMR (400 MHz, DMSO-d6): δ 8.67 (s, 1H), 8.22-8.20 (m, 3H), 8.01 (s, 2H), 7.80 (d, J=8.3 Hz, 1H), 7.59-7.65 (m, 3H), 7.40-7.50 (m, 3H), 7.28-7.37 (m, 2H). MS (APCI (pos), m/z): 374 ($M^{+1}$).

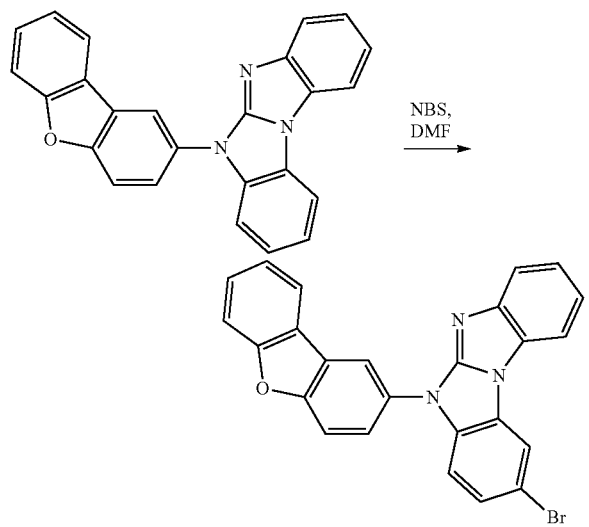

b) 3.00 g (8.03 mmol) 5-dibenzofuran-2-ylbenzimidazolo[1,2-a]benzimidazole is dissolved at 50° C. under argon in 15 ml DMF. 2.14 g (12.1 mmol) N-Bromosuccinimide is added. The reaction mixture is stirred under argon at 50° C. for 18 h. The precipitated product is filtered off and is washed with DMF, ethanol, water and again ethanol (yield: 2.85 g (78%)).

$^1$H NMR (400 MHz, THF-d8): δ 8.56 (d, J=2.1 Hz, 1H), 8.23 (d, J=1.9 Hz, 1H), 8.10-8.14 (m, 2H), 7.98 (dd, J=2.3 Hz, J=8.7 Hz, 1H), 7.83 (d, L=8.7 Hz, 1H), 7.64-7.70 (m, 2H), 7.51-7.56 (m, 2H), 7.36-7.43 (m, 4H).

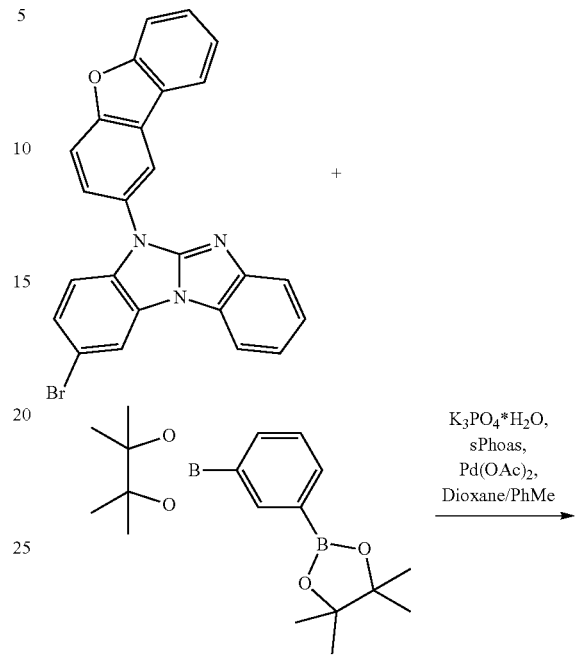

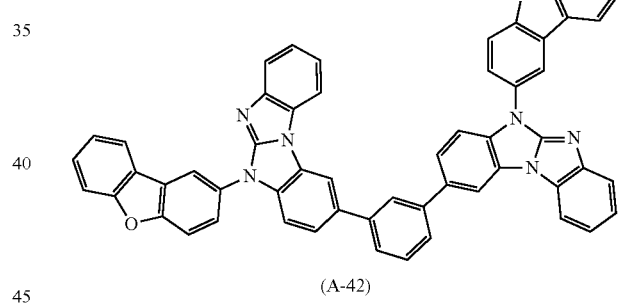

(A-42)

c) 1.50 g (3.32 mmol) 2-bromo-5-dibenzofuran-2-yl-benzimidazolo[1,2-a]benzimidazole, 1.50 g (1.59 mmol) 4,4,5,5-tetramethyl-2-[3-(4,4,5,5-tetramethyl-1,3,2-dioxaborolan-2-yl)phenyl]-1,3,2-dioxaborolane, 4.02 g (16.6 mmol) potassium phosphate tribasic monohydrate, 15 ml dioxane, 50 ml xylene and 10 ml water are degassed with argon. 82 mg (0.20 mmol) 2-dicyclohexylphosphino-2',6'-dimethoxybiphenyl (sPhos) and 7.4 mg (0.033 mmol) palladium (II) acetate are added. The reaction mixture is degassed with argon and is stirred for 22 h at 100° C. under argon. 40 ml of a 1% sodium cyanide solution are added and the reaction mixture is refluxed for 1 h, cooled to 20° C. and the product is filtered off. The product is washed with water and ethanol and decoded in MEK (yield: 1.05 g (38.5%)).

$^1$H NMR (400 MHz, TFA-d1): δ 8.54 (s, 2H), 8.41 (d, J=2.3 Hz, 2H), 8.37 (d, J=8.0 Hz, 2H) 8.07-8.19 (m, 6H), 7.927.95 (m, 4H), 7.68-7.88 (m, 14H), 7.54 (t, J=7.5 Hz, 2H). MS (APCI(pos), m/z): 821 ($M^{+1}$).

Example 2

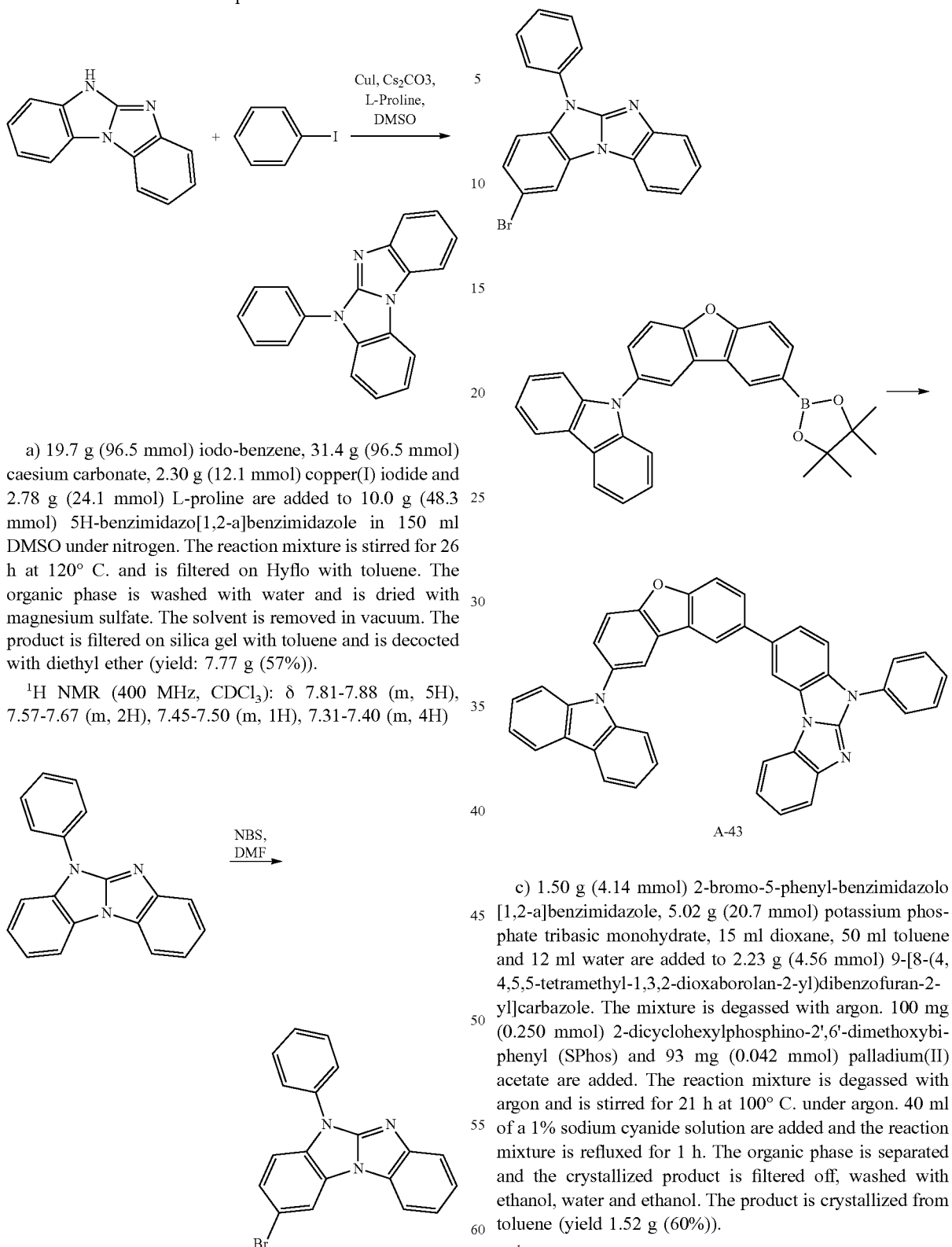

a) 19.7 g (96.5 mmol) iodo-benzene, 31.4 g (96.5 mmol) caesium carbonate, 2.30 g (12.1 mmol) copper(I) iodide and 2.78 g (24.1 mmol) L-proline are added to 10.0 g (48.3 mmol) 5H-benzimidazo[1,2-a]benzimidazole in 150 ml DMSO under nitrogen. The reaction mixture is stirred for 26 h at 120° C. and is filtered on Hyflo with toluene. The organic phase is washed with water and is dried with magnesium sulfate. The solvent is removed in vacuum. The product is filtered on silica gel with toluene and is decocted with diethyl ether (yield: 7.77 g (57%)).

$^1$H NMR (400 MHz, CDCl$_3$): δ 7.81-7.88 (m, 5H), 7.57-7.67 (m, 2H), 7.45-7.50 (m, 1H), 7.31-7.40 (m, 4H)

b) The reaction is carried out according to example 1 b).

$^1$H NMR (400 MHz, CDCl$_3$): δ 8.02 (d, J=1.7 Hz, 1H), 7.83-7.87 (m, 3H), 7.64-7.73 (m, 3H), 7.58-7.61 (m, 1H), 7.39-7.53 (m, 4H)

A-43 c) 1.50 g (4.14 mmol) 2-bromo-5-phenyl-benzimidazolo[1,2-a]benzimidazole, 5.02 g (20.7 mmol) potassium phosphate tribasic monohydrate, 15 ml dioxane, 50 ml toluene and 12 ml water are added to 2.23 g (4.56 mmol) 9-[8-(4,4,5,5-tetramethyl-1,3,2-dioxaborolan-2-yl)dibenzofuran-2-yl]carbazole. The mixture is degassed with argon. 100 mg (0.250 mmol) 2-dicyclohexylphosphino-2',6'-dimethoxybiphenyl (SPhos) and 93 mg (0.042 mmol) palladium(II) acetate are added. The reaction mixture is degassed with argon and is stirred for 21 h at 100° C. under argon. 40 ml of a 1% sodium cyanide solution are added and the reaction mixture is refluxed for 1 h. The organic phase is separated and the crystallized product is filtered off, washed with ethanol, water and ethanol. The product is crystallized from toluene (yield 1.52 g (60%)).

$^1$H NMR (400 MHz, THF-d8): δ=8.53 (d, J=1.7 Hz, 1H), 8.40 (d, J=1.7 Hz, 1H), 8.37 (s, 1H), 8.20 (s, 1H), 8.17 (s, 1H), 8.11-8.14 (m, 1H), 7.98-8.03 (m, 3H), 7.90 (d, J=8.5 Hz, 1H), 7.78 (d, J=8.6 Hz, 1H), 7.67-7.73 (m, 4H), 7.60-7.64 (m, 2H), 7.33-7.44 (m, 4H), 7.33-7.37 (m, 2H), 7.24-7.28 (m, 2H) MS (APCI(pos), m/z): 615 (M$^{+1}$).

Example 3

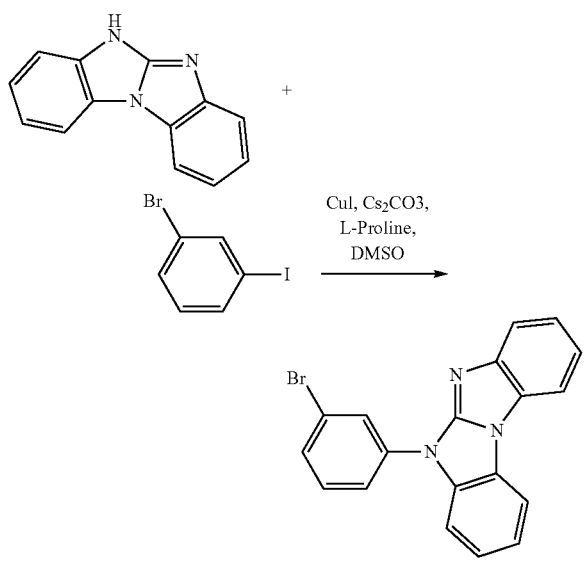

a) 7.78 g (25 mmol) 1-bromo-3-iodo-benzene, 16.3 g (50.0 mmol) caesium carbonate, 1.24 g (6.50 mmol) copper (I) iodide and 1.50 g (13.0 mmol) L-proline are added to 5.18 g (25.0 mmol) mmol) 5H-benzimidazo[1,2-a]benzimidazole in 100 ml dimethylsulfoxide (DMSO) under nitrogen. The reaction mixture is stirred for 18 h at 100° C. and poured into water. The organic phase is extracted with dichloromethane and dried with magnesium sulfate. The solvent is distilled off. Column chromatography on silica gel with toluene gives the product (yield 8.35 g (92%)).

$^1$H NMR (400 MHz, CDCl$_3$): δ 8.54 (d, J=2.1 Hz, 1H), 8.37-8.40 (m, 1H), 8.16-8.199 (m, 1H), 7.93-7.95 (m, 1H), 7.60-7.74 (m, 4H), 7.41-7.7.50 (m, 3H). MS (APCI(pos), m/z): 444 (M$^{+1}$) 442 (M$^{+1}$), 441 (M$^{+1}$)

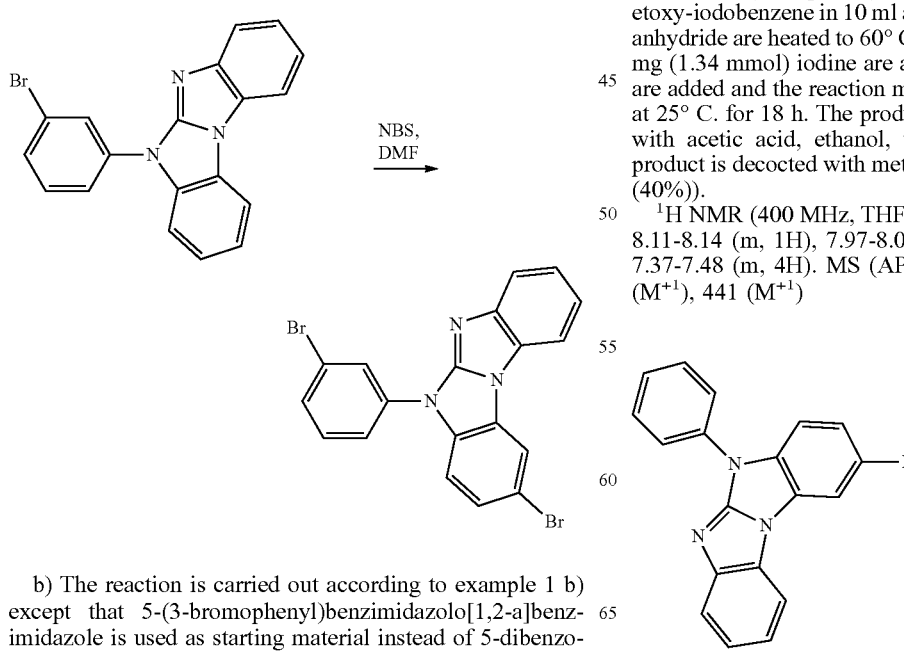

b) The reaction is carried out according to example 1 b) except that 5-(3-bromophenyl)benzimidazolo[1,2-a]benzimidazole is used as starting material instead of 5-dibenzofuran-2-ylbenzimidazolo[1,2-a]benzimidazole.

$^1$H NMR (400 MHz, CDCl$_3$): δ 8.54 (d, J=2.1 Hz, 1H), 8.37-8.40 (m, 1H), 8.16-8.199 (m, 1H), 7.93-7.95 (m, 1H), 7.60-7.74 (m, 4H), 7.41-7.7.50 (m, 3H). MS (APCI(pos), m/z): 444 (M$^{+1}$), 442 (M$^{+1}$), 441 (M$^{+1}$).

Example 4

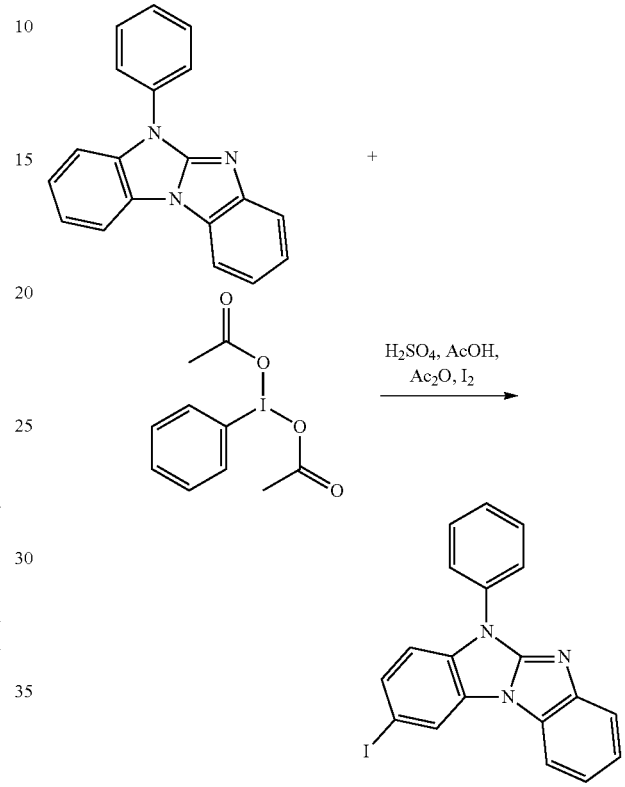

a) 1.00 g (3.53 mmol) 5-phenylbenzimidazolo[1,2-a]benzimidazole (example 2a) and 850 mg (2.65 mmol) diacetoxy-iodobenzene in 10 ml acetic acid and 10 ml acetic acid anhydride are heated to 60° C. and then cooled to 25° C. 340 mg (1.34 mmol) iodine are added. 10 drops of sulfuric acid are added and the reaction mixture is stireed under nitrogen at 25° C. for 18 h. The product is filtered off and is washed with acetic acid, ethanol, water and again ethanol. The product is decocted with methyl ethyl ketone (yield: 560 mg (40%)).

$^1$H NMR (400 MHz, THF-d8): δ=8.39 (d, J=1.6 Hz, 1H), 8.11-8.14 (m, 1H), 7.97-8.00 (m, 2H), 7.61-7.71 (m, 4H), 7.37-7.48 (m, 4H). MS (APCI(pos), m/z): 444 (M$^{+1}$), 442 (M$^{+1}$), 441 (M$^{+1}$)

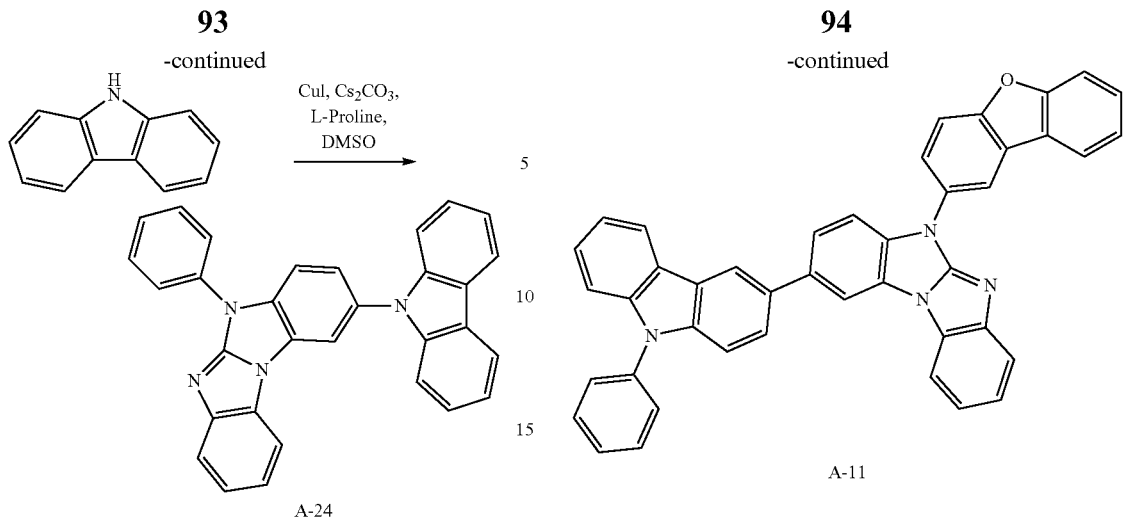

A-24

A-11 b) 750 mg (2.01 mmol) 2-iodo-5-phenyl-benzimidazolo[1,2-a]benzimidazole, 1.31 g (4.02 mmol) caesium carbonate, 77 mg (0.40 mmol) copper(I) iodide and 93 mg (0.80 mmol) L-proline are added to 460 mg (221 mmol) carbazole in 10 ml dimethylsulfoxide (DMSO) under nitrogen. The reaction mixture is stirred for 23 h at 120° C. under nitrogen, poured into water and the product is filtered off. Column chromatography on silica gel with toluene, than toluene/ethyl acetate results in the product.

$^1$H NMR (400 MHz, THF-d8): δ=8.30 (d, J=2.0 Hz, 1H), 8.21 (d, J=7.8 Hz, 2H), 8.03-8.11 (m, 3H), 7.90 (d, J=8.5 Hz, 1H), 7.67-7.91 (m, 3H), 7.47-7.55 (m, 2H), 7.33-7.42 (m, 6H), 7.25-7.29 (m, 2H).

The synthesis of 9-phenyl-3-(4,4,5,5-tetramethyl-1,3,2-dioxaborolan-2-yl)carbazole is described in WO2012/023947A1. 1.30 g (2.87 mmol) 2-bromo-5-dibenzofuran-2-yl-benzimidazolo[1,2-a]benzimidazole (example 1c)), 3.21 g (14.4 mmol) potassium phosphate tribasic monohydrate, 15 ml dioxane, 50 ml toluene and 10 ml water are added to 1.48 g (3.45 mmol) 9-phenyl-3-(4,4,5,5-tetramethyl-1,3,2-dioxaborolan-2-yl)carbazole. The mixture is degassed with argon. 71 mg (0.17 mmol) 2-dicyclohexylphosphino-2',6'-dimethoxybiphenyl (SPhos) and 65 mg (0.029 mmol) palladium(II) acetate are added. The reaction mixture is degassed with argon and is stirred for 6 h at 100° C. under argon. 40 ml of a 1% sodium cyanide solution are added and the reaction mixture is refluxed for 1 h. The water phase is extracted with dichloromethane and washed with 20% HCl. The organic phase is dried with magnesium sulfate and the solvent is distilled off. Column chromatography on silica gel with toluene gives the product. MS (APCI(pos), m/z): 615 ($M^{+1}$).

Example 5

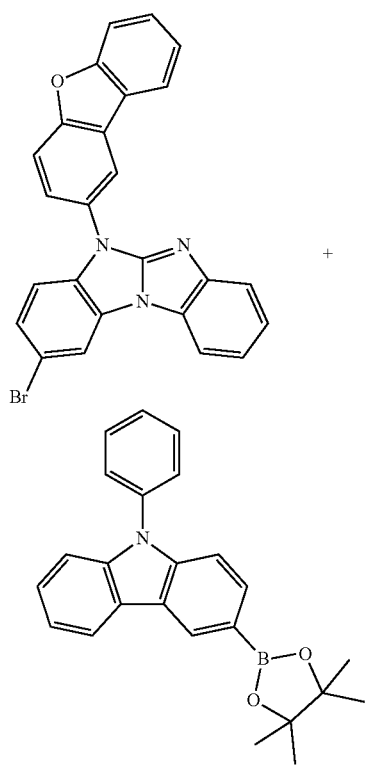

Example 6

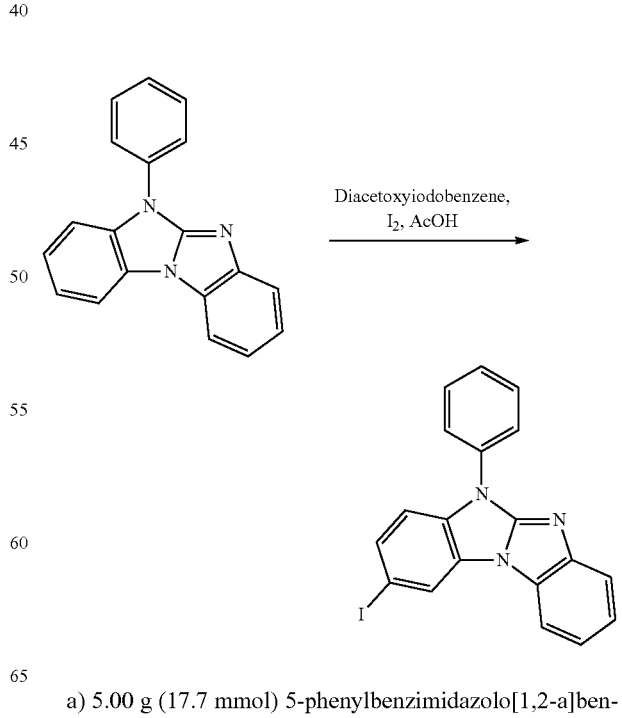

a) 5.00 g (17.7 mmol) 5-phenylbenzimidazolo[1,2-a]benzimidazole, 5.12 g (15.9 mmol) (diacetoxyido)benzene and 4.03 g (15.9 mmol) Iodine are stirred at 25° C. for 28 h. The reaction mixture is poured into a 10% sodium hydrosulfite solution. The product is filtered off, washed with water and ethanol, decocted with diethyl ether, filtered off, washed with ether and decocted with methyl ethyl ketone (MEK) (yield: 5.67 g (87%)).

are stirred under nitrogen at 20° C. After 5 h the product is filtered off. The product is crystalized from 900 ml ethanol using 2 g charcoal. The ethanol solution is filtered hot. The ethanol solution is cooled to 20° C. and the product is filtered off (yield: 59.5 g (44%)).

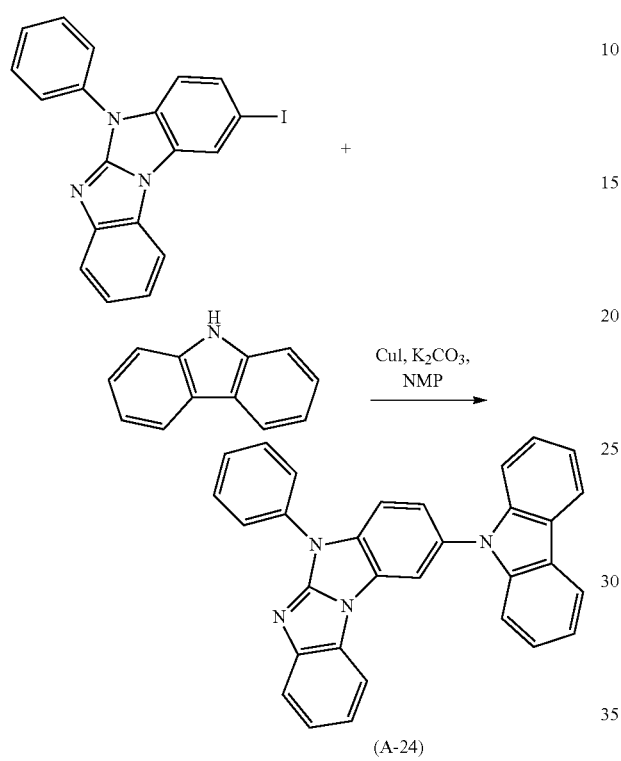

(A-24)

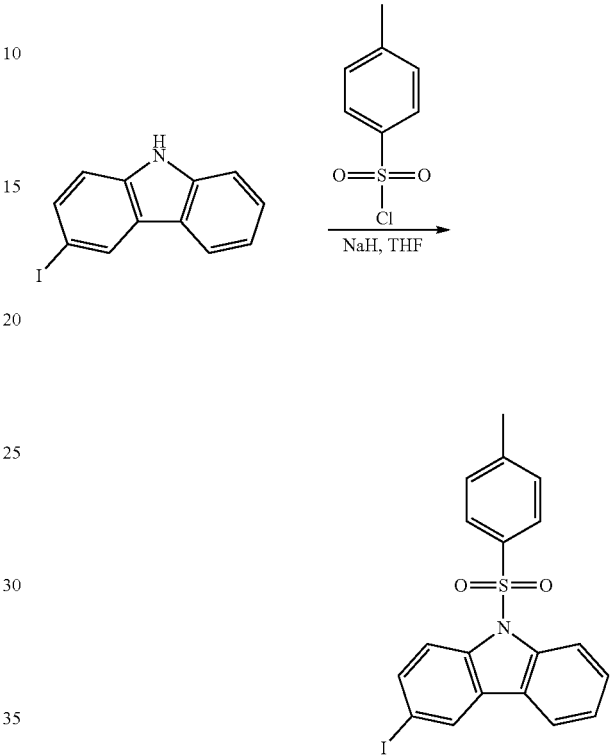

b) 5.00 g (12.2 mmol) 2-iodo-5-phenyl-benzimidazolo[1,2-a]benzimidazole, 2.25 g (13.4 mmol) carbazole, 2.53 g (18.3 mmol) potassium carbonate and 470 mg (2.44 mmol) copper iodide in 150 ml NMP are stirred under nitrogen at 200° C. for 25 h. The solvent is distilled off. Dichloromethane is added and the organic phase is washed with water, 30% NaOH, water and a 1M solution of 1amino-1-propanol in water. The organic phase is dried with magnesium sulfate and is filtered on silica gel. Column chromatography on silica gel with toluene/ethyl acetate 100/1 gives the product (yield: 4.21 g (77%)).

$^1$H NMR (400 MHz, THF-d8): δ=8.30 (d, J=2.0 Hz, 1H), 8.21 (d, J=7.8 Hz, 2H), 8.03-8.11 (m, 3H), 7.90 (d, J=8.5 Hz, 1H), 7.67-7.91 (m, 3H), 7.47-7.55 (m, 2H), 7.33-7.42 (m, 6H), 7.25-7.29 (m, 2H).

b) 19.7 g (67.0 mmol) 3-iodo-9H-carbazole and 2.95 g (73.7 mmol) sodium hydride 60% dispersion in mineral oil in 500 ml tetrahydrofuran (THF) is stirred at 50° C. under nitrogen for 1 h. 12.8 g (67.0 mmol) 4-methylbenzenesulfonyl chloride in 100 ml THF are added at 20° C. The reaction mixture is stirred for 1 h at 20° C. and is then stirred for 1 h at 50° C. The solution is filtered and the solvent is distilled off. 200 ml ethyl acetate are added and the organic phase is washed with a solution of citric acid, sodium hydrogen carbonate and water. The solvent is partly removed until the product starts to crystalize. The product is filtered off and washed with methanol (yield: 23 g (79%)).

Example 7

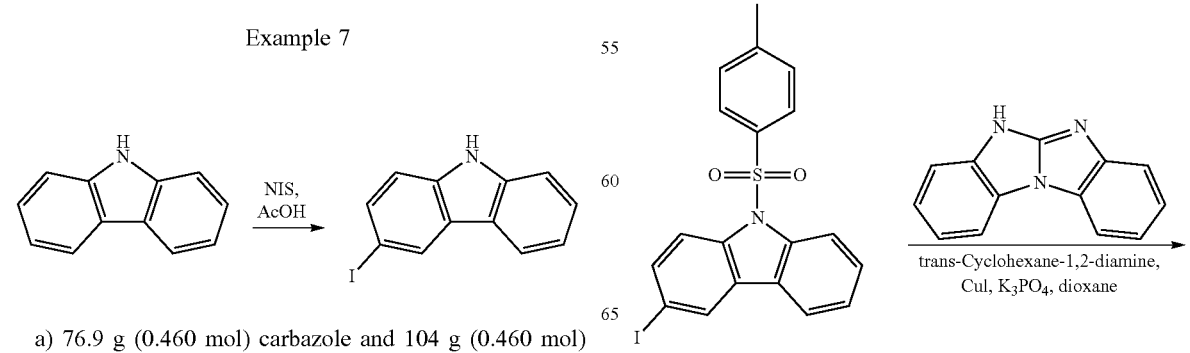

a) 76.9 g (0.460 mol) carbazole and 104 g (0.460 mol) 1-iodopyrrolidine-2,5-dione (NIS) in 100 m ml acetic acid -continued

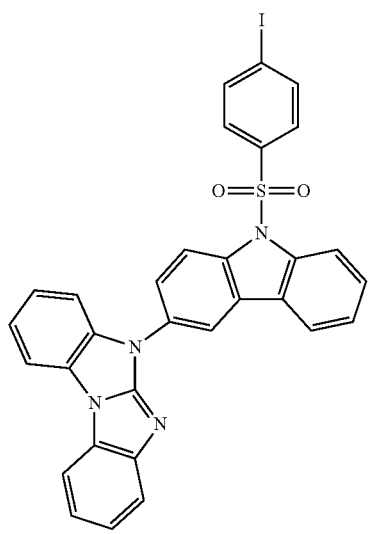

c) 36.0 g (174 mmol) 6H-benzimidazolo[1,2-a]benzimidazole, 77.8 (174 mmol) 3-iodo-9-(p-tolylsulfonyl) carbazole, 106 g (0.500 mol) potassium phosphate, 5.5 g (28.9 mmol) copper iodide, and 111 g (0.972 mol) trans-cyclohexane-1.2-diamime in 900 ml dioxane are stirred at 100° C. 48 h under nitrogen. The product is filtered off, washed with dioxane, and ethanol and is used without purification in the next reaction step.

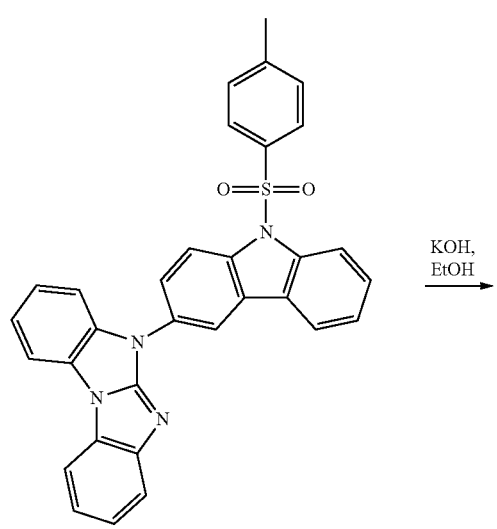

KOH, EtOH →

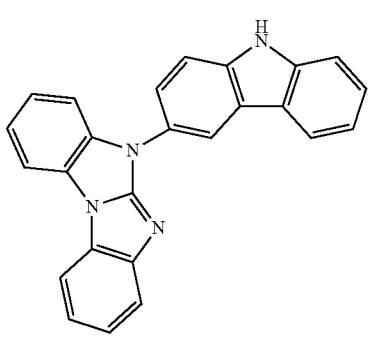

d) A solution of 11.3 g (202 mmol) potassium hydroxide in 500 ml ethanol is added under nitrogen within 5 minutes to 53 g (101 mmol) 5-[9-(p-tolylsulfonyl)carbazol-3-yl] benzimidazolo[1,2-a]benzimidazole in 500 ml boiling ethanol. After 5 h the product is filtered off and is washed with ethanol, water and methanol (yield: 32 g (85.4%)). $^1$H NMR (400 MHz, DMSO-d6): δ 11.6 (s, 1H), 8.57 (d, J=7.8 Hz, 1H), 8.22-8.28 (m, 3H), 7.74-7.82 (m, 2H), 7.57-7.62 (m, 2H), 7.38-7.54 (m, 4H), 7.27-7.34 (m, 2H), 7.20-7.24 (m, 1H).

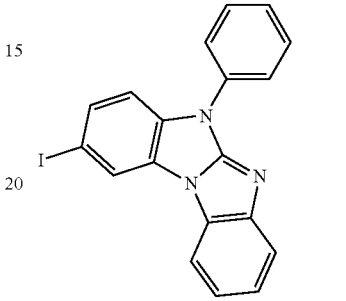

+

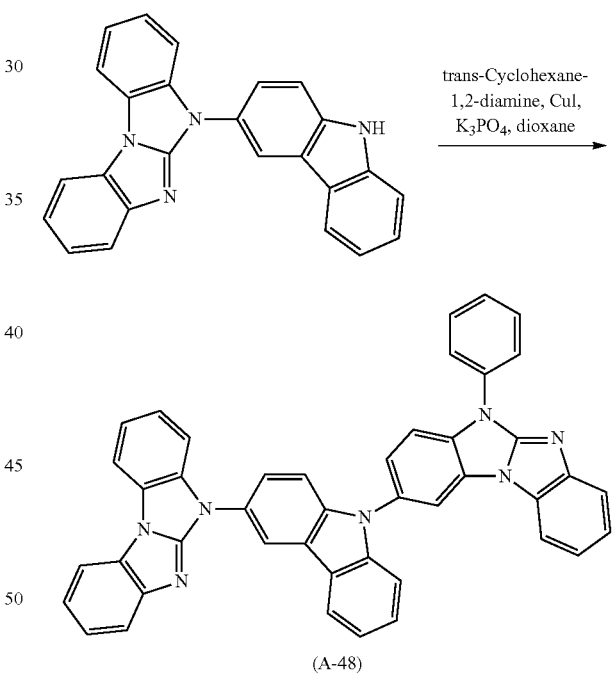

(A-48)

trans-Cyclohexane-1,2-diamine, CuI, K₃PO₄, dioxane → e) 480 mg (1.29 mmol) 5-(9H-carbazol-3-yl)benzimidazolo[1,2-a]benzimidazole, 530 mg (1.29 mmol) 2-iodo-5-phenyl-benzimidazolo[1,2-a]benzimidazole, 100 mg (0.525 mmol) copper iodide, 1.06 g (5.00 mmol) potassium phosphate and 1.00 g (8.76 mmol) trans-cyclohexane-1.2-diamine in 10 ml dioxane are refluxed under nitrogen for 6 h. The product is filtered off and is washed with dioxane and then methanol (yield: 440 mg (52%)). $^1$H NMR (400 MHz, CDCl₃): δ 8.54 (d, J=1.9 Hz, 1H), 8.23 (d, J=7.8 Hz, 1H), 8.02-8.07 (m, 2H), 7.88-7.93 (m, 4H), 7.80-7.85 (m, 3H), 7.48-7.72 (m, 9H), 7.31-7.43 (m, 7H)

Example 8

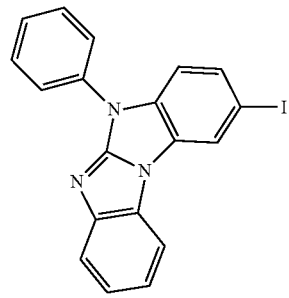

+

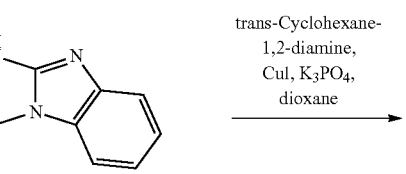

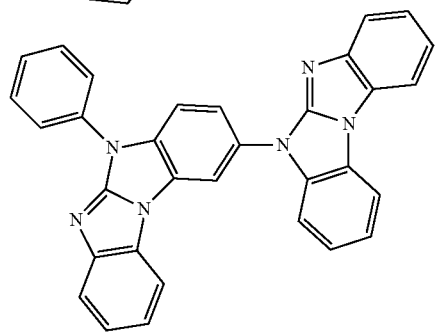

(A-46)

1.00 g (2.44 mmol) 2-iodo-5-phenyl-benzimidazolo[1,2-a]benzimidazole, 610 mg (2.93 mmol) 6H-benzimidazolo[1,2-a]benzimidazole, 93 mg (0.49 mmol) copper iodide, 1.59 g (4.489 mmol) caesium carbonate and 113 mg (0.98 mmol) L-proline in 10 ml DMSO are stirred at 150° C. under nitrogen for 43 h. The reaction mixture is poured into water and the product is filtered off. The product is washed with water. Column chromatography on silica gel with toluene/ethyl acetate 19/1 ant than 1/1 gives the product (yield: 220 mg (18%)). $^1$H NMR (400 MHz, THF-d8): δ 8.59 (d, J=1.8 Hz, 1H), 8.06-8.13 (m, 1H), 8.00-8.06 (m, 4H), 7.81-7.87 (m, 1H), 7.75-7.81 (m, 1H), 7.72-7.74 (m, 1H), 7.50-7.69 (m, 4H), 7.43-7.49 (m, 1H), 7.31-7.42 (m, 4H), 7.24-7.30 (m, 2H). MS (APCI(pos), m/z): 489 ($M^{+1}$),

Example 9

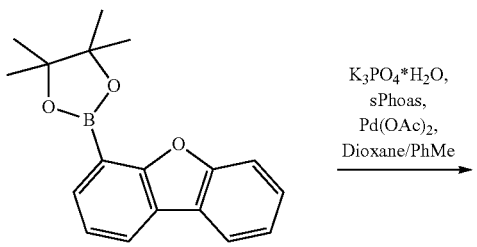

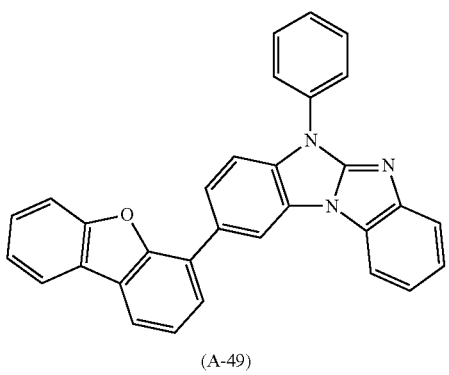

(A-49)

1.00 g (2.76 mmol) 2-bromo-5-phenyl-benzimidazolo[1,2-a]benzimidazole, 1.15 g (3.31 mmol) 2-dibenzofuran-4-yl-4,4,5,5-tetramethyl-1,3,2-dioxaborolane, 1.91 g (13.8 mmol) potassium carbonate, 10 ml dioxane, 30 ml xylene and 7 ml water are degassed with argon. 23 mg (0.055 mmol) 2-dicyclohexylphosphino-2',6'-dimethoxybiphenyl (sPhos) and 6.2 mg (0.028 mmol) palladium(II) acetate are added. The reaction mixture is degassed with argon and is stirred for 21 h at 120° C. under argon. 40 ml of a 1% sodium cyanide solution are added and the reaction mixture is refluxed for 1 h. Dichloromethane is added and the organic phase is separated. The organic phase is dried with magnesium sulfate and the solvent is distilled off. The product is decocted in toluene, filtered off and washed with toluene (yield: 0.91 g (73%)). $^1$H NMR (400 MHz, CDCl$_3$): δ 8.45 (d, J=1.0 Hz, 1H), 8.04-8.07 (m, 1H), 7.99-8.00 (m, 6H), 7.74-7.76 (m, 1H), 7.66-7.71 (m, 3H), 7.61-7.64 (m, 1H), 7.49-7.54 (m, 3H), 7.38-7.47 (m, 3H).

Example 10

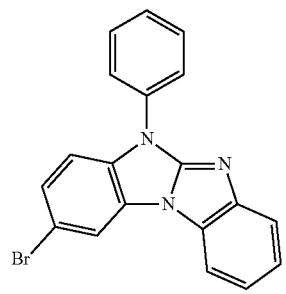

+

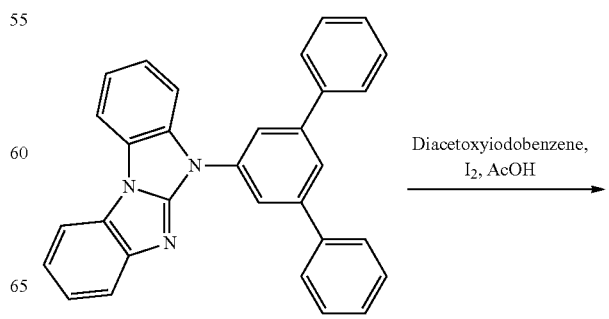

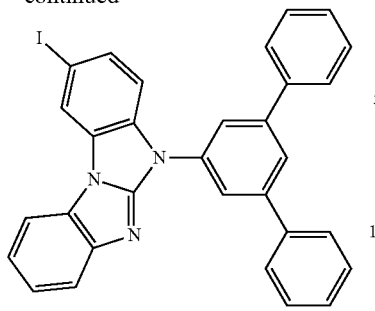

a) 4.70 g (10.8 mmol) 5-(3,5-diphenylphenyl)benzimidazolo[1,2-a]benzimidazole, 3.30 g (15.9 mmol) (diacetoxyido)benzne and 2.60 g (10.3 mmol) iodine are stirred at 25° C. for 18 h. The reaction mixture is poured into a 10% sodium hydrosulfite solution. The product is filtered off, washed with water and ethanol, decocted with t-butylmethylether, filtered off and washed with t-butylmethylether (yield: 5.64 g (98%)). $^1$H NMR (400 MHz, DMSO-d6): δ 8.62 (d, J=1.6 Hz, 1H), 8.36-8.38 (m, 1H), 8.133 (s, 1H), 8.129 (s, 1H), 8.01-8.02 (m, 1H), 7.87-7.89 (m, 4H), 7.75-7.78 (m, 1H), 7.59-7.61 (m, 1H), 7.51-7.56 (m, 4H), 7.43-7.47 (m, 5H).

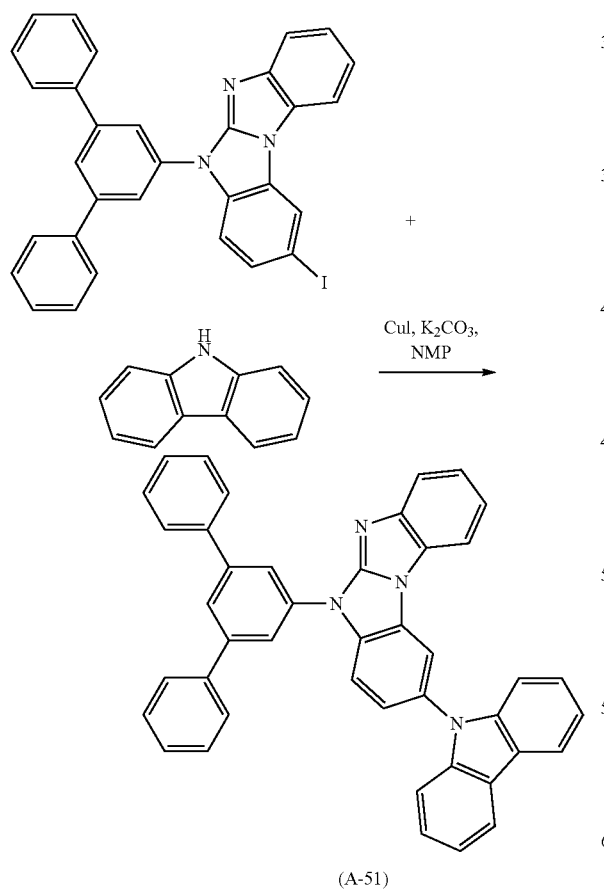

(A-51)

b) Example 6b) is repeated, except that instead of 2-iodo-5-phenyl-benzimidazolo[1,2-a]benzimidazole the product of Example 10a) is used. $^1$H NMR (400 MHz, DMSO-d6): δ 8.32 (d, J=1.8 Hz, 1H), 8.29 (d, J=1.6 Hz, 2H), 8.20-8.22 (m, 2H), 8.11-8.13 (m, 1H), 8.04-8.05 (m, 1H), 7.85-7.95 (m, 6H), 7.52-7.57 (m, 5H), 7.36-7.47 (m, 8H), 7.25-7.30 (m, 2H).

Example 11

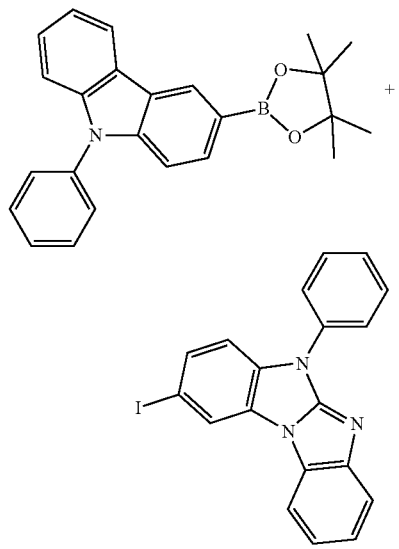

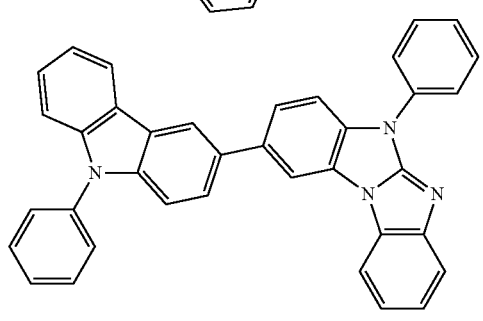

(A-47)

Example 6b) is repeated, except that instead of 2-dibenzofuran-4-yl-4,4,5,5-tetramethyl-1,3,2-dioxaborolane 9-phenyl-3-(4,4,5,5-tetramethyl-1,3,2-dioxaborolan-2-yl)carbazole is used. $^1$H NMR (400 MHz, THF-d8): δ 8.62 (d, J=1.6 Hz, 1H), 8.40 (s, 1H), 8.31 (d, J=7.7 Hz, 1H), 8.20 (d, J=7.3 Hz, 1H), 8.05 (d, J=7.7, 2H), 7.88 (dd, J=1.6 Hz, 8.4 Hz, 1H), 7.64-7.78 (m, 9H), 7.37-7.56 (m, 7H), 7.29-7.33 (m, 1H). MS (APCI(pos), m/z): 525 (M$^{+1}$).

Application Example 1

The ITO substrate used as the anode is first cleaned with an acetone/isopropanol mixture in an ultrasound bath. To eliminate any possible organic residues, the substrate is exposed to a continuous ozone flow in an ozone oven for further 25 minutes. This treatment also improves the hole injection properties of the ITO. Then Plexcore® OC AJ20-1000 (commercially available from Plextronics Inc.) is spin-coated and dried to form a hole injection layer (~40 nm).

Thereafter, the organic materials specified below are applied by vapor deposition to the clean substrate at a rate of approx. 0.5-5 nm/min at about $10^{-7}$-$10^{-9}$ mbar. As a hole transport and exciton blocker,

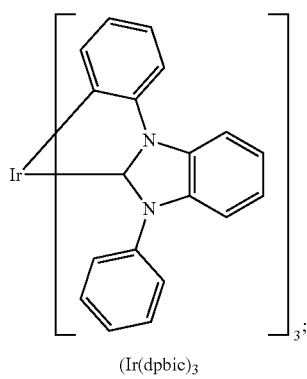

(Ir(dpbic)₃)

for preparation, see Ir complex (7) in the application WO2005/019373), is applied to the substrate with a thickness of 20 nm, wherein the first 10 nm are doped with MoO$_x$ (~10%) to improve the conductivity.

Subsequently, a mixture of 10% by weight of emitter compound,

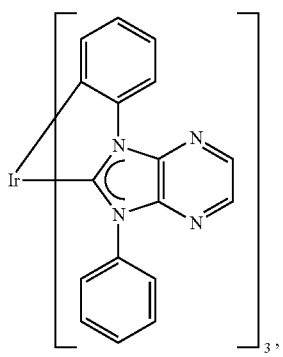

(A-43)

5% by weight of compound Ir(dpbic)₃ and 85% by weight of compound

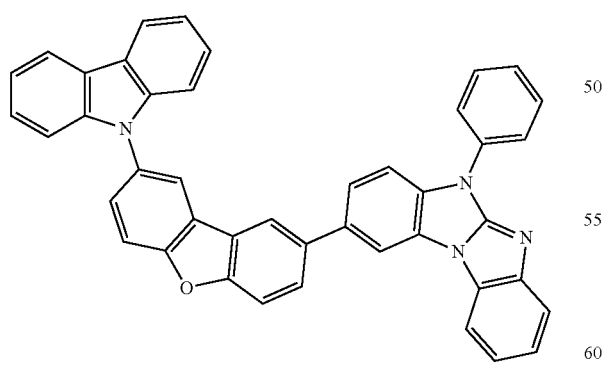

is applied by vapor deposition in a thickness of 40 nm. Subsequently, material (A-43) is applied by vapour deposition with a thickness of 5 nm as blocker. Thereafter, a 20 nm thick electron transport layer is deposited consisting of 50% by weight of

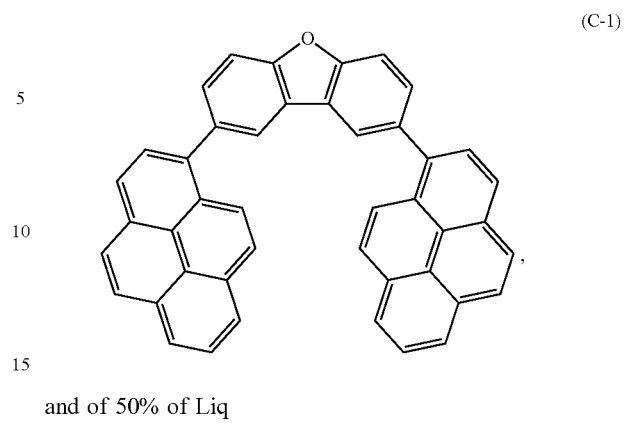

(C-1)

and of 50% of Liq

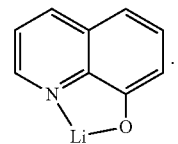

Finally a 2 nm KF layer serves as an electron injection layer and a 100 nm-thick Al electrode completes the device.

All fabricated parts are sealed with a glass lid and a getter in an inert nitrogen atmosphere. To characterize the OLED, electroluminescence spectra are recorded at various currents and voltages. In addition, the current-voltage characteristic is measured in combination with the light output emitted. The light output can be converted to photometric parameters by calibration with a photometer.

|  | Voltage @ 300 nits [V] | EQE[1] @ 300 nits [%] | CIE |
| --- | --- | --- | --- |
| Appl. Ex. 1 | 6.5 V | 7% | 0.17 0.31 |

[1]External quantum efficiency (EQE) is # of generated photons escaped from a substance or a device/# of electrons flowing through it.

Application Example 2

The substrate treatment is accomplished as in example 1.

Thereafter, the organic materials specified below are applied by vapor deposition to the clean substrate at a rate of approx. 0.5-5 nm/min at about $10^{-7}$-$10^{-9}$ mbar. As a hole transport and exciton blocker,

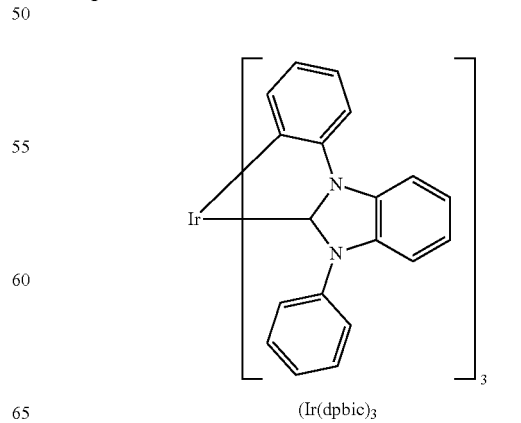

(Ir(dpbic)₃)

for preparation, see Ir complex (7) in the application WO02005/019373), is applied to the substrate with a thickness of 20 nm, wherein the first 10 nm are doped with MoO$_x$ (~10%) to improve the conductivity. Subsequently, a mixture of 10% by weight of emitter compound,

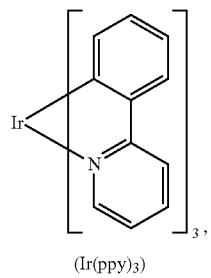

(Ir(ppy)$_3$)

5% by weight of compound Ir(dpbic)$_3$ and 85% by weight of compound (A-43) is applied by vapor deposition in a thickness of 40 nm. Subsequently, material (A-43) is applied by vapour deposition with a thickness of 5 nm as blocker. Thereafter, a 20 nm thick electron transport layer is deposited consisting of 50% by weight of compound (C-1) and of 50% of Liq. Finally a 2 nm KF layer serves as an electron injection layer and a 100 nm-thick Al electrode completes the device.

All fabricated parts are sealed with a glass lid and a getter in an inert nitrogen atmosphere. The characterization of the device is performed as in example 1.

|  | Voltage @ 300 nits [V] | EQE[1] @ 300 nits [%] | CIE |
|---|---|---|---|
| Appl. Ex. 2 | 4.05 V | 11.2% | 0.35/0.60 |

[1]External quantum efficiency (EQE) is # of generated photons escaped from a substance or a device/# of electrons flowing through it.

Application Example 3

The sample preparation for PL measurements is performed at ambient conditions by solution processing. Therefore, 96% by weight of compound (A-24)

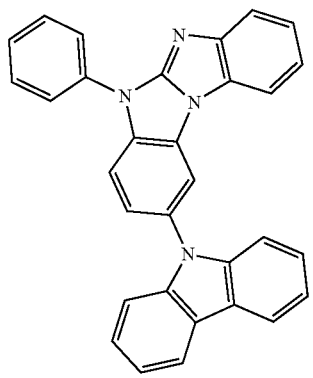

and 4% by weight of compound

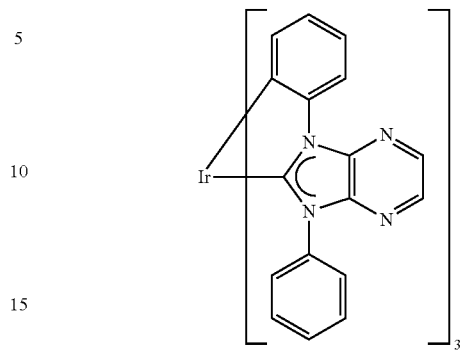

are dissolved in methylenchloride and deposited onto a quartz substrate by doctor blading.

The PL spectrum and the PL quantum efficiency are measured using an absolute quantum-yield measurement system "Quantaurus" (from Hamamatsu, Japan) at room temperature at an excitation wavelength of 370 nm.

|  | PLQE [%] | CIE |
|---|---|---|
| Appl. Ex. 3 | 76.8% | 0.15/0.24 |

Comparative Application Example 1

The device fabrication is done as in Application Example 1 except that compound (A-43) is replaced by compound (V-1)

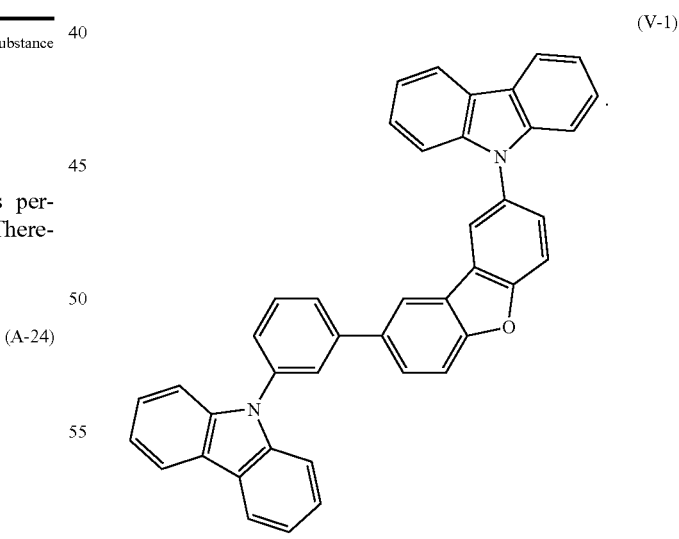

Application Example 4

The device is fabricated as in Comparative Application Example 1 except that in the emissive layer compound V-1 is replaced by compound

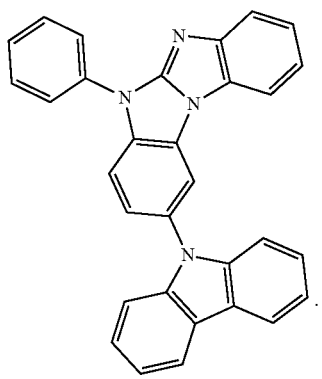

(A-24)

The table below cleary demonstrates that compound A-24 leads as compared to compound V-1 to a reduced voltage and a significantly blue shifted colour at comparable quantum efficiency.

| | Host | Voltage @ 300 nits [V] | EQE[1] @ 300 nits [%] | CIE |
|---|---|---|---|---|
| Comp. Appl. Ex. 1 | V-1 | 5.44 | 13.51 | 0.302 |
| Appl. Ex. 4 | A-24 | 5.04 | 13.39 | 0.272 |

Application Example 5

The substrate treatment is accomplished as in Application Example 1.

Thereafter, the organic materials specified below are applied by vapor deposition to the clean substrate at a rate of approx. 0.5-5 nm/min at about $10^{-7}$-$10^{-9}$ mbar.

First a 10 nm thick hole transport layer,

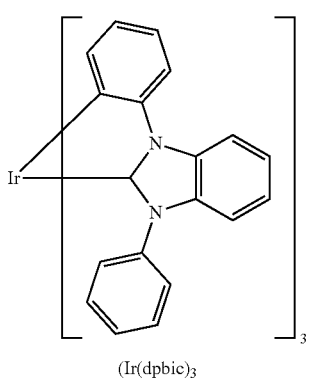

(Ir(dpbic)₃)

is deposited onto the substrate which is doped with MoO$_x$ (~10%) to improve the conductivity. Material

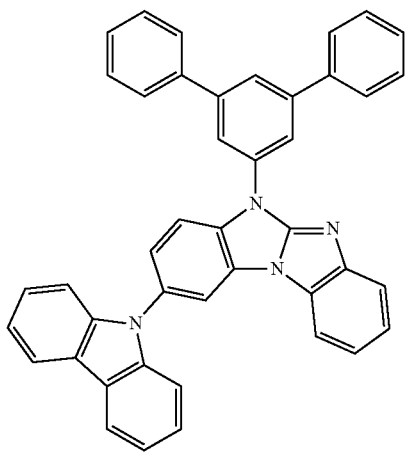

(A-51)

is deposited subsequently with 10 nm thickness as a blocker.

Then, a mixture of 10% by weight of emitter compound,

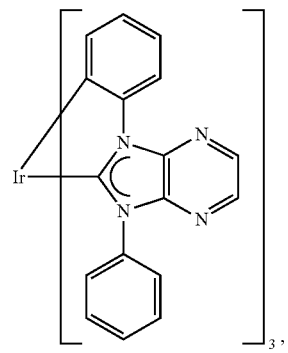

5% by weight of compound Ir(dpbic)₃ and 85% by weight of compound (V-1) is applied by vapor deposition in a thickness of 40 nm. Thereafter, a 20 nm thick electron transport layer is deposited consisting of 50% by weight of compound (C-1) and of 50% of Liq. Finally a 2 nm KF layer serves as an electron injection layer and a 100 nm-thick Al electrode completes the device. All fabricated parts are sealed with a glass lid and a getter in an inert nitrogen atmosphere. The characterization of the device is performed as in example 1.

Comparative Application Example 2

The device is fabricated as in Application Example 5, except that the blocker A-51 is replaced by compound

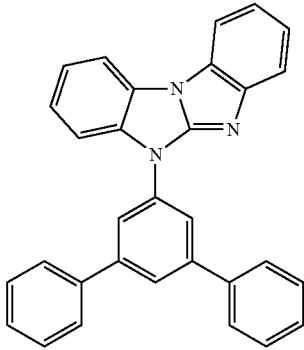 [SMILES: c1ccc(-c2cc(-c3ccccc3)cc(-n3c4ccccc4n4c5ccccc5nc34)c2)cc1]

(V-2; WO2011160757).

As shown in the table below, compound A-51 leads due to a better hole injection to a reduced voltage as compared to compound V-2 and thus also better quantum efficiency.

|  | EBL | Voltage @ 300 nits [V] | EQE[1)] @ 300 nits [%] | CIE |
|---|---|---|---|---|
| Appl. Ex. 5 | A-51 | 7.26 | 9.16 | 0.275 |
| Comp. Appl Ex. 2 | V-2 | 8.05 | 8.10 | 0.276 |

The invention claimed is:
1. A compound of the formula

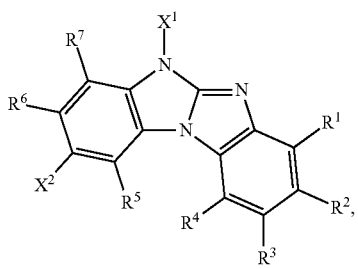

(I)

wherein
$R^1$, $R^2$, $R^3$, $R^4$, $R^5$, $R^6$ and $R^7$ are independently selected from the group consisting of H; a $C_1$-$C_{25}$ alkyl group, which can optionally be substituted by E and/or interrupted by D; a $C_6$-$C_{24}$ aryl group, which can optionally be substituted by G; and a $C_2$-$C_{30}$ heteroaryl group, which can optionally be substituted by G;
$X^1$ is a group of formula -$(A^1)_o$-$(A^2)_p$-$(A^3)_q$-$(A^4)_r$—$R^{16'}$, o is 0 or 1, p is 0 or 1, q is 0 or 1, r is 0 or 1,
$A^1$, $A^2$, $A^3$ and $A^4$ are independently selected from the group consisting of a $C_6$-$C_{24}$ arylene group, which can optionally be substituted by G, and a $C_2$-$C_{30}$ heteroarylene group, which can optionally be substituted by G; wherein
the groups $A^1$, $A^2$, $A^3$ and $A^4$ may be interrupted by a group —(SiR$^{17}$R$^{18}$)—;
$X^2$ is a group of formula -$(A^5)_v$-$(A^6)_s$-$(A^7)_t$-$(A^8)_u$—$R^{15}$, —NR$^{10}$R$^{11}$, or Si(R$^{12}$)(R$^{13}$)(R$^{14}$), v is 0 or 1, s is 0 or 1, t is 0 or 1, u is 0 or 1,
$A^5$, $A^6$, $A^7$ and $A^8$ are independently selected from the group consisting of a $C_6$-$C_{24}$ arylene group, which can optionally be substituted by G, and a $C_2$-$C_{30}$ heteroarylene group, which can optionally be substituted by G; wherein
the groups $A^5$, $A^6$, $A^7$ and $A^8$ may be interrupted by a group —(SiR$^{17}$R$^{18}$)—;
$R^{10}$ and $R^{11}$ are independently selected from the group consisting of a $C_6$-$C_{24}$ aryl group, which can optionally be substituted by G; and a $C_2$-$C_{30}$ heteroaryl group, which can optionally be substituted by G; or $R^{10}$ and $R^{11}$ together with the nitrogen atom to which they are bonded form a heteroaromatic ring, or ring system;
$R^{12}$, $R^{13}$ and $R^{14}$ are independently selected from the group consisting of a $C_1$-$C_{25}$alkyl group, which can optionally be substituted by E and/or interrupted by D; $C_6$-$C_{24}$aryl group, which can optionally be substituted by G; and a $C_2$-$C_{30}$heteroaryl group, which can optionally be substituted by G;
$R^{15}$ is a $C_6$-$C_{24}$aryl group, which can optionally be substituted by G; or a $C_2$-$C_{30}$ heteroaryl group, which can optionally be substituted by G;
$R^{16'}$ is a $C_6$-$C_{24}$aryl group, which can optionally be substituted by G; or a $C_2$-$C_{30}$ heteroaryl group, which can optionally be substituted by G;
$R^{17}$ and $R^{18}$ are independently selected from the group consisting of a $C_1$-$C_{25}$ alkyl group, and a $C_6$-$C_{24}$aryl group, which can optionally be substituted by a $C_1$-$C_{25}$ alkyl group;
D is —CO—, —COO—, —S—, —SO—, —SO$_2$—, —O—, —NR$^{65}$—, —SiR$^{70}$R$^{71}$—, —POR$^{72}$—, —CR$^{63}$=CR$^{64}$—, or —C≡C—,
E is —OR$^{69}$, —SR$^{69}$, —NR$^{65}$R$^{66}$, —COR$^{68}$, —COOR$^{67}$, —CONR$^{65}$R$^{66}$, or halogen,
G is E; a $C_1$-$C_{18}$ alkyl group; a $C_6$-$C_{24}$ aryl group; a $C_6$-$C_{24}$ aryl group, which is substituted by F, $C_1$-$C_{18}$ alkyl, or $C_1$-$C_{18}$ alkyl which is interrupted by O; a $C_2$-$C_{30}$ heteroaryl group; or a $C_2$-$C_{30}$ heteroaryl group, which is substituted by F, $C_1$-$C_{18}$ alkyl, or $C_1$-$C_{18}$ alkyl which is interrupted by O;
$R^{63}$ and $R^{64}$ are independently selected from the group consisting of H, $C_6$-$C_{18}$ aryl; $C_6$-$C_{18}$ aryl which is substituted by $C_1$-$C_{18}$ alkyl or $C_1$-$C_{18}$ alkoxy; $C_1$-$C_{18}$ alkyl; and $C_1$-$C_{18}$ alkyl which is interrupted by —O—;
$R^{65}$ and $R^{66}$ are independently selected from the group consisting of a $C_6$-$C_{18}$ aryl group; a $C_6$-$C_{18}$ aryl which is substituted by $C_1$-$C_{18}$ alkyl or $C_1$-$C_{18}$ alkoxy; a $C_1$-$C_{18}$ alkyl group; and a $C_1$-$C_{18}$ alkyl group, which is interrupted by —O—; or
$R^{65}$ and $R^{66}$ together form a five or six membered ring,
$R^{67}$ is a $C_6$-$C_{18}$ aryl group; a $C_6$-$C_{18}$ aryl group, which is substituted by $C_1$-$C_{18}$ alkyl or $C_1$-$C_{18}$ alkoxy; a $C_1$-$C_{18}$ alkyl group; or a $C_1$-$C_{18}$ alkyl group, which is interrupted by —O—,
$R^{68}$ is H; a $C_6$-$C_{18}$ aryl group; a $C_6$-$C_{18}$ aryl group, which is substituted by $C_1$-$C_{18}$ alkyl or $C_1$-$C_{18}$ alkoxy; a $C_1$-$C_{18}$ alkyl group; or a $C_1$-$C_{18}$ alkyl group, which is interrupted by —O—,
$R^{69}$ is a $C_6$-$C_{18}$ aryl; a $C_6$-$C_{18}$ aryl, which is substituted by $C_1$-$C_{18}$ alkyl or $C_1$-$C_{18}$ alkoxy; a $C_1$-$C_{18}$ alkyl group; or a $C_1$-$C_{18}$ alkyl group, which is interrupted by —O—,
$R^{70}$ and $R^{71}$ are independently selected from the group consisting of a $C_1$-$C_{18}$ alkyl group, a $C_6$-$C_{18}$ aryl group, and a $C_6$-$C_{18}$ aryl group, which is substituted by $C_1$-$C_{18}$ alkyl, and $R^{72}$ is a $C_1$-$C_{18}$ alkyl group, a $C_6$-$C_{18}$ aryl group, or a $C_6$-$C_{18}$ aryl group, which is substituted by $C_1$-$C_{18}$ alkyl;

wherein at least one of the following conditions (i)-(v) is true:

(i) when v is 0, s is 0, t is 0, and u is 0, then $R^6$ is not unsubstituted phenyl;

(ii) when v is 0, s is 0, t is 0, and u is 0, then $R^{15}$ is not unsubstituted phenyl;

(iii) $R^2$ is not unsubstituted phenyl;

(iv) $R^6$ is not unsubstituted phenyl; and (v) both conditions (iii) and (iv).

2. The compound according to claim 1, which is a compound of the formula

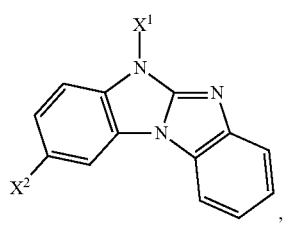

(Ia)

wherein $X^1$ and $X^2$ are as defined in claim 1.

3. The compound according to claim 1, wherein $X^1$ is a group of the formula -$A^1$-$(A^2)_p$-$(A^3)_q$-$(A^4)_r$—$R^{16}$ or -$(A^1)_o$-$(A^2)_p$-$(A^3)_q$-$(A^4)_r$—$R^{16'}$, o is 0 or 1, p is 0 or 1, q is 0 or 1, r is 0 or 1, $A^1$, $A^2$, $A^3$ and $A^4$ are independently selected from the group consisting of

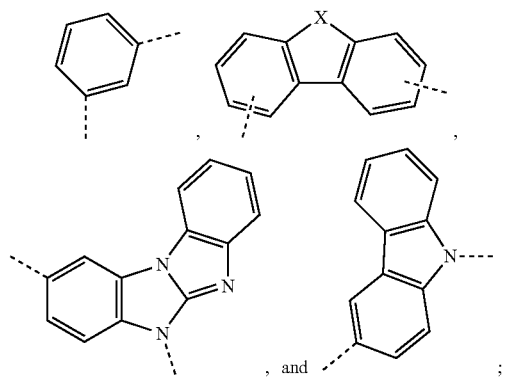

$R^{16}$ is a s group of the formula

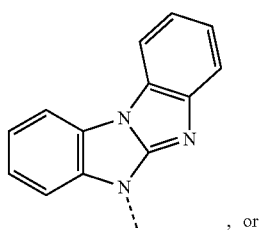

, or

-continued

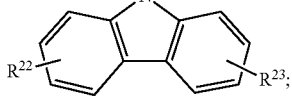

$R^{16'}$ is a group of the formula

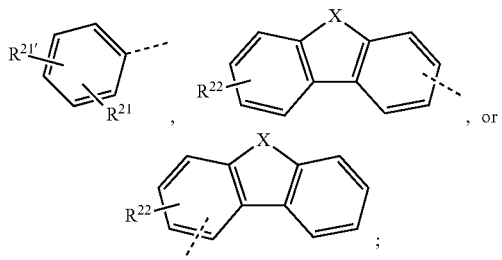

, or

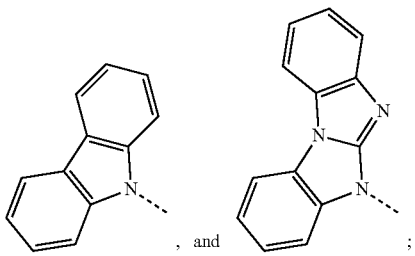

;

$R^{21}$ and $R^{21'}$ are independently selected from the group consisting of H, a phenyl group, and a $C_1$-$C_{18}$ alkyl group;

$R^{22}$ and $R^{23}$ are independently selected from the group consisting of H,

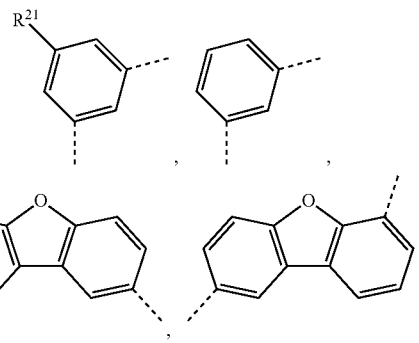

X is O, S, or $NR^{24}$, and $R^{24}$ is a $C_6$-$C_{24}$ aryl group, or a $C_2$-$C_{30}$ heteroaryl group, which can optionally be substituted by G, wherein G is as defined in claim 1.

4. The compound according to claim 1, wherein $X^1$ is a group of the formula -$A^1$-$(A^2)_p$-$(A^3)_q$-$(A^4)_r$—$R^{16}$, or -$(A^1)_o$-$(A^2)_p$-$(A^3)_q$-$(A^4)_r$—$R^{16'}$, o is 0 or 1, p is 0 or 1, q is 0 or 1, r is 0 or 1, $A^1$, $A^2$, $A^3$ and $A^4$ are independently selected from the group consisting of -continued
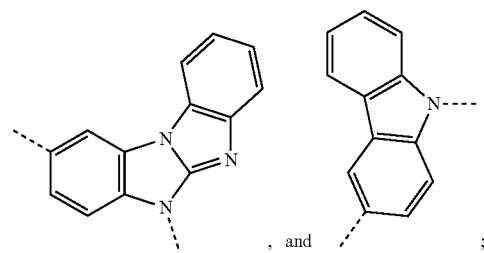
, and ;
$R^{16}$ is a group of the formula
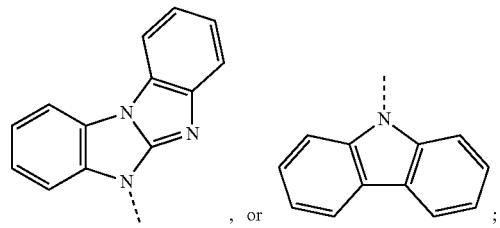
, or ;
$R^{16'}$ is a group of the formula
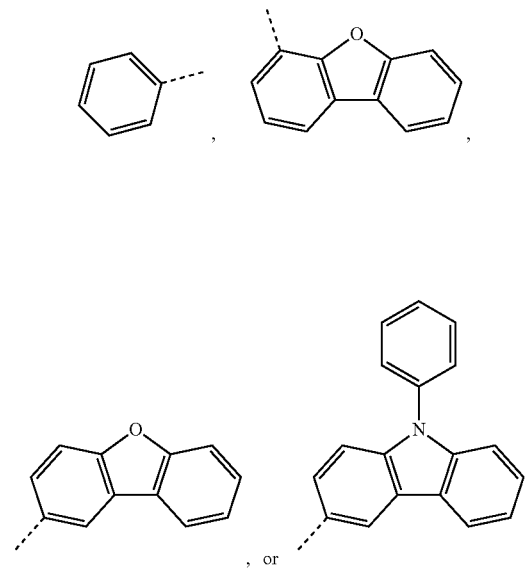
, or ;
and
$R^{21}$ is a group of the formula
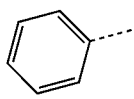
.
5. The compound according to claim 1, wherein $X^1$ is
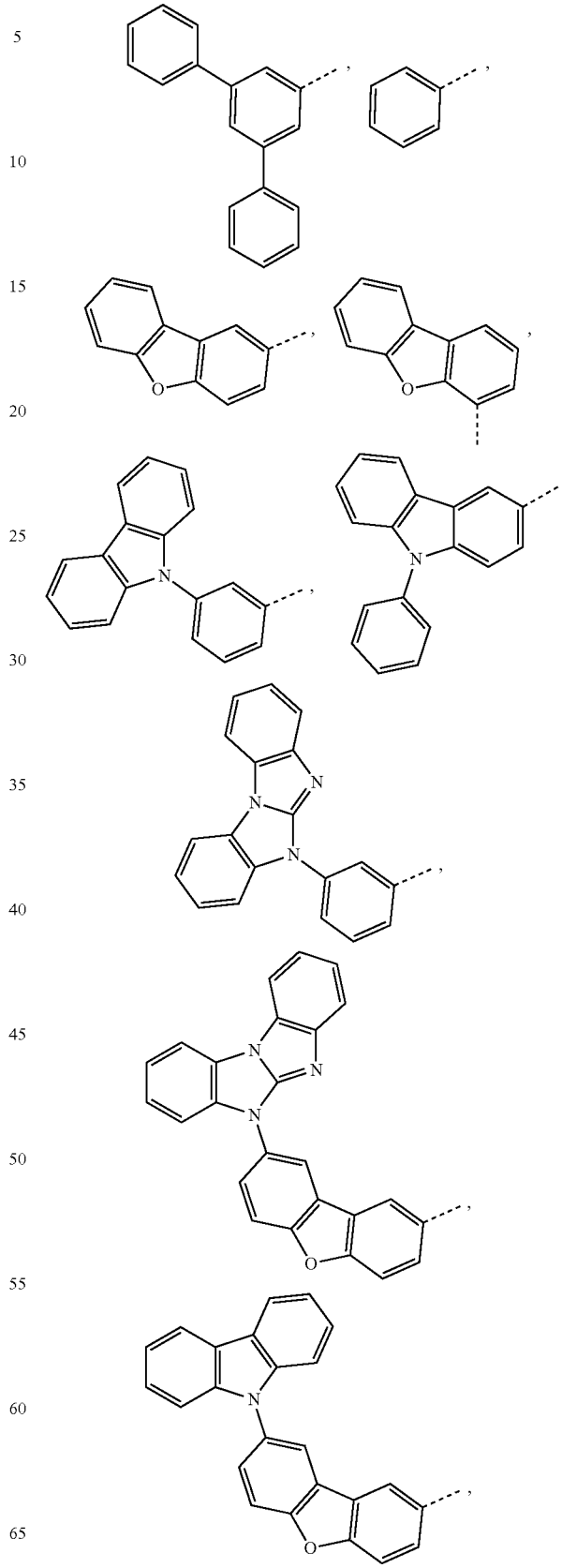

115
-continued
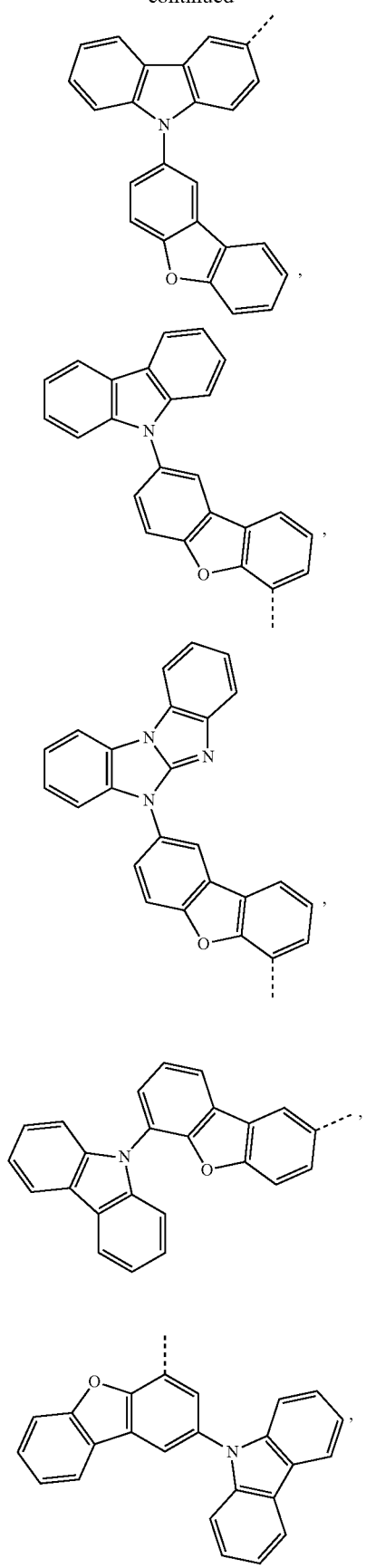
116
-continued
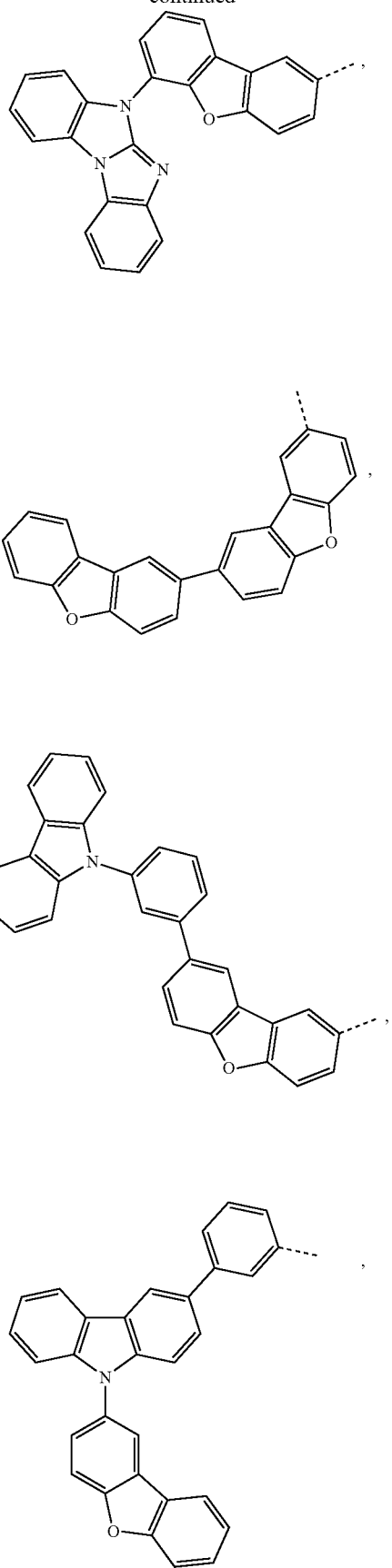

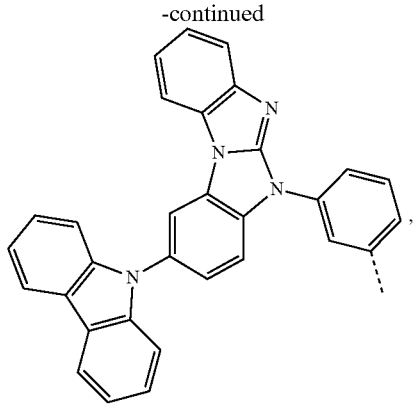
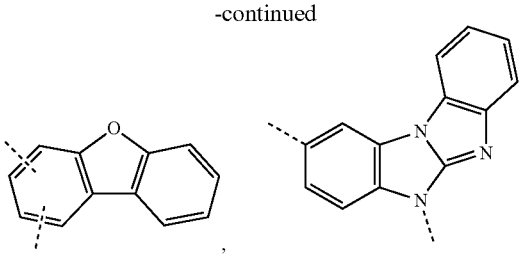
6. The compound according to claim 1, wherein $X^2$ is a group of formula $-(A^5)_v-(A^6)_s-(A^7)_t-(A^8)_u—R^{15}$,
v is 0 or 1, s is 0 or 1, t is 0 or 1, u is 0 or 1,
$A^5$, $A^6$, $A^7$ and $A^8$ are independently selected from the group consisting of
$R^{15}$ is a group of the formula
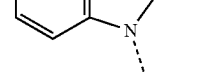
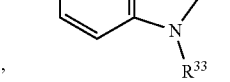
$R^{26}$, $R^{27}$, $R^{29}$ and $R^{32}$ are independently selected from the group consisting of H,

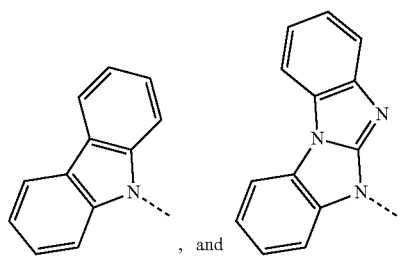, and ;
$R^{30}$ and $R^{33}$ are independently selected from the group consisting of
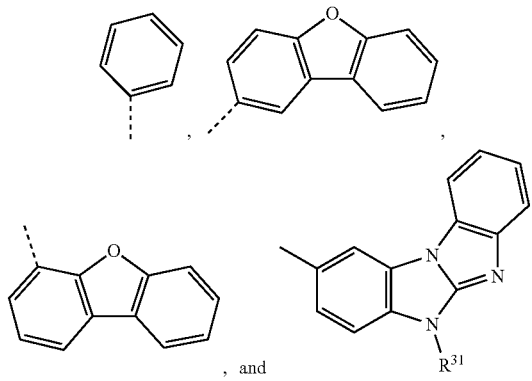, and ;
and
$R^{31}$ is
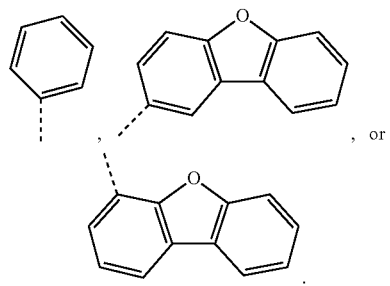, or
7. The compound according to claim 1, wherein $X^2$ is a group of formula $-(A^5)_v-(A^6)_s-(A^7)_t-(A^8)_u-R^{15}$, v is 0 or 1, s is 0 or 1, t is 0 or 1, u is 0 or 1,
$A^5$, $A^6$, $A^7$ and $A^8$ are independently selected from the group consisting of
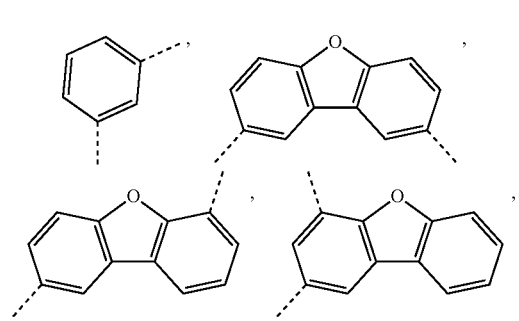
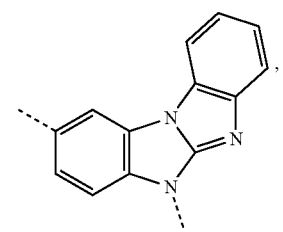
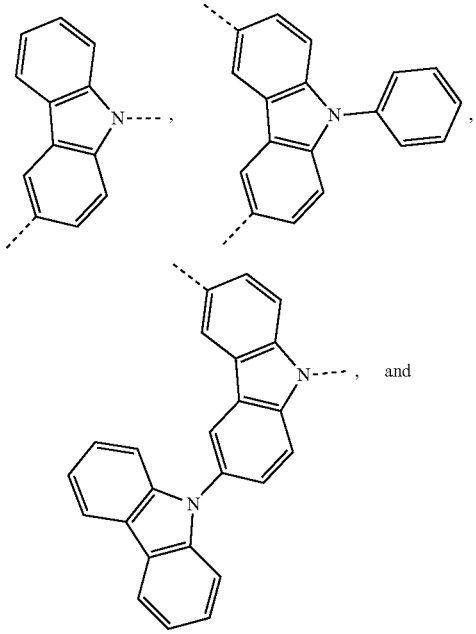, and
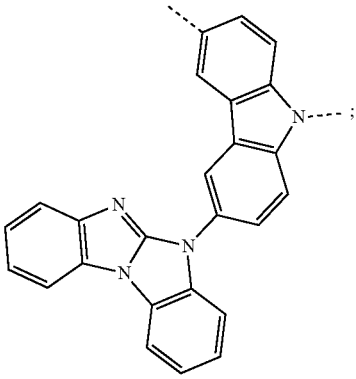
$R^{15}$ is a group of the formula
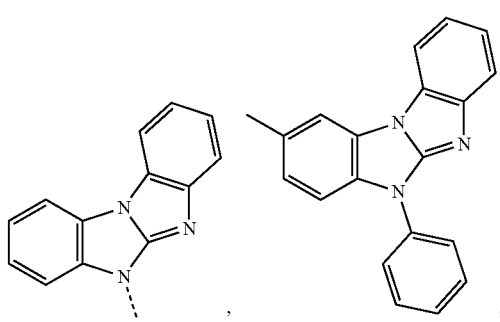

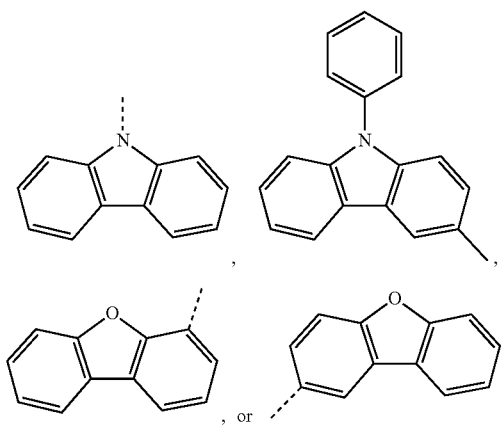
8. The compound according to claim 1, wherein $X^2$ is
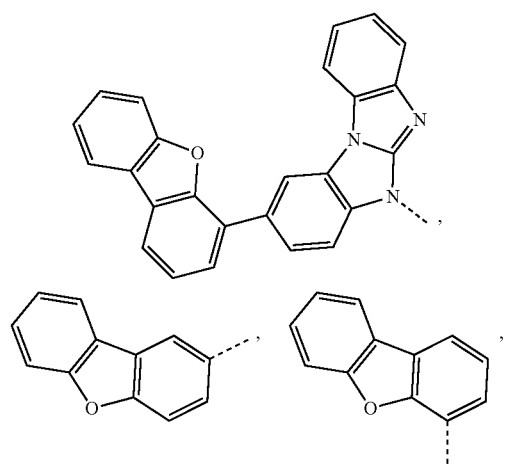
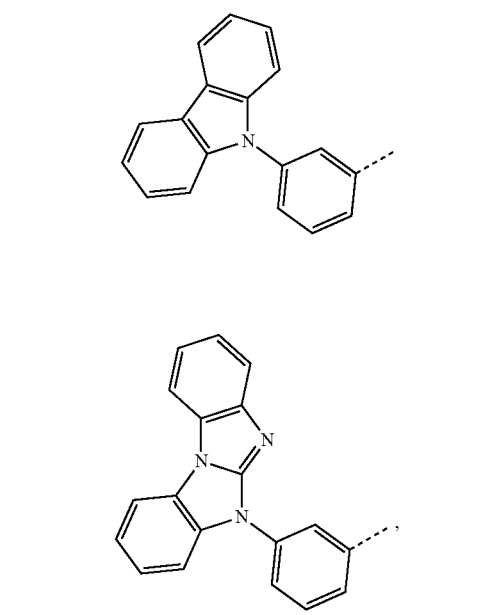
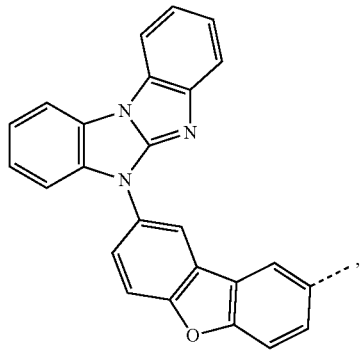
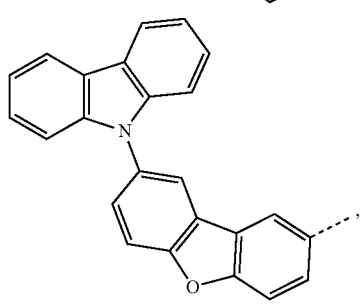
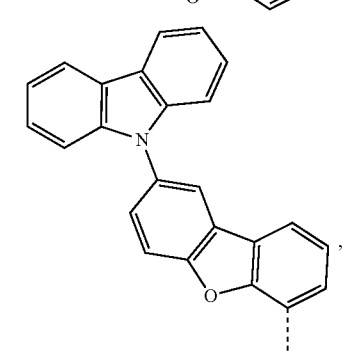
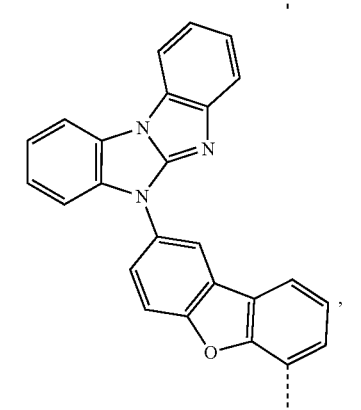
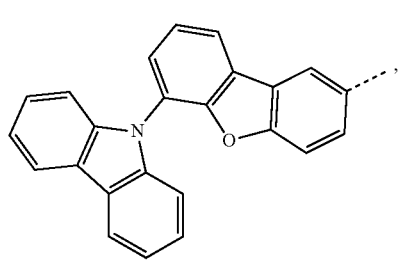

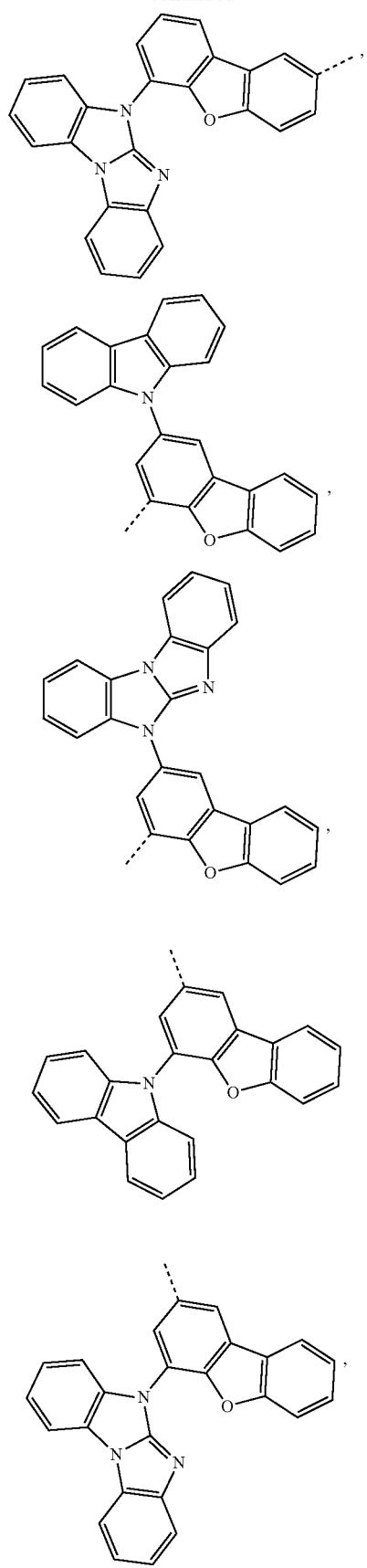
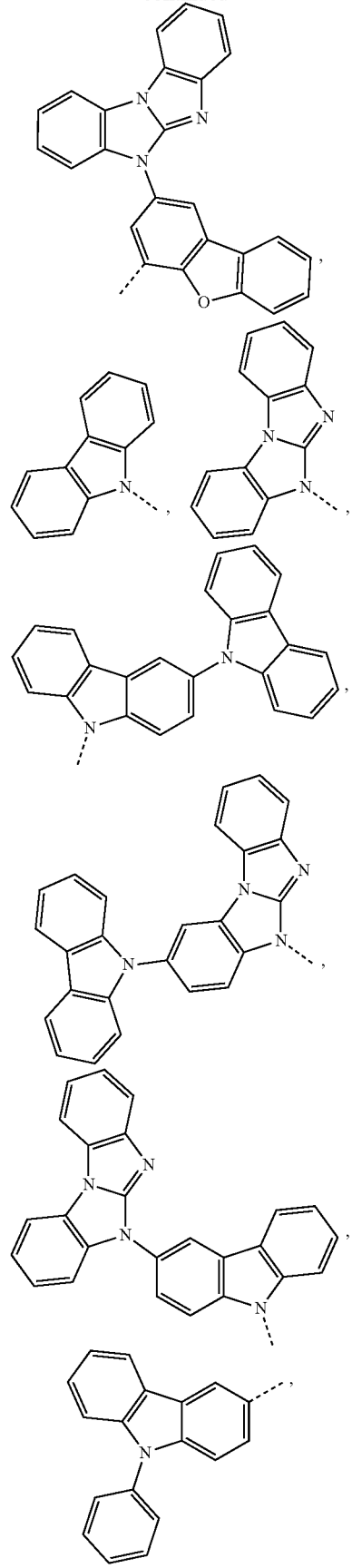

125
-continued
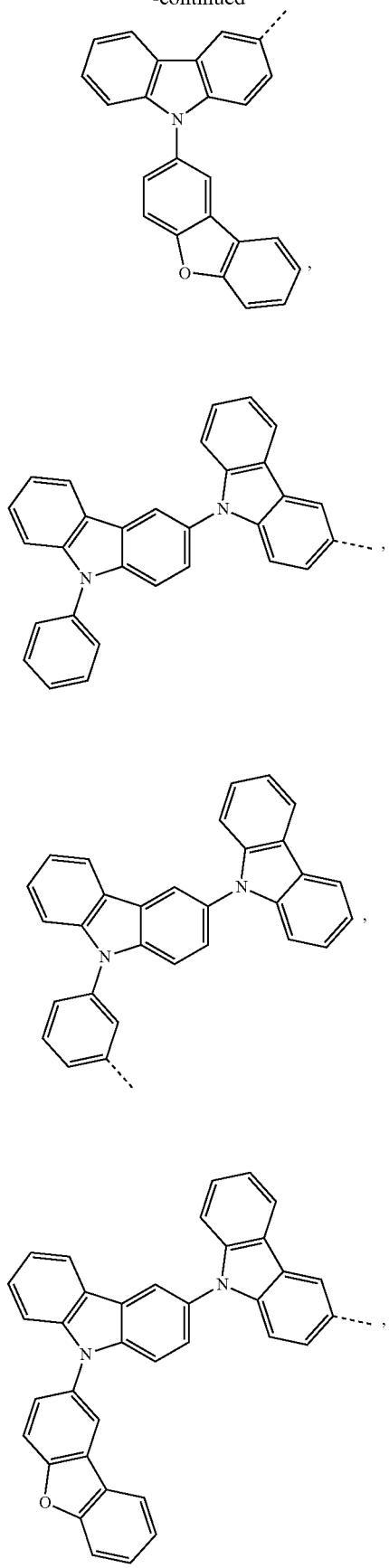
126
-continued
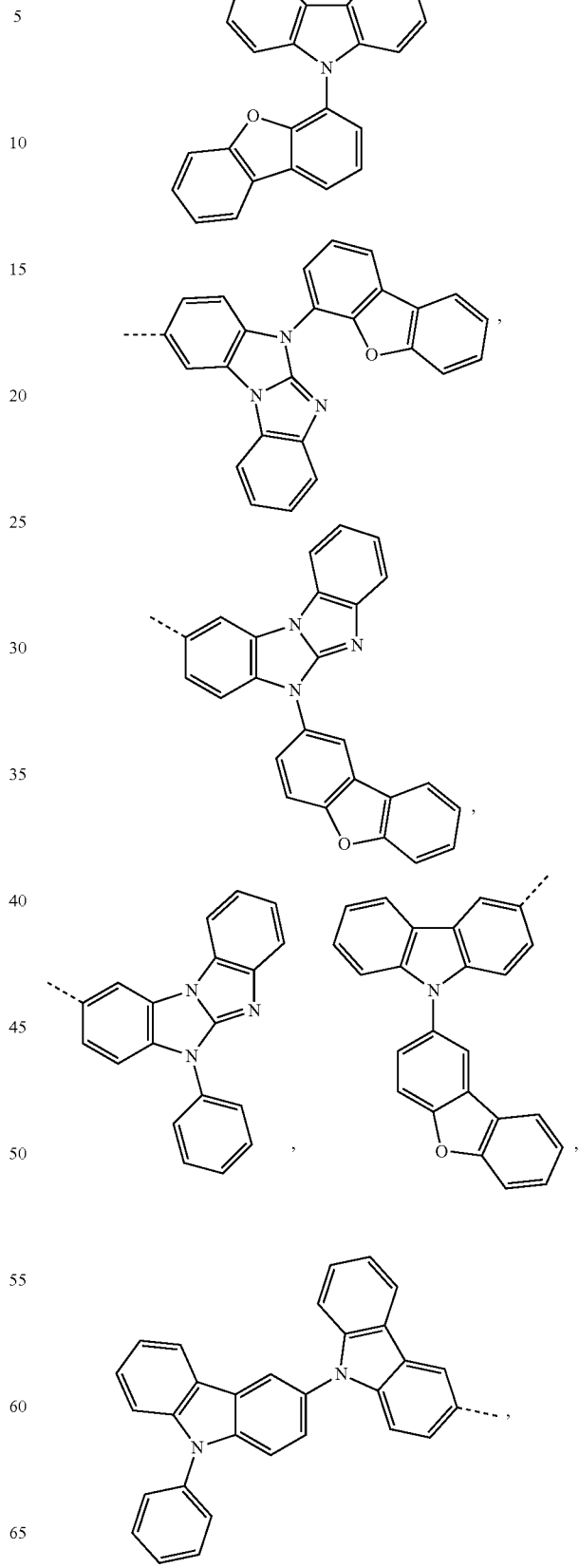

127
-continued
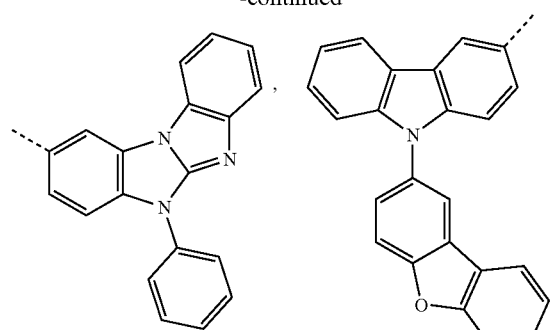
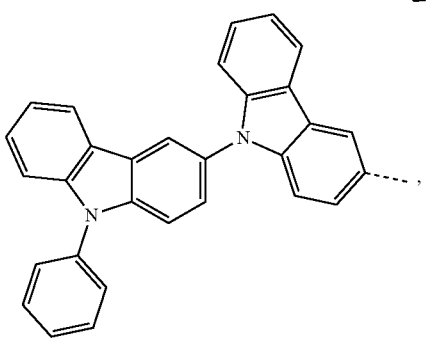
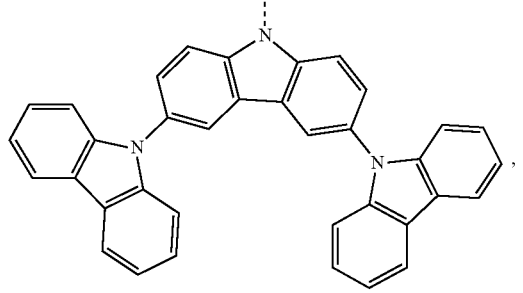
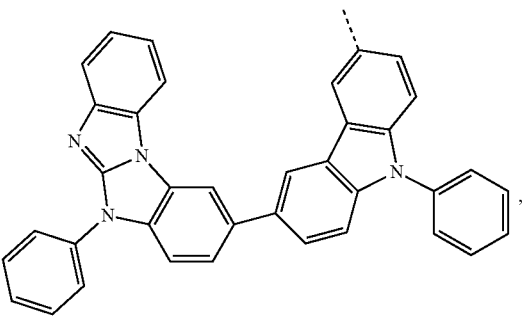
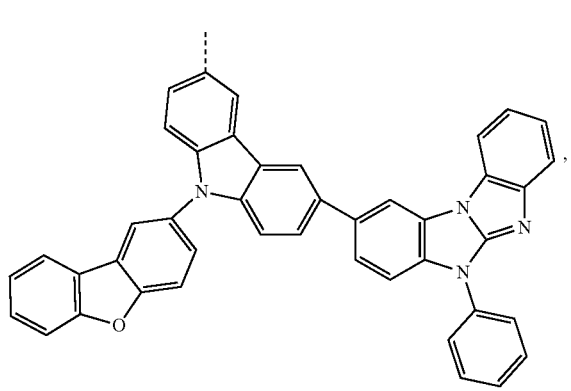
128
-continued
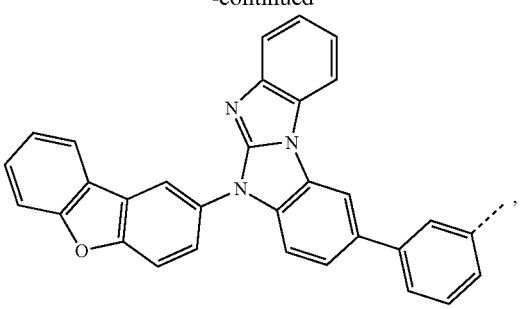
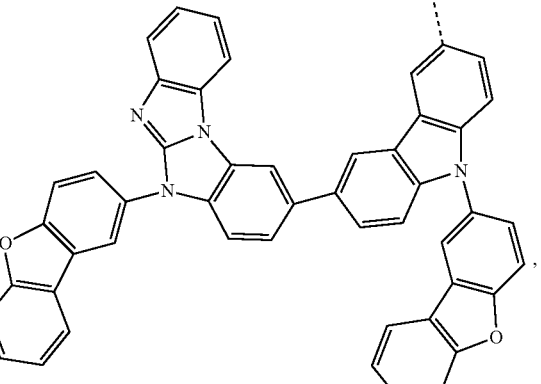
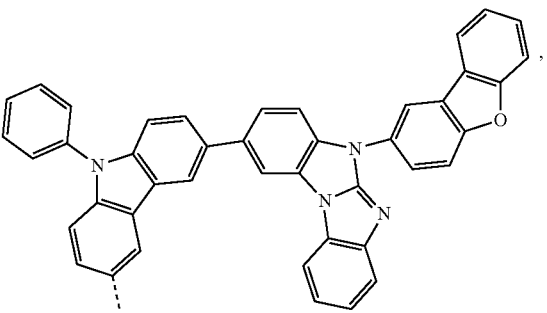
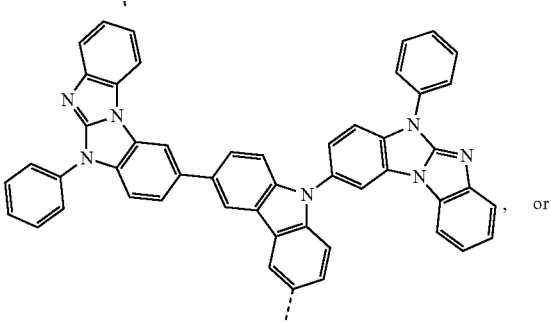 or
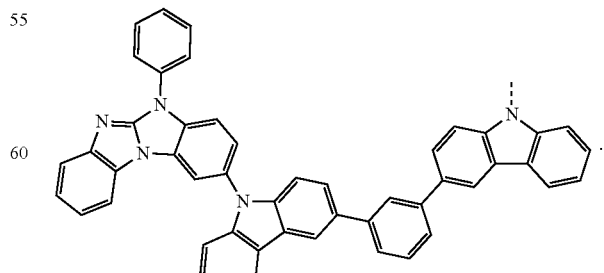

9. The compound according to claim 1, which is a following compound:
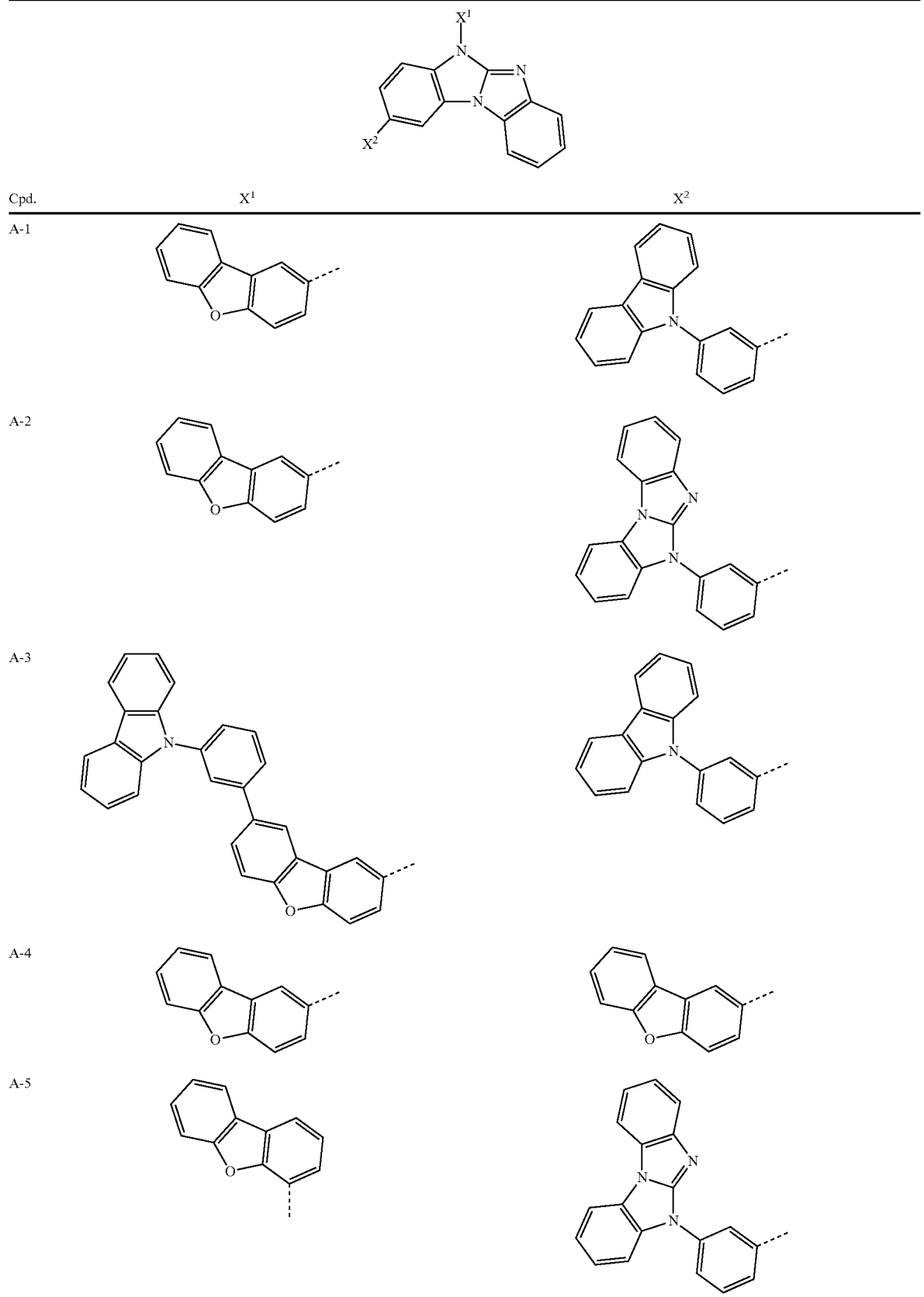

-continued
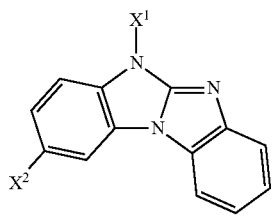
| Cpd. | X¹ | X² |
|---|---|---|
| A-6 | 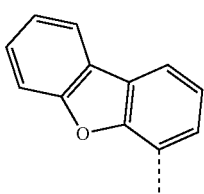 | 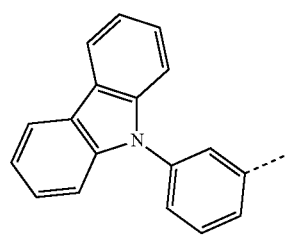 |
| A-7 | 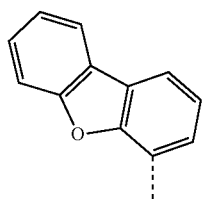 | 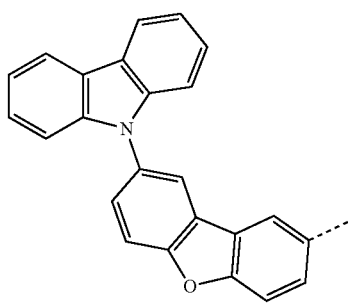 |
| A-8 | 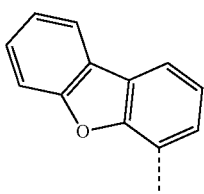 | 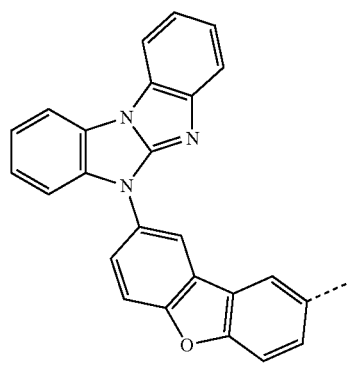 |
| A-9 | 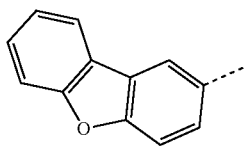 | 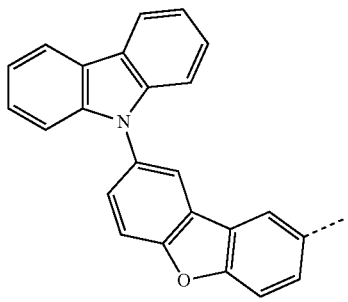 |

-continued
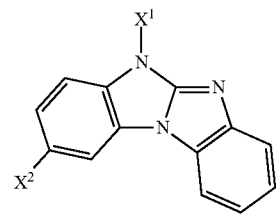
| Cpd. | X¹ | X² |
|---|---|---|
| A-10 | 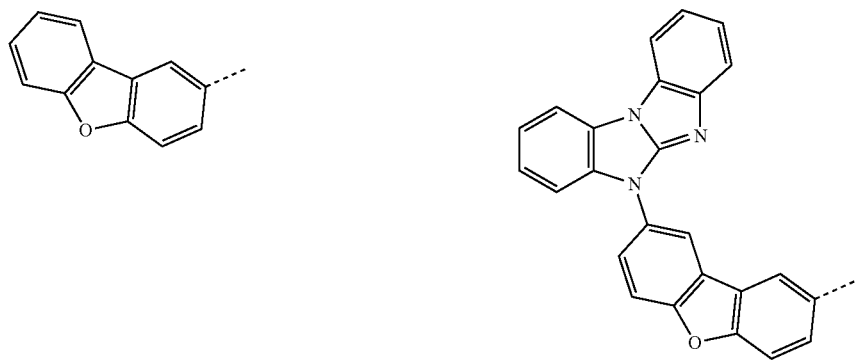 | |
| A-11 |  | |
| A-12 | 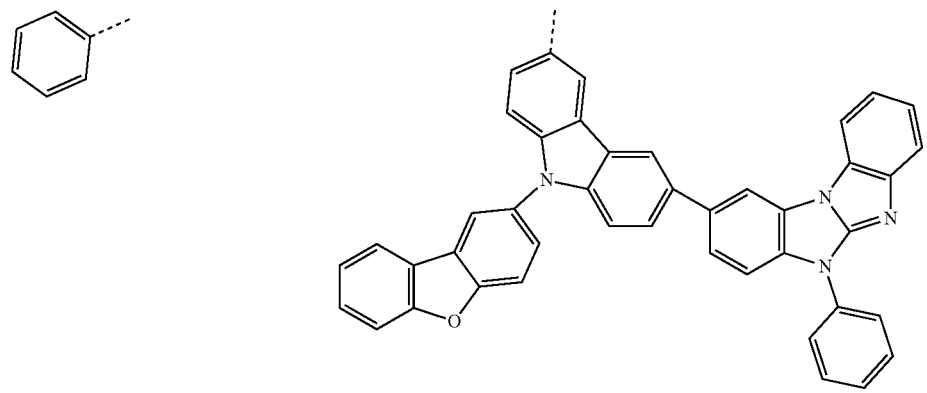 | |

-continued
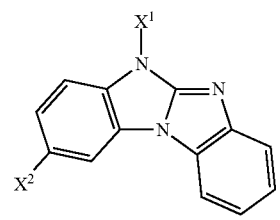
| Cpd. | X¹ | X² |
|---|---|---|
| A-13 | | |
| A-14 | | |
| A-15 | | |
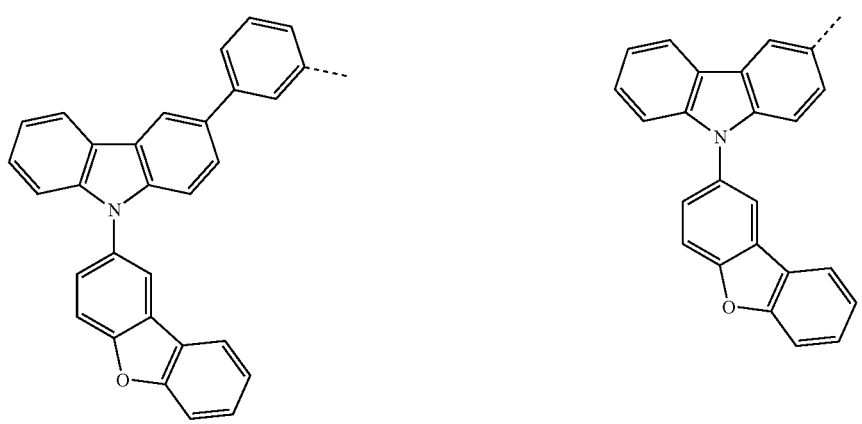
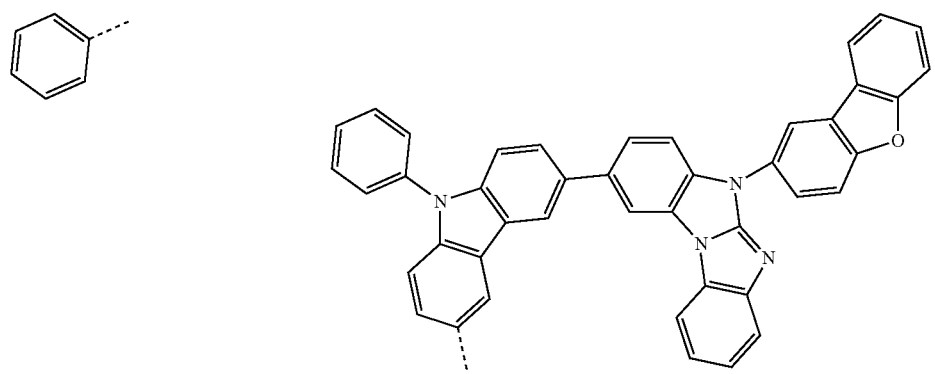
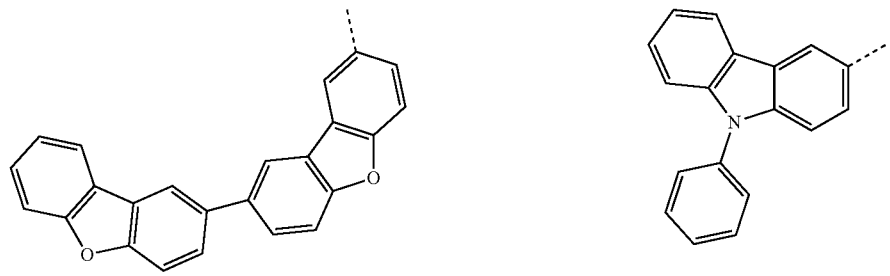

-continued
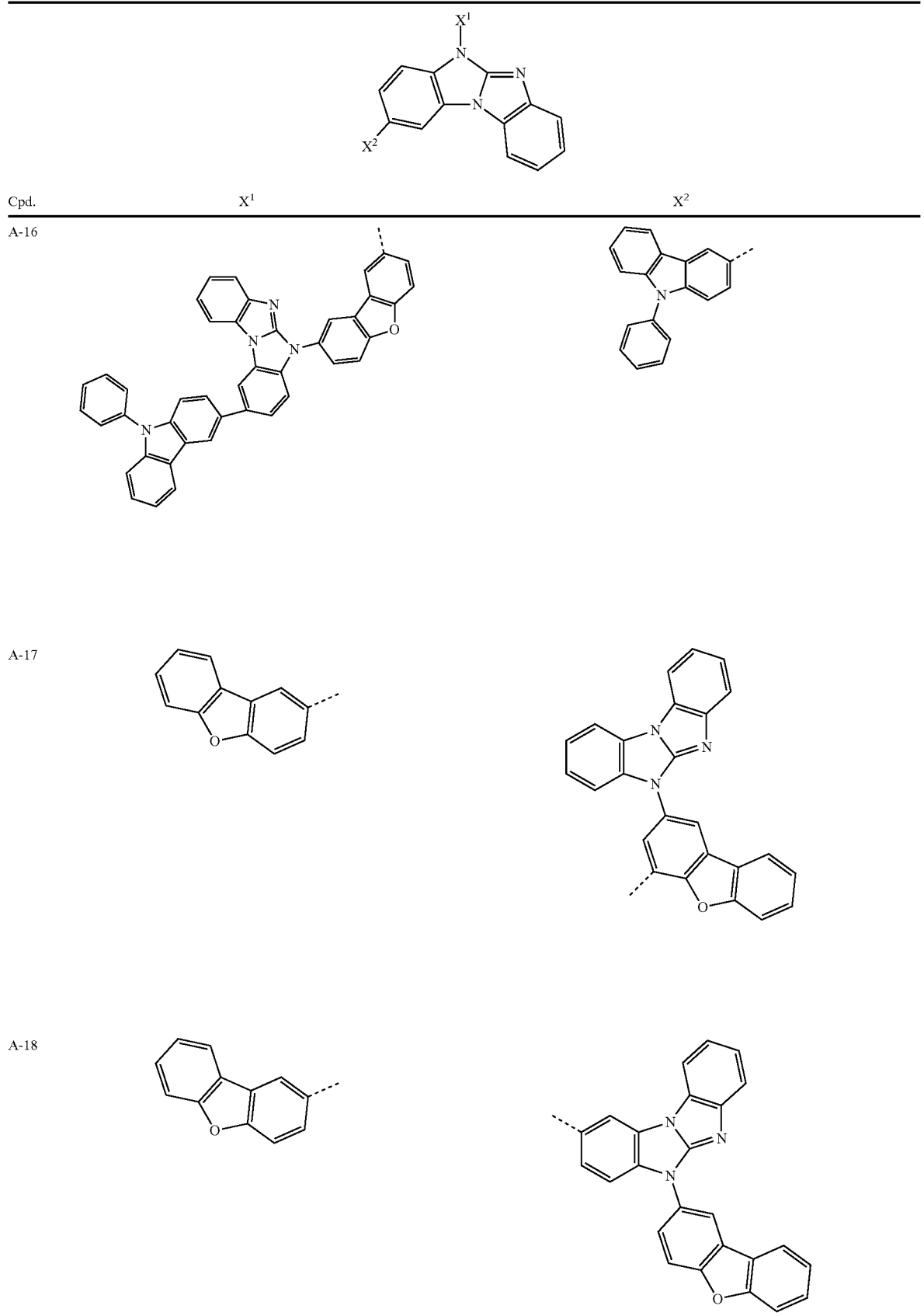

-continued
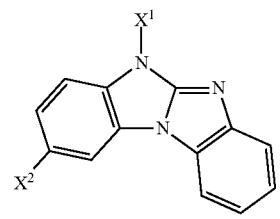
| Cpd. | X$^1$ | X$^2$ |
|---|---|---|
| A-19 | 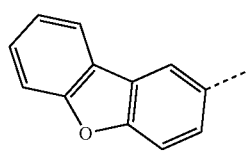 | 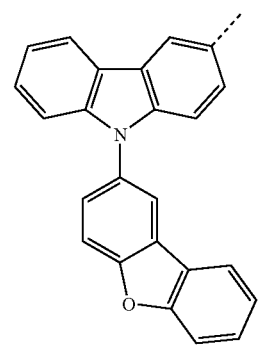 |
| A-20 | 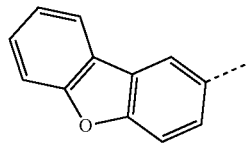 | 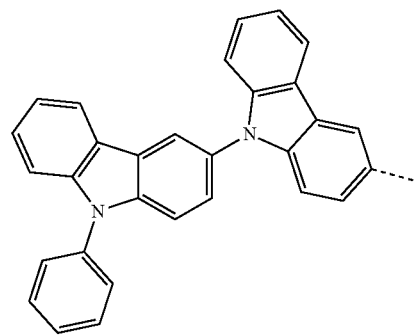 |
| A-21 | 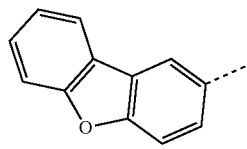 | 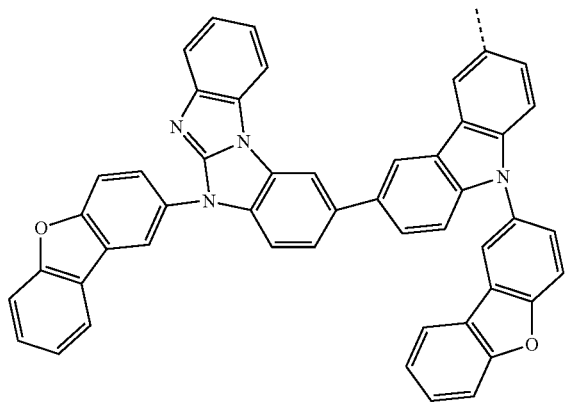 |

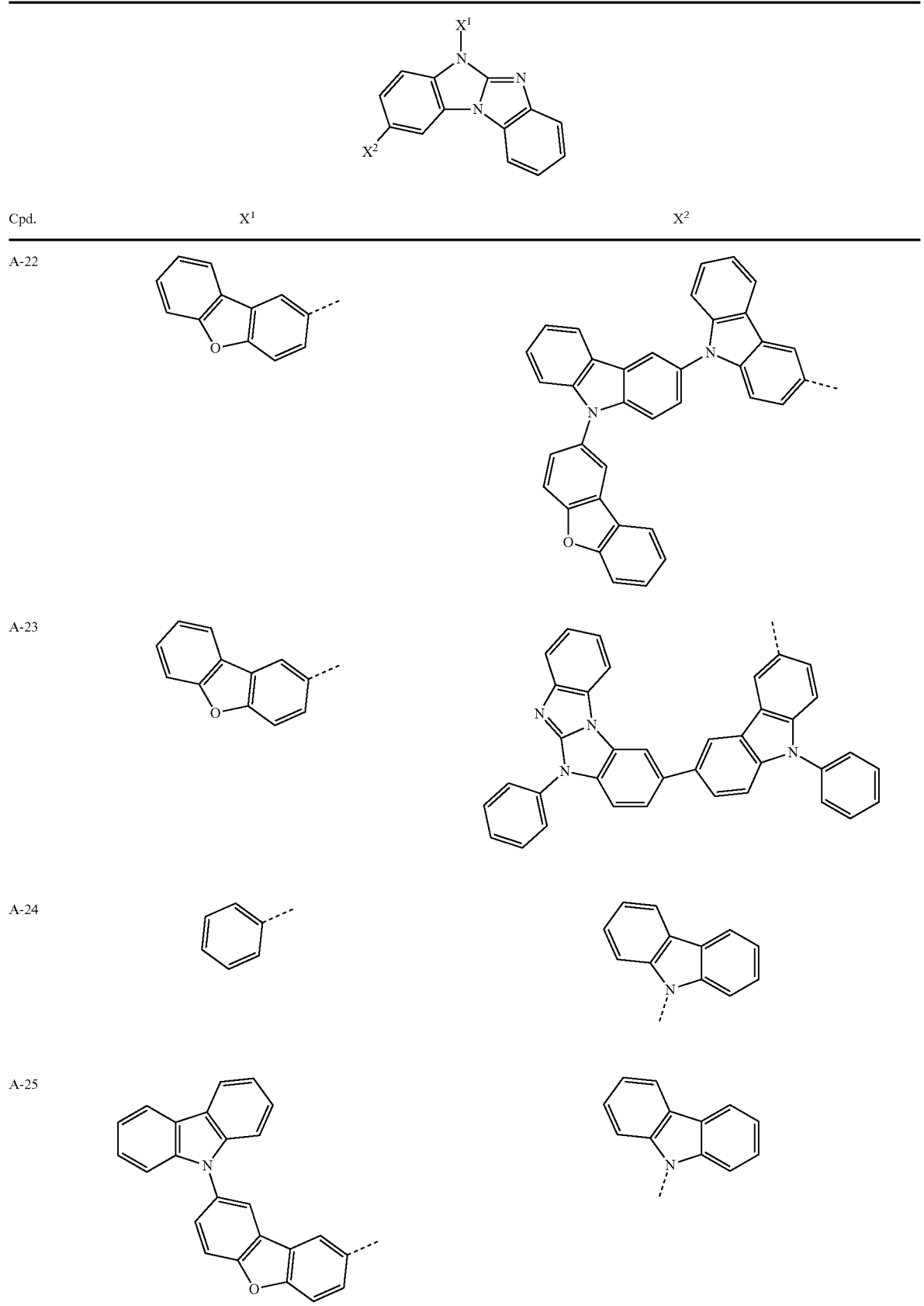

-continued
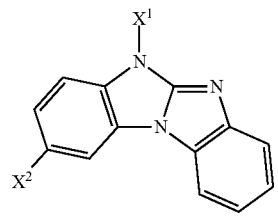
| Cpd. | X¹ | X² |
|---|---|---|
| A-26 | | |
| A-27 | | |
| A-28 | | |
| A-29 | | |

-continued
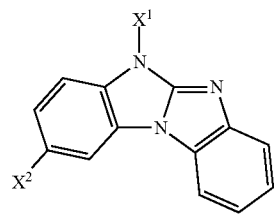
| Cpd. | X¹ | X² |
|---|---|---|
| A-30 | 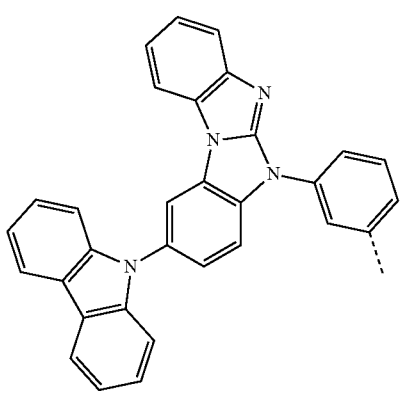 | 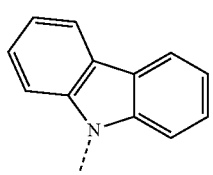 |
| A-31 | 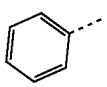 | 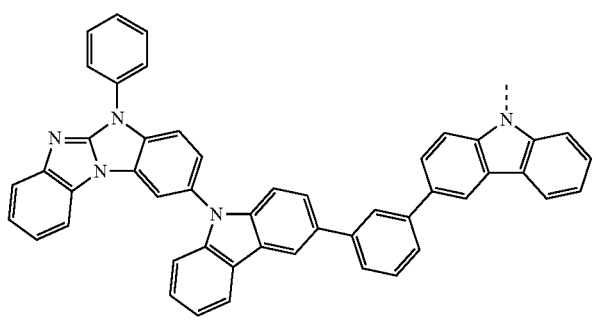 |
| A-32 | 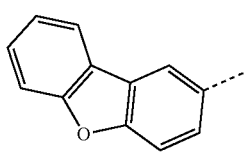 | 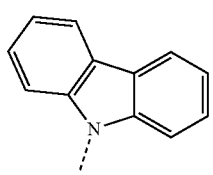 |
| A-33 | 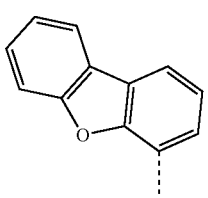 | 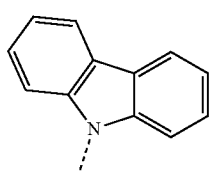 |

-continued
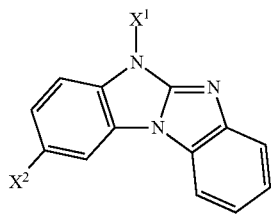
| Cpd. | X¹ | X² |
| --- | --- | --- |
| A-34 | 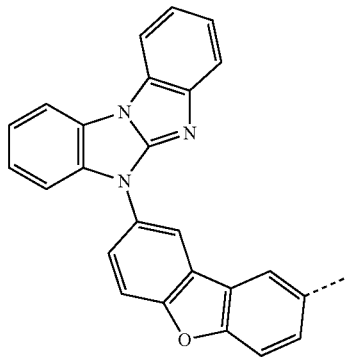 | 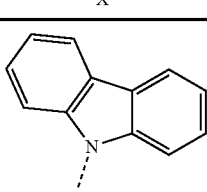 |
| A-35 | 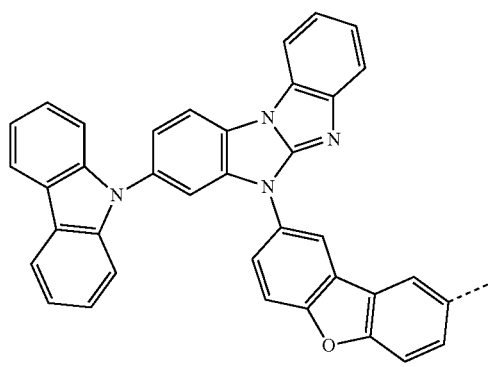 | 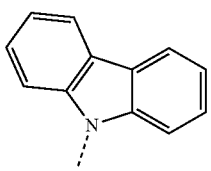 |
| A-36 | 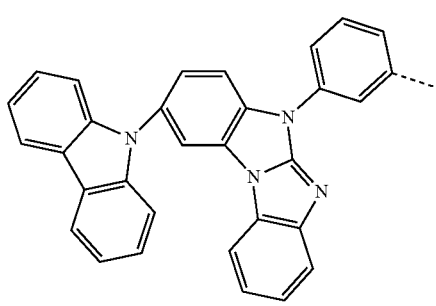 | 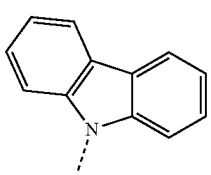 |
| A-37 | 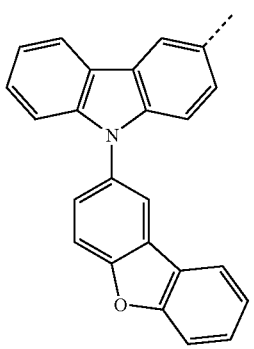 | 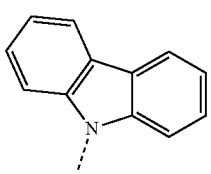 |

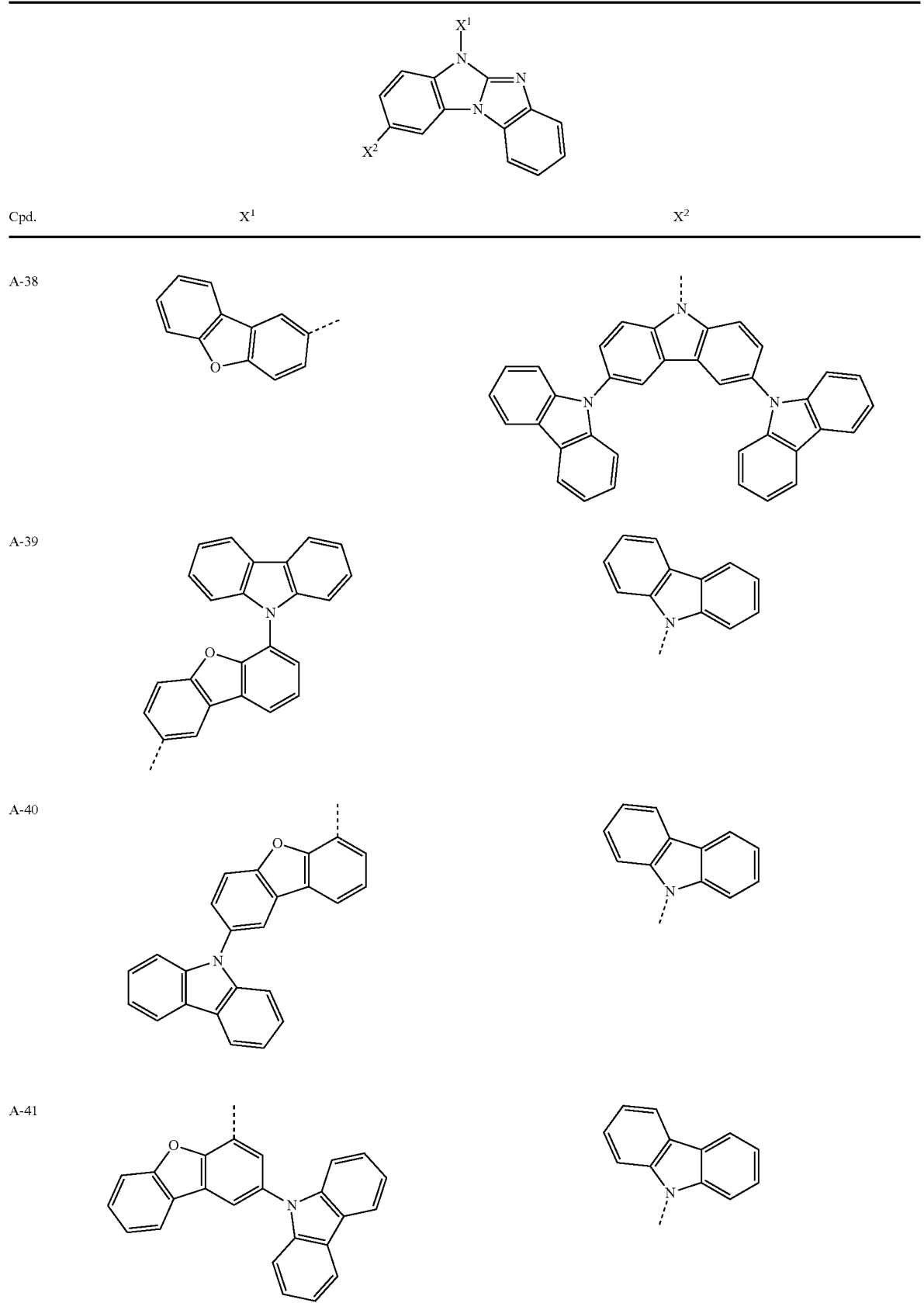

-continued
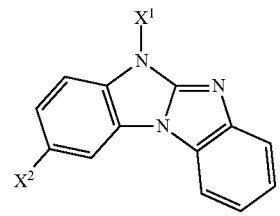
| Cpd. | X¹ | X² |
|---|---|---|
| A-42 | 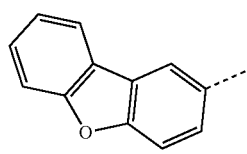 | 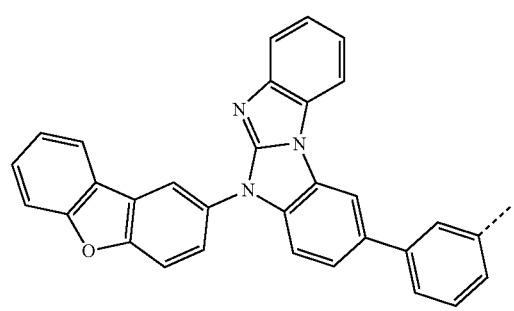 |
| A-43 | 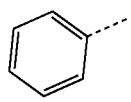 | 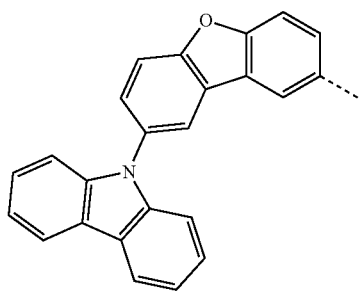 |
| A-44 | 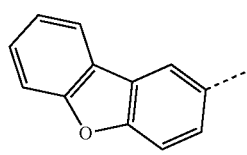 | 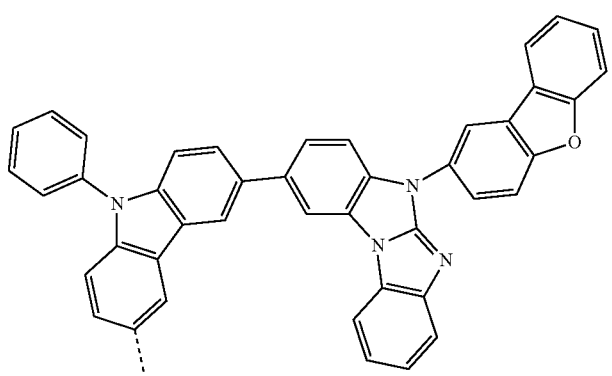 |
| A-45 | 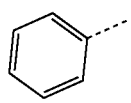 | 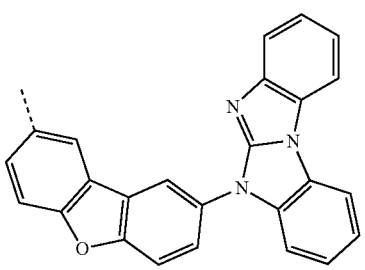 |

-continued
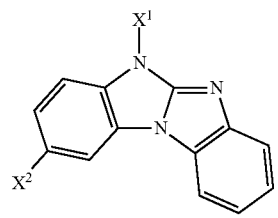
| Cpd. | X¹ | X² |
|---|---|---|
| A-46 | 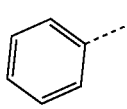 | 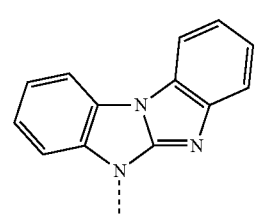 |
| A-47 | 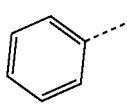 | 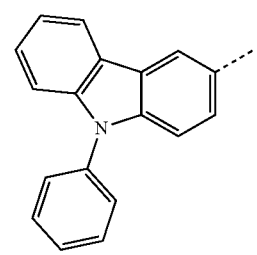 |
| A-48 | 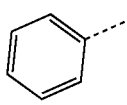 | 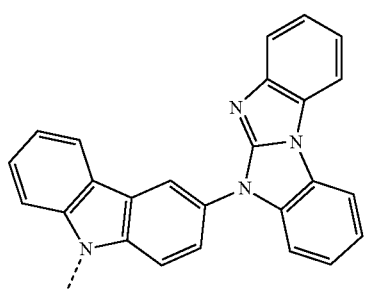 |
| A-49 | 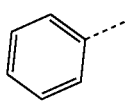 | 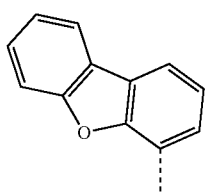 |
| A-50 | 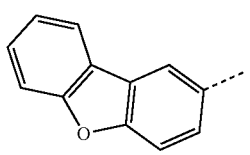 | 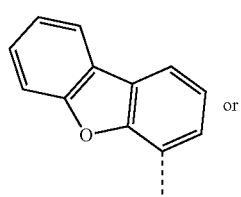 or |

-continued

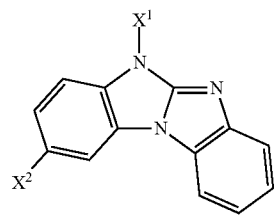

| Cpd. | X¹ | X² |
|---|---|---|
| A-51 | 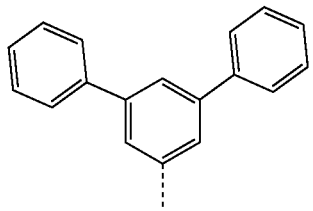 | 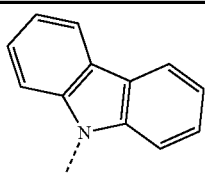 |

10. An electronic device, comprising a compound according to claim 1.

11. The electronic device according to claim 10, which is an electroluminescent device.

12. A hole transport layer, an electron/exciton blocking layer, or an emitting layer comprising a compound according to claim 1.

13. An emitting layer, comprising a compound according to claim 1 as host material in combination with a phosphorescent emitter.

14. An apparatus selected from the group consisting of a stationary visual display unit; a mobile visual display unit; an illumination unit; a keyboard; an item of clothing; furniture; and wallpaper, comprising the electronic device according to claim 10.

15. An electrophotographic photoreceptor, a photoelectric converter, an organic solar cell, a switching element, an organic light emitting field effect transistor, an image sensor, a dye laser and an electroluminescent device, comprising the compound of formula I according to claim 1.

* * * * *